(12) United States Patent
Kieke et al.

(10) Patent No.: US 6,300,065 B1
(45) Date of Patent: *Oct. 9, 2001

(54) YEAST CELL SURFACE DISPLAY OF PROTEINS AND USES THEREOF

(75) Inventors: Michele C. Kieke; K. Dane Wittrup, both of Urbana, IL (US); Eric T. Boder, Denver, CO (US); David M. Kranz, Champaign; Eric Shusta, Urbana, both of IL (US)

(73) Assignee: Board of Trustees of the University of Illinois, Urbana, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 21 days.

This patent is subject to a terminal disclaimer.

(21) Appl. No.: 09/140,084

(22) Filed: Aug. 26, 1998

Related U.S. Application Data

(63) Continuation-in-part of application No. 09/009,388, filed on Jan. 20, 1998, which is a continuation-in-part of application No. 08/866,398, filed on May 30, 1997, now abandoned.
(60) Provisional application No. 60/018,741, filed on May 31, 1996, now abandoned.

(51) Int. Cl.[7] .............................. C12P 21/02; C12Q 1/68; C12Q 1/02; C12N 15/63; C12N 15/81
(52) U.S. Cl. ........................ 435/6; 435/7.1; 435/7.2; 435/7.31; 435/320.1; 435/29; 435/69.1; 435/325; 435/348; 435/252.3; 435/254.11; 435/254.1; 435/254.21; 435/254.22; 435/254.23
(58) Field of Search .................. 435/5, 6, 7.1, 320.1, 435/7.2, 7.31, 29, 69.1, 325, 348, 252.3, 254.11, 254.1, 254.21, 254.22, 254.23

(56) References Cited

U.S. PATENT DOCUMENTS

| | | | |
|---|---|---|---|
| 4,946,778 | 8/1990 | Ladner et al. | 435/69.6 |
| 5,013,650 | 5/1991 | Carty | 435/69.1 |
| 5,223,409 | 6/1993 | Ladner et al. | 435/69.7 |
| 5,225,539 | 7/1993 | Winter | 530/387.3 |
| 5,258,289 | 11/1993 | Davis | 435/69.6 |
| 5,258,498 | 11/1993 | Huston et al. | 530/350 |
| 5,260,203 | 11/1993 | Ladner et al. | 530/387.3 |
| 5,316,922 | 5/1994 | Brown | 435/69.7 |
| 5,403,484 | 4/1995 | Ladner et al. | 435/235.1 |
| 5,411,873 | 5/1995 | Adams | 435/69.1 |
| 5,427,908 | 6/1995 | Dower | 435/5 |
| 5,482,858 | 1/1996 | Huston et al. | 435/252.33 |
| 5,510,240 | 4/1996 | Lam | 435/7.1 |
| 5,571,698 | 11/1996 | Ladner | 435/69.7 |
| 5,580,717 | 12/1996 | Dower | 435/5 |
| 5,624,817 * | 4/1997 | Miller et al. | 435/69.1 |
| 5,723,286 | 3/1998 | Dower et al. | 435/5 |
| 5,723,323 | 3/1998 | Kauffman et al. | 435/6 |
| 5,733,743 | 3/1998 | Johnson et al. | 435/69.1 |
| 5,763,192 | 6/1998 | Kauffman et al. | 435/7.1 |
| 5,780,225 | 7/1998 | Wigler et al. | 435/6 |
| 5,814,476 | 9/1998 | Kauffman et al. | 435/69.1 |
| 5,817,483 | 10/1998 | Kauffman et al. | 435/69.1 |
| 5,824,514 | 10/1998 | Kauffman et al. | 435/91.1 |
| 5,837,500 | 11/1998 | Ladner et al. | 435/69.7 |
| 5,858,657 | 1/1999 | Winter et al. | 435/6 |
| 5,866,344 | 2/1999 | Georgiou | 435/7.21 |
| 5,871,974 | 2/1999 | Huse | 435/69.7 |
| 5,900,476 * | 5/1999 | Ruggeri et al. | 530/380 |
| 6,027,910 | 2/2000 | Klis et al. | 435/41 |
| 6,114,147 | 9/2000 | Frenken et al. | 435/69.7 |

FOREIGN PATENT DOCUMENTS

| | | |
|---|---|---|
| 0 436 597 B1 | 4/1997 | (EP) . |
| 94/01567 | 1/1994 | (WO) . |
| WO 94/18330 | 8/1994 | (WO) . |
| 98/49286 | 11/1998 | (WO) . |

OTHER PUBLICATIONS

Maarten P. Schreuder, et al., Immobilizing Proteins on the Surface of Yeast Cells, TIBTECH, Apr. 1996, vol. 14.

Peter N. Lipke and Janet Kurjan, Sexual Agglutination in Budding Yeasts: Structure, Function, and Regulation of Adhesion Glycoproteins, Microbiological Reviews, Mar. 1992, pp. 180–194.

Jan Marcel van der Vaart, Identification and Characterization of Cell Wall Proteins of Saccharomyces ceevisiae, Sep. 19, 1965, pp. 1–138.

Daved H. Fremont, et al., Biophysical Studies of T–cell Receptors and Their Ligands, Current Opinion in Immunology, 1996, vol. 8, pp. 93–100.

Graham A. Bentlet and Roy A. Mariuzza, The Structure of the T Cell Antigen Receptor, Annu. Rev. Immunol., 1996, vol. 14, pp.563–590.

(List continued on next page.)

Primary Examiner—David Guzo
(74) Attorney, Agent, or Firm—Greenlee Winner and Sullivan, P.C.

(57) ABSTRACT

The present invention provides a genetic method for tethering polypeptides to the yeast cell wall in a form accessible for binding to macromolecules. Combining this method with fluorescence-activated cell sorting provides a means of selecting proteins with increased or decreased affinity for another molecule, altered specificity, or conditional binding. Also provided is a method for genetic fusion of the N terminus of a polypeptide of interest to the C-terminus of the yeast Aga2p cell wall protein. Attaching an scFv antibody fragment to the Aga2p agglutinin effectively mimics the cell surface display of antibodies by B cells in the immune system for affinity maturation in vivo. T cell receptor mutants can be isolated by this method that are efficiently displayed on the yeast cell surface, providing a means of altering T cell receptor binding affinity and specificity by library screening. As another embodiment, the selection method identifies proteins displayed at higher levels as proteins that are secreted at higher efficiency and that are more stable.

17 Claims, 33 Drawing Sheets

OTHER PUBLICATIONS

Kiyoshi Matsui, et al., Kinetics of T–cell Receptor Binding to Peptide/IEk Complexes: Correlation of the Dissociation Rate with T–cell Responsiveness, Proc. Natl. Acad. Sci. USA, Dec. 1994, pp. 12862–12866.

Pamela J. Bjorkman, MHC Restriction in Three Dimensions: A View of T Cell Receptor/Ligand Interactions, Cell, Apr. 18, 199, vol. 89, pp. 167–170.

Ziv Reich, et al., Ligand–specific Oligomerization of T–cell Receptor Molecules, Nature, Jun. 1997, vol. 387, pp. 617–620.

Daniel S. Lyons, et al., A TCR Binds to Antagonist Ligands with Lower Affinities and Faster Dissociation Rates Than to Agonists, Immunity Jul. 1996, vol. 5, pp. 53–61.

David H. Margulies, An Affinity for Learning, Nature, Jun. 13, 1996, vol. 381, pp. 558–559.

Sean M. O'Herrin, et al., Analysis of the Expression of Peptide–Major Histocompatibility Complexes Using High Affinity Soluble Divalent T Cell Receptors, J. Exp. Med., Oct. 20, 1997, vol. 186, pp. 1333–1345.

S. Munir Alam, et al., T–cell–receptor Affinity and Thymocyte Positive Selection, Nature, Jun. 13, 1996, pp. 616–620.

Kiyoshi Matsui, et al., Low Affinity Interaction of Peptide–MHC Complexes with T Cell Receptors, Science, Dec. 20, 1991, vol. 254, pp. 1788–1791.

Susanna Weber, et al., Specific Low–affinity Recognition of Major Histocompatibility Complex Plus Peptide by Soluble T–cell Receptor, Nature, Apr. 30, 1992, vol. 356, pp. 793–796.

Jean Marx, The T Cell Receptor Begins to Reveal Its Many Facets, Science, Jan. 27, 1995, vol. 267, pp. 459–460.

Yuri Syrulev, et al., The Law of Mass Action Governs Antigen–stimulated Cytolytic Activity of CD8+ cytotoxic T Lymphocytes, Proc. Natl. Acad. Sci. USA, Dec. 1995, vol. 92, pp. 11990–11992.

Beth A. Schodin, et al., Binding Properties and Solubility of Single–chain T Cell Receptors Expressed in E. Coli, Molecular Immunology, 1996, vol. 33, pp. 819–829.

Carol J. Schlueter, et al., Specificity and Binding Properties of a Single–chain T Cell Receptor, J. Mol. Biol., vol. 256, pp. 859–869.

Anand, R. et al. (1992), "Progress in developing methylotrophic yeasts as expression systems," TIBTECH 10:413–417.

Boder E.T. and Wittrup, K.D. (1997), "Yeast surface display for screening combinatorial polypeptide libraries," Nature Biotechnol. 15:553–557.

Boder, E.T. and Wittrup, K.D. (1995), "A Yeast Surface Display System for in vitro Affinity Maturation of Antibodies," Protein Interactions, Jun. 1–4, 1995, Beckman Institute, University of Illinois, Urbana, Abstract Only.

Buckholz, R.G. and Gleeson, M.A.G. (1991), "Yeast Systems for the Commercial Production of Heterologous Proteins," Bio/Technol. 9: 1067–1072.

Cregg, J.M. et al. (1993), "Recent Advances in the Expression of Foreign Genes in *Pichia pastoris*," Bio/Technol. 11:905–910.

Faber, K.N. et al. (1995), "Review: Methylotrophic Yeasts as Factories for the Production of Foreign Proteins," Yeast 11:1331–1344.

Hawkins, R.E. et al. (1992), "Selection of Phage Antibodies by Binding Affinity Mimicking Affinity Maturation," J. Mol. Biol. 226:889–896.

Hawkins, R.E. et al. (1993), "The Contribution of Contact and Non–contact Residues of Antibody in the Affinity of Binding to Antigen," J. Mol. Biol. 234:958–964.

Jung, S. and Plückthun (1997), "Improving in vivo folding and stability of a single–chain Fv antibody fragment by loop grafting," Protein Eng. 10(8):959–966.

Kieke, M.C. et al. (1997), "Isolation of anti–T cell receptor scFv mutants by yeast surface display," Protein Eng. 10(11):1303–1310.

Klis, F.M. (1994), "Review: Cell Wall Assembly in Yeast," Yeast 10:851–869.

Knappik, A. and Plückthun, A. (1995), "Engineered turns of a recombinant antibody improve its in vivo folding," Protein Eng. 8(1):81–89.

Nieba, L. et al. (1997), "Disrupting the hydrophobic patches at the antibody variable/constant domain interface: improved in vivo folding and physical characterization of an engineered scFv fragment," Protein Eng. 10(4):435–444.

Ridder, R. et al. (1995), "Generation of Rabbit Monoclonal Antibody Fragments from a Combinatorial Phage Display Library and Their Production in the Yeast *Pichia pastoris*," Bio/Technol. 13:255–259.

Romanos, M. (1995), "Advances in the use of *Pichia pastoris* for high–level gene expression," Curr. Opinion in Biotechnol. 6:527–533.

Sudbery, P.E. (1994), "The Non–Saccharomyces Yeasts," Yeast 10:1707–1726.

* cited by examiner

```
   1  ATTAGAATTC CCTACTTCAT ACATTTTCAA TTAAGATGCA GTTACTTCGC
  51  TGTTTTTCAA TATTTTCTGT TATTGCTTCA GTTTTAGCAC AGGAACTGAC
 101  AACTATATGC GAGCAAATCC CCTCACCAAC TTTAGAATCG ACGCCGTACT
 151  CTTTGTCAAC GACTACTATT TTGGCCAACG GGAAGGCAAT GCAAGGAGTT
 201  TTTGAATATT ACAAATCAGT AACGTTTGTC AGTAATTGCG GTTCTCACCC
 251  CTCAACAACT AGCAAAGGCA GCCCCATAAA CACACAGTAT GTTTTTAAGG
 301  ACAATAGCTC GACGATTGAA GGTACATACC CATACGACGT TCCAGACTAC
 351  GCTCTGCAGG CTAGCGACGT CGTTATGACT CAAACACCAC TATCACTTCC
 401  TGTTAGTCTA GGAGATCAAG CCTCCATCTC TTGCAGATCT AGTCAGAGCC
 451  TTGTACACAG TAATGGAAAC ACCTATTTAC GTTGGTACCT GCAGAAGCCA
 501  GGCCAGTCTC CAAAGGTCCT GATCTACAAA GTTTCCAACC GATTTTCTGG
 551  GGTCCCAGAC AGGTTCAGTC GCAGTGGATC AGGGACAGAT TTCACACTCA
 601  AGATCAGCAG AGTGGAGGCT GAGGATCTGG GAGTTTATTT CTGCTCTCAA
 651  AGTACACATG TTCCGTGGAC GTTCGGTGGA GGCACCAAGC TTGAAATTAA
 701  GTCCTCTGCT GATGATGCTA AGAAGGATGC TGCTAAGAAG GATGATGCTA
 751  AGAAAGATGA TGCTAAGAAA CATGGTGACG TCAAACTGGA TGAGACTGGA
 801  GGAGGCTTGG TGCAACCTGG GAGGCCCATG AAACTCTCCT GTGTTGCCTC
 851  TGGATTCACT TTTAGTGACT ACTGGATGAA CTGGGTCCGC CAGTCTCCAG
 901  AGAAAGGACT GGAGTGGGTA GCACAAATTA GAAACAAACC TTATAATTAT
 951  GAAACATATT ATTCAGATTC TGTGAAAGGC AGATTCACCA TGTCAAGAGA
1001  TGATTCCAAA AGTAGTGTCT ACCTGCAAAT GAACAACTTA AGAGTTGAAG
1051  ACATGGGTAT CTATTACTGT ACGGGTTCTT ACTATGGTAT GGACTACTGG
1101  GGTCAAGGAA CCTCAGTCAC CGTCTCCTCA GAACAAAAGC TTATTTCTGA
1151  AGAAGACTTG TAATAGCTCG AG
```

FIG. 7

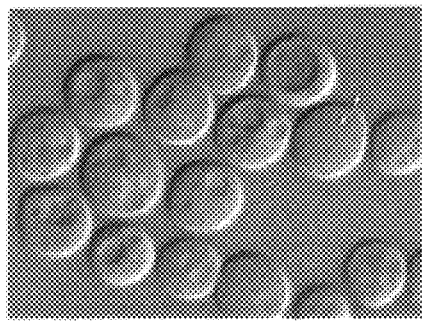
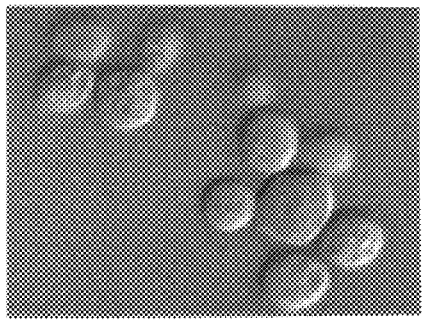
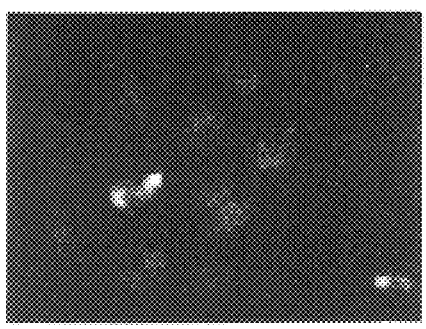
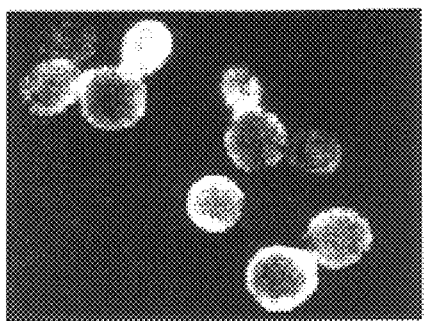
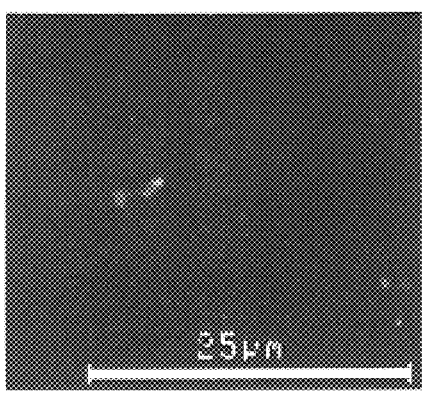
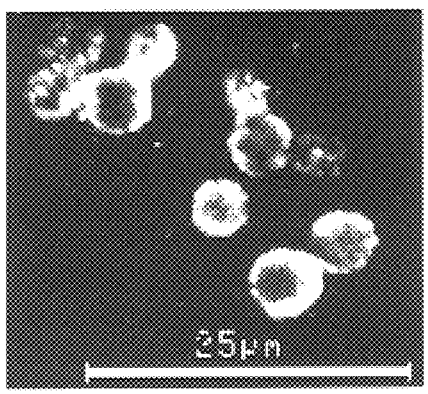
FIG. 8A        FIG. 8B Anti-c-*myc* scTCR
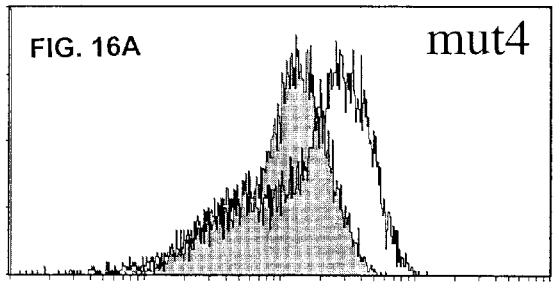
FIG. 16A mut4
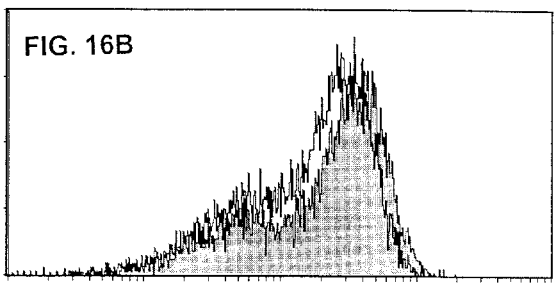
FIG. 16B
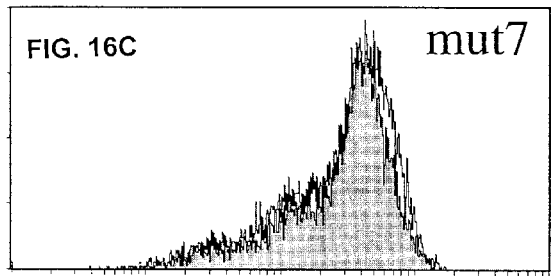
FIG. 16C mut7
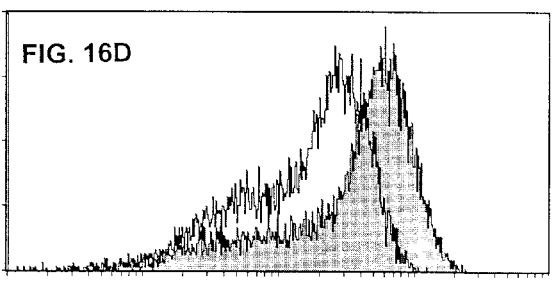
FIG. 16D
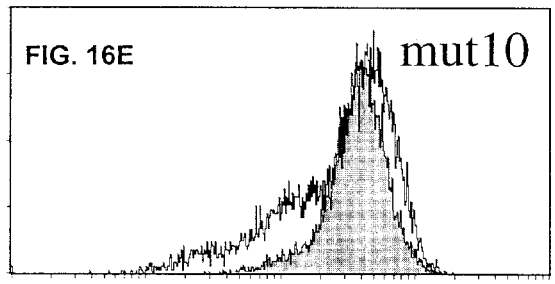
FIG. 16E mut10
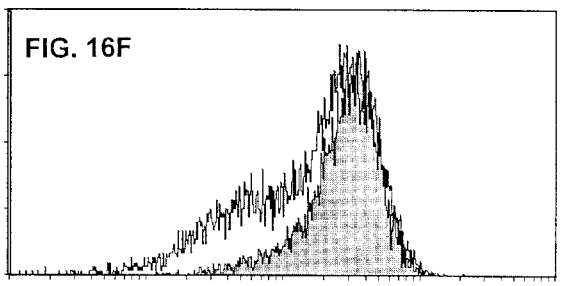
FIG. 16F

```
                    V_L
KJ16 wild-type      GACGTCCTGGTGACCCAAACTCCTGCCTCCCTGTCTGCATCTCCGGATGAATC
KJ16 mut 4          GACGTCCTGGTGACCCAAACTCCTGCCTCCCTGTCTGCATCTCCGGATGAATC
KJ16 mut 7          GACGTCCTGGTGACCCAAACTCCTGCCTCCCTGTCTGCATCTCCGGATGAATC --------CDR1----------
KJ16 wild-type      TGTCACCATCACATGCCAGGCAAGCCAGGACATTGGTACTTGCTTAGTTTGGT
KJ16 mut 4          TGTCACCATCACATGCCAGGCAAGCCAGGACATTGGTACTTGCTTAGTTTGGT
KJ16 mut 7          TGTCACCATCACATGCCAGGCAGGCCAGGACATTGGTACTTGCTTAGTTTGGT
                                         ↑
                                        S26R -------CDR2-------
KJ16 wild-type      ATCAGCAGAAACCAGGGAAATCTCCTCAGCTCCTGGTCTCTATAGTGCAACTATC
KJ16 mut 4          ATCAGCAGAAACCAGGGAAATCTCCTCAGCTCCTGGTCTCTATAGTGCAACTATC
KJ16 mut 7          ATCAGCAGAAACCAGGGAAATCTCCTCAGCTCCTGGTCTCTATAGTGCAACTATC ----------
KJ16 wild-type      TTGGCAGATGGGGTCCCATCAAGGTTCAGTGGCAGTAGATCTGGCACACAGTA
KJ16 mut 4          TTGGCAGATGGGGTCCCATCAAGGTTCAGTGGCAGTAGATCTGGCACACAGTA
KJ16 mut 7          TTGGCAGATGGGGTCCCATCAAGGTTCAGTGGCAGTAAATCTGGCACACAGTA
                                                         ↑
                                                        R66K
```

FIG. 18-1

```
KJ16 wild-type    TTCTCTTAAGATCAACAGACTACAGGTTGAAGATATTGGAACCTATTACTGTC
KJ16 mut 4        TTCTCTTAAGATCAACAGACTACAGGTTGAAGATATTGGAACCTATTACTGTC
KJ16 mut 7        TTCTCTTAAGATCAACAGACTACAGGTTGAAGATATTGGAACCTATTACTGTC ----------CDR3----------
KJ16 wild-type    TACAGGTTTCTAGTTCTCCCGTACACGTTTGGAGCTGGCACCAAGCTGGAGCTC
KJ16 mut 4        TACAGGTTTCTAGTTCTCCCGTACACGTTTGGAGCTGGCACCAAGCTGGAGCTC
KJ16 mut 7        TACAGGTTTCTAGTTCTCCCGTACACGTTTGGAGCTGGCACCAAGCTGGAGCTC
                                                      ˅
                                                      ˅
                                                      ˅
                  V_H          ------------c-myc------------
KJ16 wild-type    AAACGG../..TCCTCAGAACAAAAGCTTATTTCCGAAGAAGATTTGTAGTAA
KJ16 mut 4        AAACGG../..TCCTCAGAACAACAAGAGCTTATTTCCGAAGAAGATTTGTAGTAA
KJ16 mut 7        AAACGG../..TCCTCAGAACAAAAGCTTATTTCCGAAGAAGATTTGTAGTAA
                                          ↑
                                        K258E
```

FIG. 18-2 vβ8.2
GACGTCGCAG TCACCCAAAG CCCAAGAAAC AAGGTGGCAG TAACAGGAGG AAAGGTGACA
                                                         Gly17ΔGlu
------cdr1------
TTGAGCTGTA ATCAGACTAA TAACCACAAC AACATGTACT GGTATCGGCA GGACACGGGG
                     ------cdr2------
CATGGGCTGA GGCTGATCCA TTATTCATAT GGTGCTGGCA GCACTGAGAA AGGAGATATC
                                           ------hv4------
CCTGATGGAT ACAAGGCCTC CAGACCAAGC CAAGAGAACT TCTCCCTCAT TCTGGAGTTG
                                                  ------cdr3------
GCTACCCCCT CTCAGACATC AGTGTACTTC TGTGCCAGCG GTGGGGGGGG CACCTTGTAC
                                    linker                 Vα3.1
TTTGGTGCGG GCACCCGACT ATCGGTGCTA TCCTCCGCGG ATGATGCTAA GAAGGATGCT

GCTAAGAAGG ATGATGCTAA GAAAGATGAT GCTAAGAAAG ATGCACACAG AGTGACACAG

CCCGATGCTC GCGTCACTGT CTCTGAAGGA GCCTCTCTGC AGCTGAGATG CAAGTATTCC

FIG. 21-1

```
------cdr1-------
TACTCTGCGA CACCTTATCT GTTCTGGTAT GTCCAGTACC CGCGGCAGGG GCTGCAGCTG
                      -------cdr2--------                  Leu43ΔPro
CTCCTCAAGT ACTATTCCGG AGACCCAGTG GTTCAAGGAG TGAATGGCTT TGAGGCTGAG
-------hv4--------
TTCAGCAAGA GCAACTCTTC CTTCCACCTG CGGAAAGCCT CCGTGCACTG GAGCGACTCG
                                  -------cdr3-------
GCTGTGTACT TCTGTGCTGT GAGCGGGCTTT GCAAGTGCGC TGACATTTGG ATCTGGCACA
                                              Leu104ΔPro
AAAGTCATTG TTCTACCATA CATCTAG    +    6-His
```

FIG. 21-2

YEAST CELL SURFACE DISPLAY OF PROTEINS AND USES THEREOF

CROSS-RELATED TO RELATED APPLICATIONS

This application is a continuation-in-part of Ser. No. 09/009,388, filed Jan. 20, 1998, which is a continuation-in-part of 08/866,398, filed May 30, 1997, abandoned, which claims benefit of priority of provisional application No. 60/018,741, filed May 31, 1996, now abandoned.

FEDERAL FUNDING LEGEND

This invention was produced in part using funds obtained through grant R01AI35990 and R01GM55767 from the National Institutes of Health grant. Consequently, the federal government has certain rights in this invention.

BACKGROUND OF THE INVENTION

1. Field of the Invention

The present invention relates generally to the fields of immunology and protein chemistry. More specifically, the present invention relates to the display of peptides and proteins on the yeast cell surface for selection of sequences with desirable binding properties from combinatorial libraries.

2. Description of the Related Art

Antibody combining site structure can be predicted with reasonable accuracy from polypeptide sequence data, but the ability to rationally engineer improvements in binding affinity and specificity has proven more elusive, despite some successes (e.g., Roberts et al., '87; Riechmann et al., '92). As a result, mutagenesis and screening of libraries currently represents the most fruitful approach to directed affinity maturation of antibodies. Combinatorial library screening and selection methods have become a common tool for altering the recognition properties of proteins (Ellman et al., 1997, Phizicky & Fields, 1995). In particular, the construction and screening of antibody immune repertoires in vitro promises improved control over the strength and specificity of antibody-antigen interactions.

The most widespread technique is phage display, whereby the protein of interest is expressed as a polypeptide fusion to a bacteriophage coat protein and subsequently screened by binding to immobilized or soluble biotinylated ligand (e.g., Huse et al., '89; Clackson et al., '91; Marks et al., '92). Fusions are made most commonly to a minor coat protein, called the gene III protein (pIII), which is present in three to five copies at the tip of the phage. A phage constructed in this way can be considered a compact genetic "unit", possessing both the phenotype (binding activity of the displayed antibody) and genotype (the gene coding for that antibody) in one package. Phage display has been successfully applied to antibodies, DNA binding proteins, protease inhibitors, short peptides, and enzymes (Choo & Klug, 1995, Hoogenboom, 1997, Ladner, 1995, Lowman et al., 1991, Markland et al., 1996, Matthews & Wells, 1993, Wang et al., 1996).

Antibodies possessing desirable binding properties are selected by binding to immobilized antigen in a process called "panning." Phage bearing nonspecific antibodies are removed by washing, and then the bound phage are eluted and amplified by infection of *E. coli*. This approach has been applied to generate antibodies against many antigens, including: hepatitis B surface antigen (Zebedee et al., '92); polysaccharides (Deng et al., '94), insulin-like growth factor 1 (Garrard & Henner, '93), 2-phenyloxazol-5-one (Riechmann & Weill, '93), and 4-hydroxy-5-iodo-3-nitro-phenacetyl-(NIP)-caproic acid (Hawkins et al., '92).

Nevertheless, phage display possesses several shortcomings. Although panning of antibody phage display libraries is a powerful technology, it possesses several intrinsic difficulties that limit its wide-spread successful application. For example, some eucaryotic secreted proteins and cell surface proteins require post-translational modifications such as glycosylation or extensive disulfide isomerization which are unavailable in bacterial cells. Furthermore, the nature of phage display precludes quantitative and direct discrimination of ligand binding parameters. For example, very high affinity antibodies ($K_D \leq 1$ nM) are difficult to isolate by panning, since the elution conditions required to break a very strong antibody-antigen interaction are generally harsh enough (e.g., low pH, high salt) to denature the phage particle sufficiently to render it non-infective. Additionally, the requirement for physical immobilization of an antigen to a solid surface produces many artifactual difficulties. For example, high antigen surface density introduces avidity effects which mask true affinity. Also, physical tethering reduces the translational and rotational entropy of the antigen, resulting in a smaller DS upon antibody binding and a resultant overestimate of binding affinity relative to that for soluble antigen and large effects from variability in mixing and washing procedures lead to difficulties with reproducibility. Furthermore, the presence of only one to a few antibodies per phage particle introduces substantial stochastic variation, and discrimination between antibodies of similar affinity becomes impossible. For example, affinity differences of 6-fold or greater are often required for efficient discrimination (Riechmann & Weill, '93). Finally, populations can be overtaken by more rapidly growing wildtype phage. In particular, since pIII is involved directly in the phage life cycle, the presence of some antibodies or bound antigens will prevent or retard amplification of the associated phage.

Several bacterial cell surface display methods have been developed (Francisco, et al., '93, Georgiou et al., 1997). However, use of a procaryotic expression system occasionally introduces unpredictable expression biases (Knappik & Pluckthun, 1995, Ulrich et al., 1995, Walker & Gilbert, 1994) and bacterial capsular polysaccharide layers present a diffusion barrier that restricts such systems to small molecule ligands (Roberts, 1996). *E. coli* possesses a lipopolysaccharide layer or capsule that may interfere sterically with macromolecular binding reactions. In fact, a presumed physiological function of the bacterial capsule is restriction of macromolecular diffusion to the cell membrane, in order to shield the cell from the immune system (DiRienzo et al., '78). Since the periplasm of *E. coli* has not evolved as a compartment for the folding and assembly of antibody fragments, expression of antibodies in *E. coli* has typically been very clone dependent, with some clones expressing well and others not at all. Such variability introduces concerns about equivalent representation of all possible sequences in an antibody library expressed on the surface of *E. coli*.

The discovery of novel therapeutics would be facilitated by the development of yeast selection systems. The structural similarities between B-cells displaying antibodies and yeast cells displaying antibodies provide a closer analogy to in vivo affinity maturation than is available with filamentous phage. Moreover, the ease of growth culture and facility of genetic manipulation available with yeast will enable large populations to be mutagenized and screened rapidly. By contrast with conditions in the mammalian body, the physicochemical conditions of binding and selection can be altered for a yeast culture within a broad range of pH, temperature, and ionic strength to provide additional degrees of freedom in antibody engineering experiments. The development of a yeast surface display system for screening combinatorial antibody libraries and a screen based on antibody-antigen dissociation kinetics has been described herein.

The potential applications of engineering monoclonal antibodies for the diagnosis and treatment of human disease are far-reaching (e.g., Zaccolo & Malavasi, '93; Serafini, '93). Applications to cancer therapy (Hand et al., '94; Goldenberg, '93; Yarmush et al., '93) and tumor imaging in particular (Fischman et al., '93; Goldenberg & Sharkey, '93; McKearn, '93) have been pursued actively. Antibody therapies for Gram-negative sepsis still hold promise despite discouraging preliminary results (Baumgartner & Glauser, '93). In vitro applications to immunohistochemistry (Mietlinen, '93), immunoassay (Kricka, '93; Ishikawa et al., '93), and immunoaffinity chromatography (Yarmush et al., '92) are already well-developed.

For each of these applications, antibodies with high affinity (i.e., $K_D \leq 10$ nM) and high specificity are desirable. Anecdotal evidence, as well as the a priori considerations discussed previously, suggest that phage display or bacterial display systems are unlikely to consistently produce antibodies of sub-nanomolar affinity. To date, yeast display will fill this gap and as such should be a key technology of tremendous commercial and medical significance.

The importance of T cell receptors to cell-mediated immunity has been known since the 1980's, but no method for engineering higher affinity T cell receptors has been developed. Although several groups have produced single-chain T cell receptor constructs, these expression systems have allowed biochemical analysis of T cell receptor binding, but have not enabled library methods for altering those binding properties in a directed fashion. The T-cell receptor has been particularly difficult to produce in soluble form (Kranz, 1982, Novotny et al., 1991, Ward, 1991). In its endogenous form it is a heterodimeric ($\alpha\beta$) membrane protein that associates non-covalently with subunits of the CD3 complex on the surface of T-lymphocytes. The extracellular $\alpha$ and $\beta$ domains are composed of both constant regions (C$\alpha$ and C$\beta$), and variable regions (V$\alpha$ and V$\beta$) which directly function in binding of a peptide/MHC antigen. Several different methods for production have been developed: secretion of V$\alpha$V$\beta$ from E. coli (Ward, 1991), production of chimeric molecules in myeloma cells consisting of V$\alpha$C$\alpha$ V$\beta$C$\beta$ fused to the constant regions of immunoglobulin k light chain (Necker et al., 1991), production of V$\alpha$C$\alpha$ V$\beta$C$\beta$ in thymoma cells by cleavage from a fusion with cell surface lipids (Slanetz et al., 1991), cleavage of the rat basophilic leukemia cell line produced V$\alpha$C$\alpha$ V$\beta$C$\beta$-z complex before the transmembrane region with thrombin digestion (Engel et al., 1992), production of V$\alpha$C$\alpha$ V$\beta$C$\beta$ in baculovirus infected insect cells with (Chang et al., 1994) and without (Kappler et al., 1994) leucine zipper association, and secretion of immunoglobulin $C_H$-gd TCR chimeras from COS cells (Eilat et al., 1992). Smaller single-chain TCR fragments (scTCR) analogous to single-chain antibody fragments which contain the minimum binding subunit of the full TCR have been constructed and produced in E. coli refolded from inclusion bodies (Soo Hoo et al., 1992) or folded in the periplasm at levels of 0.5–1.0 mg/L (Wulfing et al., 1994, Novotny et al., 1991)

The prior art is deficient in the lack of effective means of displaying cell surface peptides and proteins for selection of sequences with desirable binding properties. The prior art is also deficient in the lack of effective means of engineering the T cell receptor for improved binding properties. More specifically, no technology has been available to engineer soluble T cell receptors to produce therapeutic intervention of cell-mediated immunity. The present invention fulfills this longstanding need and desire in the art.

SUMMARY OF THE INVENTION

In one embodiment of the present invention, there is provided a genetic method for tethering polypeptides to the yeast cell wall in a form accessible for protein-protein binding. Combining this method with fluorescence-activated cell sorting provides a means of selecting proteins with increased or decreased affinity for another molecule, altered specificity, or conditional binding.

In another embodiment of the present invention, there is provided a method of genetic fusion of a polypeptide of interest to the C-terminus of the yeast Aga2p cell wall protein. Under mating conditions, the outer wall of each yeast cell contains about $10^4$ protein molecules called agglutinins. The agglutinins serve as specific contacts to mediate adhesion of yeast cells of opposite mating type during mating. In effect, yeast has evolved a platform for protein-protein binding without steric hindrance from cell wall components. By attaching an antibody to the agglutinin, one effectively can mimic the cell surface display of antibodies by B cells in the immune system.

In yet another embodiment of the present invention, there is provided a method of fusing a nine residue epitope (HA) tag to the C-terminus of the AGA2 protein. This short peptide is accessible on the cell surface to an antibody in solution without any fixation or digestion of the cells, and can be detected by flow cytometry or fluorescence microscopy. Thus, yeast can be used to display peptides.

In yet another embodiment of the present invention, there is provided a method of fusing an scFv fragment of the 4-4-20 monoclonal antibody to the C-terminus of the AGA2 protein. This fragment is accessible on the cell surface and binds the fluorescein antigen without any fixation or digestion of the cells, and can be detected by flow cytometry or fluorescence microscopy. Thus, yeast can be used to display antibody fragments.

One aspect of the present invention provides a method for selecting proteins with desirable binding properties comprising: transforming yeast cells with a vector expressing a protein to be tested fused at its N-terminus to a yeast cell wall binding protein; labeling the yeast cells with a first label, wherein the first label associates with yeast expressing the protein to be tested and does not associate with yeast which do not express the protein to be tested; selecting for the yeast cells with which said first label is associated; and quantitating said first label, wherein a high occurrence of the first label indicates the protein to be tested has desirable binding properties and wherein a low occurrence of the first label indicates the protein to be tested does not have desirable binding properties.

A preferred embodiment of the present invention further includes the steps of: labeling the yeast cells with a second label, wherein the second label. associates with yeast expressing an epitope tag fused to the protein to be tested and encoded by said vector and does not associate with yeast which do not express the epitope tag encoded by said vector; quantitating said second label, wherein an occurrence of the second label indicates a number of expressed copies of the epitope-tagged protein to be tested on the yeast cell surface;

and comparing said quantitation of the first label to said quantitation of the second label to determine the occurrence of the first label normalized for the occurrence of the second label, wherein a high occurrence of the first label relative to the occurrence of the second label indicates the protein to be tested has desirable binding properties.

Another preferred embodiment of the present invention includes the steps of: labeling the yeast cells with a third label that competes with said first label for binding to the protein to be tested; labeling the yeast cells with said first label; quantitating said first label; labeling the yeast cells with said second label; quantitating said second label; and comparing said quantitation of the first label to said quantitation of the second label to determine the occurrence of the first label normalized for the occurrence of the second label, wherein a low occurrence of the first label relative to the occurrence of the second label indicates the protein to be tested has desirable binding properties.

In one embodiment of the present invention, the first label is a fluorescent label attached to a ligand and the second label is a fluorescent label attached to an antibody. When the labels are fluorescent, the quantitation step is performed by flow cytometry or confocal fluorescence microscopy.

Another aspect of the present invention provides a vector for performing the method of the present invention, comprising a cell wall binding protein fused to an N-terminus of a protein of interest. Preferred embodiments of this aspect of the present invention include means for expressing a polypeptide epitope tag fused to said protein of interest in said yeast cells. A more preferred embodiment provides that the cell wall binding protein is the binding subunit of a yeast agglutinin protein, even more preferably yeast agglutinin binding subunit is Aga2p.

Another preferred embodiment of the present aspect of the invention provides that the epitope tag amino acid sequence is selected from the group of YPYDVPDYA (HA) (SEQ ID No. 1), EQKLISEEDL (c-myc) (SEQ ID No. 2), DTYRYI (SEQ ID No. 3), TIDFYLK (SEQ ID No. 4), EEEEYMPME (SEQ ID No. 5), KPPTPPPEPET (SEQ ID No. 6), HHHHHH (SEQ ID No. 7), RYIRS (SEQ ID No. 8), or DYKDDDDK (SEQ ID No. 9), and that the N-terminus of said protein of interest is fused to a C-terminus of said cell wall binding protein.

In yet another preferred embodiment of the present invention, there is provided a method for selecting proteins with enhanced phenotypic properties relative to those of the wild-type protein, comprising the steps of: transforming yeast cells with a vector expressing a protein to be tested fused to a yeast cell wall protein, wherein mutagenesis is used to a generate a variegated population of mutants of the protein to be tested; labeling the yeast cells with a first label, wherein the first label associates with yeast expressing the protein to be tested and does not associate with yeast which do not express the protein to be tested; isolating the yeast cells with which the first label is associated; and analyzing and comparing the properties of the mutant protein expressed by yeast with properties of the wild-type protein, wherein yeast cells exhibiting mutant proteins with enhanced properties over the wild-type protein are selected. As described above, a second and/or third label may be employed with this embodiment, and selection of mutated proteins of interest with enhanced phenotypic properties may involve iterative cycles of the enrichment and labeling steps.

In preferred embodiments, the yeast cell wall protein is an agglutinin; the protein to be tested is fused by its N terminus to the C terminus of a binding subunit an agglutinin; the yeast strain is of a genus selected from the group consisting of Saccharomyces, Pichia, Hansenula, Schizosaccharomyces, Kluyveromyces, Yarrowia, and Candida; the protein to be tested is an antibody, Fab, Fv, or scFv antibody fragment, more prefereably the protein to be tested is the ligand binding domain of a cell surface receptor, even more prefereably the cell surface receptor is a T cell receptor.

An object of the present invention is to provide a method to select for mutant proteins exhibiting enhanced phenotypic properties selected from the group consisting of surface expression, stability, binding constant, dissociation constant, level of secretion, and solubility, wherein the mutants of the protein to be tested may contain single mutations or multiple mutations.

In yet another embodiment, a second label may be used to quantitatively determine cell surface expression levels, which may be used as an assay to select for other desirable phenotypic properties, such as intracellular expression, stability, binding constant, dissociation constant, level of secretion, and solubility.

In yet another embodiment, the mutant proteins selected by the methods of the present invention may be further characterized by cloning the gene encoding the selected mutant proteins into a vector adapted for expression in a eukaryote; and expressing the mutant protein in the eukaryote, wherein the enhanced properties of the mutant protein are confirmed by comparing the phenotypic properties of the enhanced properties of the mutant protein with the properties of the wild-type protein. Preferably, the eukaryote is selected from the group consisting of mammalian, insect, or yeast. Because the phenotype of the selected mutant is an inherent property of the "new" (i.e. mutated) protein, this approach is also applicable to expressing the mutant in other non-eukaryotic expression systems.

Yeast surface display and sorting by flow cytometry have been used to isolate mutants of a scFv that is specific for the Vb8 region of the T cell receptor. Selection was based on equilibrium binding by two fluorescently-labeled probes, a soluble Vb8 domain and an antibody to the c-myc epitope tag present at the carboxy-terminus of the scFv. The mutants that were selected in this screen included a scFv with three-fold increased affinity for the Vb8 and scFv clones that were bound with reduced affinities by the anti-c-myc antibody. The latter finding indicates that the yeast display system may be used to map conformational epitopes, which can not be revealed by standard peptide screens. Equilibrium antigen binding constants were estimated within the surface display format, allowing screening of isolated mutants without necessitating subcloning and soluble expression. Only a relatively small library of yeast cells ($3 \times 10^5$) displaying randomly mutagenized scFv was screened to identify these mutants, indicating that this system will provide a powerful tool for engineering the binding properties of eucaryotic secreted and cell surface proteins.

Another preferred embodiment of the present aspect of the invention provides a method for displaying proteins that are not displayed as their normal ("wild type") sequence. In the example shown, the T cell receptor for antigen was not expressed as its "wild type" sequence. However, after random mutagenesis and selection by flow cytometry with appropriate conformationally-specific antibodies, the mutant receptors were expressed on the yeast cell surface. This strategy will allow the discovery of novel T cell receptors and it provides a method for the display of virtually any polypeptide. Thus, the present invention also provides a method for selecting proteins for displayability on a yeast cell surface, comprising the step of: transforming yeast cells with a vector expressing a protein to be tested fused to a yeast cell wall protein, wherein mutagenesis is used to a generate a variegated population of mutants of the protein to be tested; labeling said yeast cells with a first label, wherein said first label associates with yeast expressing said protein to be tested and does not associate with yeast which do not express said protein to be tested; isolating said yeast cells with which said first label is associated, by quantitating said first label, wherein a high occurrence of said first label indicates said protein to be tested has desirable display properties and wherein a low occurrence of said first label indicates said protein to be tested does not have desirable display properties. Preferably, the protein tested is an antibody, Fab, Fv, or scFv antibody fragment or the ligand binding domain of a cell surface receptor. A representative example of a cell surface receptor is a T cell receptor.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows a vector for yeast surface display.

FIG. 7 shows the sequence of the AGA2-HA-4-4-20-c-myc gene cassette (SEQ. ID No.21).

FIG. 8 (Parts A–B) shows confocal microscopic images of yeast displaying scFv. Yeast containing plasmid directing surface expression of the HA peptide (FIG. 8A) or the scFv fusion (FIG. 8B) were labeled with mAb 9E10, followed by a secondary anti-mouse IgG-R-phycoerythrin (PE) conjugate and FITC-dextran. DIC (upper panels), red PE fluorescence (middle panels), and green FITC fluorescence (lower panels) images were collected.

FIG. 16 (Parts A–F) shows the fluorescent labeling distributions for anti-c-myc or scTCR binding of three selected mutants shown in FIG. 4. Three classes of scFv-KJ16/yeast mutants were double-stained with anti-c-myc and biotinylated-scTCR followed by FITC-labeled goat anti-mouse IgG and a streptavidin-phycoerythrin conjugate, then analyzed by flow cytometry as described in FIG. 4. The fluorescent distributions for each scFv-KJ16/yeast mutant (shaded) and wt scFv-KJ16/yeast (unshaded) are shown. FIGS. 16A and 16B, mut4; FIGS. 16C and 16D, mut7; FIGS. 16E and 16F, mut10.

FIG. 18 shows the sequence analysis of wild-type scFv-KJ16 (SEQ. ID No. 22), mut4 (SEQ. ID No. 23), and mut7. Plasmids from wt scFv-KJ16/yeast and two mutants (mut4 and mut7 (SEQ. ID.24)) were recovered by plasmid rescue and transformed into E. coli DH5α competent cells to produce plasmids for sequencing, as described below. Sequence analysis was performed using primers that flank the scFv of the display vector. Mutations are indicated in bold.

FIG. 21 shows the sequence of mutations that lead to the enhanced expression of the cell surface T cell receptor (SEQ. ID No. 25). These included residues 17 of the Vβ, 43 of the Vα, and 104 of the Vα.

DETAILED DESCRIPTION OF THE INVENTION

Figure 1:
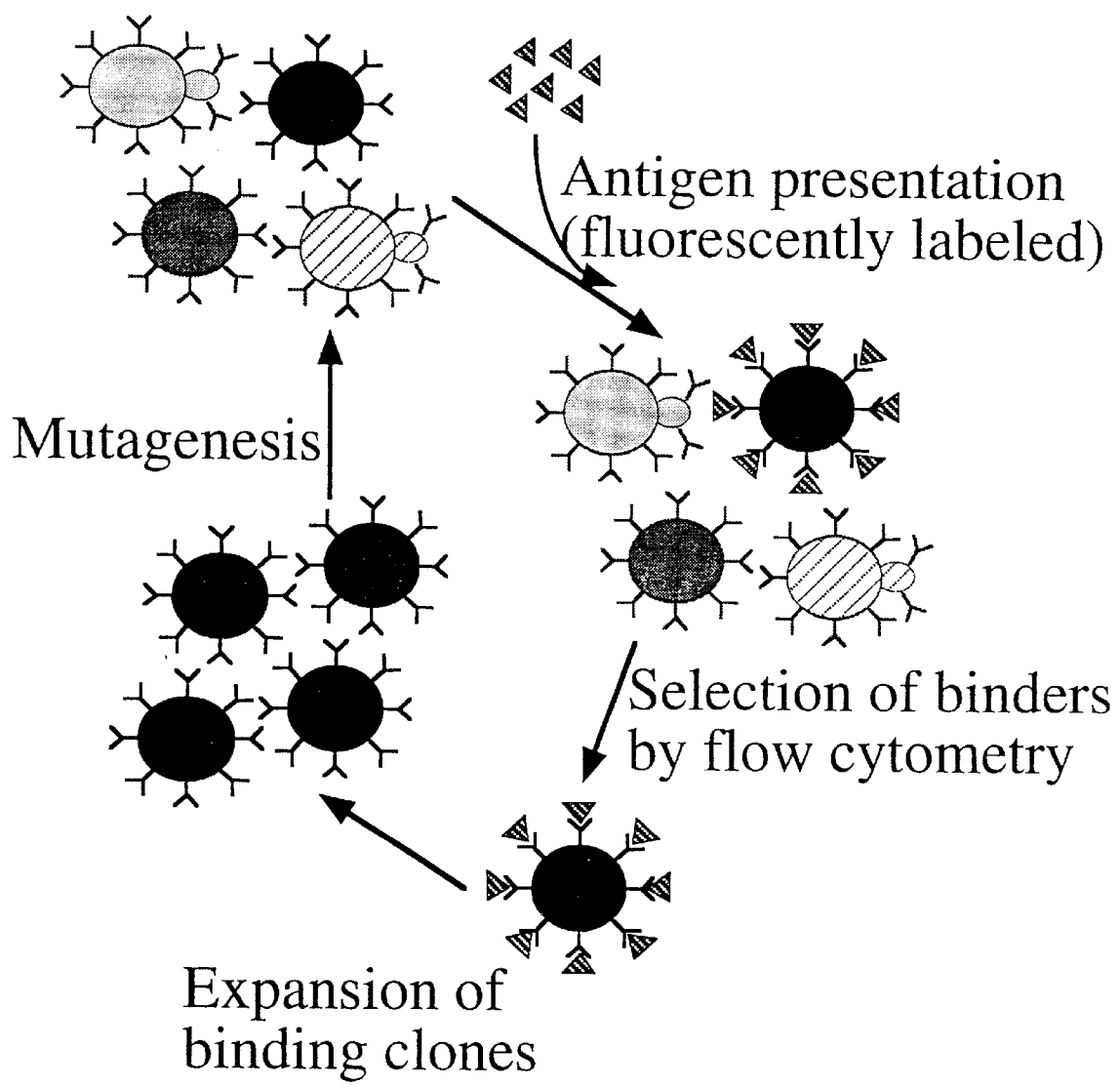
FIG. 1 is a schematic, showing in vitro affinity maturation by yeast display.

As used herein, the term "affinity maturation" shall refer to a process of successive mutation and selection by which antibodies of higher affinity are selected.

As used herein, the term "agglutinin" shall refer to a yeast surface adhesion protein which binds two yeast cells together during mating.

As used herein, the term "antibody" shall refer to a protein produced by mammalian immune systems which binds tightly and specifically to particular molecules.

As used herein, the term "ligand" shall refer to a molecule that is bound specifically by a particular protein.

As used herein, the term "antigen" shall refer to a ligand that is bound specifically by an antibody.

As used herein, the term "Complementarity Determining Region" or "CDR" shall refer to the portion of an antibody which directly contacts the bound antigen.

As used herein, the term "Fluorescence Activated Cell Sorting" or "flow cytometry" shall refer to a method for sorting cell populations on the basis of differential fluorescent labeling.

As used herein, the term "hapten" shall refer to a small antigen which cannot stimulate an immune response without being conjugated to a carrier.

As used herein, the term "single chain antibody" or "SCA" shall refer to a fusion of portions of the heavy and light chains of an antibody which retains a single active binding site. The term scFv is used interchangeably to refer to a single chain antibody.

As used herein, the term "epitope tag" shall refer to a contiguous sequence of amino acids specifically bound by an antibody when fused to another protein.

As used herein, the term "HA" refers to the epitope tag sequence YPYDVPDYA (SEQ ID No. 1).

As used herein, the term "c-myc" refers to the epitope tag sequence EQKLISEEDL (SEQ ID No. 2).

As used herein, the term "scFv 4-4-20" refers to an scFv which binds specifically to fluorescein and fluorescein conjugated to other molecules such as biotin or dextran.

As used herein, the term "AGA2p" refers to the protein product of the yeast AGA2 mating type a agglutinin gene.

The term "displayability" will be used to describe a combination of biophysical characteristics allowing a protein to escape the secretory "quality control" apparatus that retains and degrades misfolded proteins (Hammond & Helenius, 1995.) Proteins displayed on the yeast cell surface must first pass successfully through the quality control step. Protein folding kinetics and thermodynamic stability together are believed to determine the efficiency of escape from the quality control apparatus.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the -10 and -35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "selection gene" refers to a gene that enables the discrimination of cells displaying a required phenotype upon implementation of certain conditions. For example, the growth of bacteria in medium containing antibiotics to select for the bacterial cells containing antibiotic resistance genes.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, the term "reporter gene" refers to a coding sequence attached to heterologous promoter or enhancer elements and whose product is easily and quantifiably assayed when the construct is introduced into tissues or cells.

Transcriptional and translational control sequences are DNA regulatory sequences, such as promoters, enhancers, polyadenylation signals, terminators, and the like, that provide for the expression of a coding sequence in a host cell.

A number of fluorescent materials are known and can be utilized as labels. These include, for example, fluorescein, rhodamine, auramine, Texas Red, AMCA blue, R-phycoerythrin, B-phycoerythrin, and Lucifer Yellow.

A number of polypeptide sequences that can be fused to proteins and bound specifically by antibodies are known and can be utilized as epitope tags. These include, for example, HA (SEQ ID No. 1), c-myc (SEQ ID No. 2), DTYRYI (SEQ ID No. 3), TDFYLK (SEQ ID No. 4), EEEEYMPME (SEQ ID No. 5), KPPTPPPEPET (SEQ ID No. 6), E1HHHHHH (SEQ ID No. 7), RYIRS (SEQ ID No. 8), and DYKDDDDK (SEQ ID No. 9).

Antibodies are protein molecules produced by the human immune system to recognize, bind to, and mediate the clearance of foreign substances from the body. Technologies have been developed to take advantage of antibodies for highly-specific cancer diagnosis and therapy. For example, by tethering radioisotopes or toxins to an antibody which binds to tumor cells, it is possible to deliver a focused dosage of such cell-killing agents to the diseased tissue while leaving surrounding tissue comparatively unharmed. Antibodies are also critical tools in biotechnology, and are used extensively for analytical purposes, e.g., to quantify trace quantities of substances and separations, and to purify desired biological products from complex mixtures.

In these applications, both the strength of the antibody bond with its target (affinity) and the selectivity with which an antibody binds to only its particular target (specificity) are crucial. For this reason, protein engineers seek to alter and improve the binding characteristics of particular antibodies. Rational approaches to antibody structural design have met with limited success, and available methods for random screening possess significant limitations.

The mammalian immune system's approach to the problem of fine tuning antibody affinity is by a process called "affinity maturation," wherein cycles of mutation and evolutionary selection produce antibodies which bind their targets more tightly. The present invention discloses a powerful new system for engineering antibody affinity and specificity, by constructing a microbial analog of the mammalian immune system's B cell repertoire. Antibodies were displayed on the surface of yeast cells by genetic fusion with cell wall proteins. After mutation, variants were selected on the basis of improved binding characteristics with fluorescently labeled targets.

The yeast antibody display method was tested by studying model antibodies whose physical and chemical properties are already well characterized. These methods are then straightforwardly applied to antibodies of practical interest. The genetic malleability of yeast, the ease of growth of this microbe, and the ability to modify antibody binding conditions in the test tube combine to produce unprecedented control over the engineering of antibody affinity and specificity.

The advantage of the library method of the present invention is that it is particularly suited for proteins such as antibodies. The most widely used method currently consists of "panning" for antibodies displayed on the surface of bacteriophage. Yeast display has several advantages over phage display. First, the antibody-antigen bond need not be broken to recover tightly-bound variants. The harsh conditions required for disrupting this bond in prior art methods can reduce infectivity of phage. Secondly, increased library diversity due to decreased clonal deletion is an advantage. It is well known that many antibody structures cannot be correctly processed by the bacterial secretory apparatus. Yeast cells are eucaryotic and possess secretory pathways very similar to mammalian cells. Thirdly, the present invention provides a more accurate and precise determination of antibody-antigen affinity. The presence of $10^4$ molecules per cell eliminates the stochastic variation that results with only a few molecules per phage. Finally, quantitation of fluorescence by flow cytometry provides a continuous measure of surface-bound antigen without a priori knowledge of affinity in by comparison to the binary bound/released dichotomy with panning of phage. Also, bacteria possess a lipopolysaccharide layer which acts as a macromolecular permeability barrier preventing antibody or protein access to displayed molecules.

The present invention discloses a surface display system for the in vitro expression and selection of peptide and protein libraries on yeast. A nine residue peptide epitope (HA) has been fused to the binding subunit of a yeast cell wall protein (AGA2), followed by the 4-4-20 antifluorescein single-chain Fv. Selection was performed by flow cytometry on mixtures of cells with and without the displayed fusion. 600-fold enrichments were achieved in one pass of sorting. The system of the present invention illustrates a process for the in vitro affinity maturation of antibodies as well as a process for the directed evolution of other proteins and peptides, with the advantages of (i) a double-label flow cytometry selection scheme allowing finer affinity discrimination than panning; (ii) as many as $10^4$ copies of the displayed sequence per cell, eliminating stochastic variations in the selection; and (iii) library expression in yeast, with an altered or potentially improved expression bias which could yield clones that would be deleted from a library expressed in E. coli.

One object of the present invention is the engineering of antibodies for improved affinity and specificity. Toward this end, antibody-hapten binding was studied via mutagenesis and screening of antibodies expressed on the external cell wall of the yeast Saccharomyces cerevisiae. As an experimentally facile and genetically pliable eucaryote, yeast presents significant advantages over filamentous phage display as a platform for antibody expression and engineering. In essence, a microbial analog of the mammalian immune system B-cell repertoire was constructed in vitro, allowing antibody affinity maturation to be performed under strictly controlled conditions of mutagenesis and selection. As a result, antibodies of significantly improved affinity and specificity were attainable.

One aspect of the present invention provides a method for selecting proteins with desirable binding properties comprising: transforming yeast cells with a vector expressing a protein to be tested fused at its N-terminus to a yeast cell wall binding protein; labeling the yeast cells with a first label, wherein the first label associates with yeast expressing the protein to be tested and does not associate with yeast which do not express the protein to be tested; selecting for the yeast cells with which said first label is associated; quantitating said first label, wherein a high occurrence of the first label indicates the protein to be tested has desirable binding properties and wherein a low occurrence of the first label indicates the protein to be tested does not have desirable binding properties.

A preferred embodiment of the present invention further includes the steps of: labeling the yeast cells with a second label, wherein the second label associates with yeast expressing an epitope tag fused to the protein to be tested and encoded by said vector and does not associate with yeast which do not express the epitope tag encoded by said vector; quantitating said second label, wherein an occurrence of the second label indicates a number of expressed copies of the epitope tagged protein to be tested on the yeast cell surface; and comparing said quantitation of the first label to said quantitation of the second label to determine the occurrence of the first label normalized for the occurrence of the second label, wherein a high occurrence of the first label relative to the occurrence of the second label indicates the protein to be tested has desirable binding properties.

Another preferred embodiment of the present invention includes the steps of: labeling the yeast cells with a third label that competes with said first label for binding to the protein to be tested; labeling the yeast cells with said first label; quantitating said first label; labeling the yeast cells with said second label; quantitating said second label; and comparing said quantitation of the first label to said quantitation of the second label to determine the occurrence of the first label normalized for the occurrence of the second label, wherein a low occurrence of the first label relative to the occurrence of the second label indicates the protein to be tested has desirable binding properties.

Another aspect of the present invention provides a vector for performing the method of the present invention, comprising a cell wall binding protein fused to an N-terminus of a protein of interest. Preferred embodiments of this aspect of the present invention include means for expressing a polypeptide epitope tag in said yeast cells. A more preferred embodiment provides that the cell wall binding protein is a yeast agglutinin protein binding subunit, even more preferably yeast agglutinin protein is Aga2p.

The following examples are given for the purpose of illustrating various embodiments of the invention and are not meant to limit the present invention in any fashion.

EXAMPLE 1

Media/Buffers

The following media/buffers were used herein:

E. coli

LB media (1X)

Bacto tryptone (Difco, Detroit, Mich.): 10.0 g; Bacto yeast extract (Difco): 5.0 g; NaCl:-10.0 g. Make up to 1 L, autoclave. For plates, add 15g/L agar and autoclave.

Ampicillin Stock 25 mg/ml of sodium salt of ampicillin in water. Filter sterilize and store in aliquots of 4 mls at −20° C. Working [ ]=35–50 mg/ml; 4 ml of aliquot in 1 L →100 mg/ml; 2 ml of aliquot in 1 L →50 mg/ml. Add to autoclaved LB only after it has cooled to ~55° C.

SOC Media (100 mL)

2% Bacto tryptone: 2.0 g; 0.5% Yeast Extract (Difco): 0.5 g; 10 mM NaCl: 0.2 ml 5 M; 10 mM $MgCl_2$: 1.0 ml 1 M; 10 mM $MgSO_4$: 1.0 ml 1 M; 20 mM Dextrose: 0.36 g. Autoclave or filter sterilize.

Yeast

| Synthetic Minimal + Casamino acids (SD-CAA) 500 mL | |
|---|---|
| Dextrose (Glucose) | 10.00 g |
| Yeast Nitrogen Base w/o Amino Acids (Difco) | 3.35 g |
| $Na_2HPO_4.7H_2O$ | 5.1 g |
| $NaH_2PO_4.H_2O$ | 4.28 g |
| Casamino Acids (Trp-, Ura-) (Difco) | 2.5 g |

Add $dH_2O$ to final volume. Filter sterilize and refrigerate. For plates, dissolve sodium phosphates and sorbitol to 1 M final concentration in 400 ml $dH_2O$. Add 7.5 g agar and autoclave. Dissolve dextrose, $N_2$ base, and amino acids in 100 ml $dH_2O$ and filter sterilize. Add the filtered reagents after the autoclaved salts have cooled enough to touch.

| SG-CAA (Induction Medium) 500 mL | |
| --- | --- |
| Galactose | 10.00 g |
| Yeast Nitrogen Base w/o Amino Acids (Difco) | 3.35 g |
| Na$_2$HPO$_4$.7H$_2$O | 5.1 g |
| NaH$_2$PO$_4$.H$_2$O | 4.28 g |
| Casamino Acids (Trp-, Ura-) (Difco) | 2.5 g |

Add dH$_2$O to final volume. Filter sterilize and refrigerate.
Rich (YPD) (1000 mL)
  Yeast extract: 10 g; Peptone (Difco): 20 g; Dextrose: 20 g. Add dH$_2$O to 1 L. Autoclave.
TAE (Tris-Acetate)
  Working solution: 0.04 M Tris-acetate and 0.001 M EDTA

| Stock (50X) | in 1 L |
| --- | --- |
| Tris base | 242 g |
| glacial acetic acid | 57.1 ml |
| 0.5 M EDTA (pH 8.0) | 100 ml |

TBE (Tris-Borate)
  Working solution: 0.09 M Tris-borate and 0.001 M EDTA

| Stock (5X) | in 1 L |
| --- | --- |
| Tris base | 54 g |
| boric acid | 27.5 g |
| 0.5 M EDTA (pH 8.0) | 20.0 ml |

Stop Buffer 10X (Restriction)
  50% v/v glycerol; 0.1 M EDTA (pH 7.5); 1% w/v SDS; 0.1% w/v bromophenol blue. Combine all components except for the dye and pH to 7.5 before dye addition.
Staining—Ethidium Bromide
  0.5 mg/ml in water; Stock: 10 mg/ml. Dilutions of Stock: 1/10 in TBE. Add 100 ml dilution in 100 ml buffer.
TBS Working Solution
  10 mM Tris-HCl, 140 mM NaCl and 5 mM EDTA. Filter sterilize.

EXAMPLE 2
Protocol: Replica Plating
  1. Choose a material suitable for colony lifts, making sure it is washed, dried and sterile.
  2. Mark the bottom of each fresh replica plate with an arrow to line up the plate. Also mark the starting plate.
  3. Take the top off the starting plate, turn it upside down and line up the arrow on the bottom with the mark on the colony lift material. Lay the plate down onto the surface of the material and gently put pressure on the entire plate. Make sure the plate doesn't move around after it has touched the material. Remove the plate and replace the lid. Portions of the colonies that transferred to the material can be seen.
  4. Repeat this procedure with one of the fresh replica plates. Make sure the arrow lines up with the mark also to make a n exact replica. Hold up to the light to see the tiny colonies that transferred. 5. Repeat the entire procedure for each replica plate to be made. 6. Incubate the replica plates at the appropriate conditions for selective growth. Colonies will usually grow up within a day or so.

EXAMPLE 3
Protocol: Electrotransformation of Yeast
Cell Preparation:
  1. Inoculate 50 ml of YPD with an overnight culture to an OD of 0.1.
  2. Grow cells at 30° C. with vigorous shaking to an OD$_{600}$ of 1.3 to 1.5 (approximately 6 hours).
  3. Harvest in cold rotor at 3500 rpm for 5 minutes at 4° C. Discard supernatant.
  4. Thoroughly wash the cells by resuspending in 50 ml cold sterile water. Centrifuge as above and discard supernatant.
  5. Repeat step 4 with 25 ml cold water.
  6. Resuspend in 2 ml of ice-cold sterile 1 M sorbitol. Centrifuge as above and discard supernatant.
  7. Resuspend in 50 ml ice-cold 1 M sorbitol. Final volume of cells is about 150 ml (enough for 3 transformations).
Electrotransformation
  1. Place 0.2 cm cuvettes and white slide chamber on ice.
  2. In an eppendorf tube, add 50 ml of yeast suspension and gently mix in <5 ml (0.1 mg) of plasmid DNA in TE. Make sure to add DNA to yeast already in eppendorf. Place on ice for 5 minutes (This time frame is pretty critical).
  3. Set GENE PULSER at 1.5 kV and 25 mF. Set the Pulse Controller to 200 W. The time constant for this pulse should be 4.5 to 5.0 msec.
  4. Transfer 40 ml of cell/DNA mixture to pre-chilled electroporation cuvette. Tap contents to bottom, making sure the sample is in contact with both aluminum sides of the cuvette. Place the cuvette in chilled safety chamber slide. Push slide into the chamber until the cuvette makes contact with the electrodes in the base of the chamber.
  5. Apply one pulse at the settings above.
  6. Remove the slide with the cuvette, and immediately add 1 ml of cold 1 M sorbitol to the cuvette. Mix gently and return cuvette to ice. Spread 200 ml onto selective plates containing 1 M sorbitol.

EXAMPLE 4
Protocol: *E. Coli* Transformation
  1. Thaw aliquot of competent subcloning efficiency HB 101 (−70° C. storage) on ice, keeping all reagents on ice. Use DH5α cells for lac z complementation; DM-1 for non-methylation.
  2. Dispense 50 ml HBIOI to required # of eppendorf tubes, one for each DNA sample, one for pBR322 (positive control) (pUC19 for DH5a and DM-1), one for no DNA (negative control).
  3. Aliquot unused cells into 50 mL portions and refreeze in a dry ice/EtOH bath; store at −70° C.
  4. Add 1 ml DNA (1 mg) to eppendorfs (1 ml of pBR322 or pUC19), tap tubes to mix, then incubate on ice for 30 min. For ligations, use 1–2 ml of ligation mixture (too much sours the transformation).
  5. Heat shock at 37° C. for 20 seconds. (45 sec at 42° C. for DM-1 cells).
  6. Place on ice for 2 minutes, then add 0.95 mL of room temp SOC media. Incubate at 37° C. for 1 hour in bath (shaking optional) or on shaker in 37° C. room.
  7. Plate 100–200 mL of cells onto LB, 100 mg/mL Ampicillin, and incubate overnight at 37° C.

EXAMPLE 5
Protocol: GELase® DNA Purification
  Wizard® PCR prep (Promega; Madison, Wis.) is an alternative protocol for DNA purification from a gel. GELase® is recommended if the Wizard® prep yield is low. Low yields happen if the desired fragments are less than 200 kb or more than 5 kb long.

1. Separate DNA fragments on a 1% low melting agarose gel in fresh 1× TAE buffer.

2. Stain the gel with ethidium bromide in water. Using the hand-held UV lamp, cut out the fragments of interest with a new razor blade.

3. Place the gel slice in a pre-weighed eppendorf tube. Weigh both again to determine weight of gel slice. If the gel slice weight is more than 300 mg, split samples into two tubes after step 6.

4. Add 2 ml of 50× GELase® buffer per 100 mg of gel slice.

5. Incubate the tube containing the gel slice at 70° C. until the gel is completely molten. This will take at least 20 minutes. A good technique is to wait 30 minutes, pipette the mixture up and down a couple of times, then wait another 10 minutes. Be sure gel is completely melted.

6. Equilibrate the molten gel at 45° C. for at least 30 minutes.

7. Add 1 U of GELase® per 150 mg of molten agarose. Incubate for 4 hours. For >600 mg add 2 U of GELase®.

8. Add 1 volume (1 volume=mg of gel slice) 5 M ammonium acetate to the solution. If using >300 mg of gel, a larger tube is needed for the ethanol precipitation.

9. Add 2 volumes (1 volume=mg of gel slice+ammonium acetate) of room temperature 100% ethanol and invert several times.

10. Pellet the DNA by centrifuging for at least 30 min at room temperature in 19 RAL. If the DNA concentration is very low, wait for 30 minutes after adding the ethanol and then centrifuge for 30 minutes.

11. Remove supernatant with a pipette and discard.

12. Wash the pellet with room temperature 70% ethanol.

13. Dissolve the DNA in water or TE. DNA can then be stored at −20° C.

EXAMPLE 6

Protocol: Ligation

Materials

T4 DNA ligase and 2× T4 DNA ligase buffer For phosphatasing: Calf intestine phosphatase (CIP) and buffer (if needed). For blunt ending: dNTP mix (0.5 mM). Klenow fragment of *E. coli* DNA polymerase I or T4 DNA polymerase. For linking: Oligonucleotide linkers- 0.2 mM DTT.

1. In a 20 ml reaction mixture, cleave the individual DNA components with appropriate restriction endonuclease. After the reaction is complete, inactivate the enzymes by heating 15 minutes to 65° C. If no further enzymatic treatments are necessary, proceed to step 6.

2. If the 5' phosphates of one of the DNAs are to be removed, add 2 ml of 10× CIP buffer and 1 U CIP; incubate 30 to 60 minutes at 37° C. After the reaction is complete, inactivate CIP by heating 15 minutes to 75° C. If no further enzymatic treatments are necessary, proceed to step 6.

3. For blunt ending, add 1 ml of a solution containing all 4 dNTPs (0.5 mM each) and an appropriate amount of the Klenow fragment of *E. coli* DNA polymerase I or T4 DNA polymerase; carry out the filling in or trimming reaction. After complete, inactivate the enzymes by heating 15 minutes to 75° C. If oligonucleotide linkers are to be added, proceed to step 4. If a DNA fragment containing only one blunt end is desired, cleave the reaction products with an appropriate restriction endonuclease. If no further enzymatic treatments are necessary, proceed to step 6.

4. Add 0.1 to 1.0 mg of an appropriate oligonucleotide linker, 1 ml of 10 mM ATP, 1 ml of 0.2 M DTT, and 20 to 100 cohesive—end units of T4 DNA ligase; incubate overnight at 15° C. Inactivate the ligase by heating 15 minutes to 75° C.

5. Cleave the products from step 4 with the restriction enzyme recognizing the oligonucleotide linker, adjusting the buffer conditions if necessary. If only one of the two ends is to contain a linker, cleave the products with an additional restriction enzyme.

6. Isolate the desired DNA segments by gel electrophoresis, if necessary. Then purify (GeneClean II® or GELase®).

7. Ligation: 9 ml component DNAs (0.1 to 5 mg), 4 ml 5× ligase buffer, 1 mL (cohesive end) T4 DNA ligase (BRL: 1 unit=300 cohesive end units, want 20 to 500 cohesive end units) water to 20 mL. Incubate 1 to 24 hours at 16° C.

8. Introduce 1 ml of the ligated products into competent *E. coli* cells and select for transformants. Then do miniprep and restriction mapping to screen for desired product.

EXAMPLE 7

Cloning:

All transformations were into *E. coli* strain DH5α following the manufacturer's protocol.

PCR

Ampliwax PCR gem-mediated hot start PCR (Perkin-Elmer-Cetus, Norwalk, Conn.)—manufacturer's protocol for thin-walled tubes.

GeneAmp PCR Core Reagents (Perkin-Elmer-Cetus)

DNA Thermal Cycler 480 (Perkin-Elmer-Cetus)

AGA2

Cloned by PCR.

Template for PCR was CEN BANK *S. cerevisiae* genomic library (American Type Culture Collection, Rockville, Md.).

Primers:
5'-ATTAGAATTCCCTACTTCATACATTTTCAA-3' (SEQ ID No. 10) and 5'-ATTACTCGAGCTATTACT GCAGagcgtagtctggaacgtcgtatgggtaAAA AACATACTGTGTGTTTATGGG-3' (SEQ ID No. 11).

Thermal profile:
Denaturation 1 minute at 94° C.
Annealing 2 minutes at 41° C. (first 5 cycles), 2 minutes at 45° C. (25 additional cycles)
Extension 25 seconds at 72° C.
Final polishing step 10 minutes at 72° C.

The PCR product was cloned into plasmid pCR-Script using the pCR-Script SK(+) Cloning Kit (Stratagene, La Jolla, Calif.) following the manufacturer's protocol. The 342 bp AGA2 fragment was excised with EcoRI and XhoI, purified on a 1% agarose gel (protocol 6.1.7.2) and subcloned into pCR-Script containing the CUP1 promoter as a KpnI/EcoRI fragment.

HA Peptide

The HA peptide was inserted by cassette mutagenesis. Complementary oligonucleotide strands encoding the Factor Xa recognition sequence and HA epitope were synthesized with cohesive overhangs allowing ligation to the 3' XhoI site of the AGA2 clone while at the same time destroying this site; a downstream SacI site in pCR-Script annealed and ligated to the CUP1-AGA2 construct in pCR-Script. The insert included a new XhoI site at the 3' end of the HA sequence. CUP1-AGA2-HA was excised as a KpnI/XhoI fragment, purified on a 1% agarose gel, and subcloned into yeast shuttle vector pRS314 (1) already containing the alpha factor terminator sequence, to form surface display vector pCT101. Oligo sequences: 5'-TCGACGATTGAAGGTAGA TACCCATACGACGTTCCAGACTACGCTCTGCAGTAA TAGATTATCCTCGAG CT-3' (SEQ ID No. 12) and 5'-CGAGGATAATCTATTACTGCAGAGCGTAGTCTG GAACGTCGTATGGGTATCTACCTTCAATCG-3' (SEQ ID No. 13).

The GAL promoter was excised from vector YCplac22-GAL. 12 bp palindromic linkers with appropriate cohesive overhangs were first cloned into this vector to alter restriction sites at both ends: EcoRI→KpnI (E/KLINK) and BamHI→EcoRI (B/ELINK). The resulting KpnI/EcoRI fragment was cloned into pCT101 to form vector_pCT201. Oligonucleotide sequences: E/LLINK 5'-AATTGGTACC-3' (SEQ ID No. 14); B/ELINK 5'-GATCGAATTC-3' (SEQ ID No. 15).

The 4-4-20 scFv was amplified by PCR as above:

Template: 4-4-20 in GeneX vector (obtained from D. Kranz, UIUC Dept. of Biochem.)

Primers:
5'-ggttggccaagctagcGACGTCGTTATGACTCAA-3' (SEQ ID No. 16) and 5'-ggccggccaactcgagctattaca agtcttcttcagaaataagcttttgttcTGAGGAGAC GGTGACTGA-3' (SEQ ID No. 17).

Thermal profile:
Denaturation 1 minute at 94° C.
Annealing 2 minutes at 40° C. (first 5 cycles), 2 minutes at 48° C. (30 additional cycles)
Extension 50 sec at 72° C.
Final polishing step 10 minutes at 72° C.

The PCR product was cloned into pCR-Script and subcloned into pCT201 as a NheI/XhoI fragment using methods as above, creating vector pCT202. Vector pCT302 was created by inserting a synthetic oligonucleotide (UIUC Biotechnology Center) encoding a $(Gly_4\text{-}Ser)_3$ linker (SEQ ID No. 20) in frame between the AGA2 and 4-4-20 open reading frames of pCT202.

AGA1

Amplified by PCR as above:

Template: GEN BANK

Primers:
5'-ATTAGAATTCAGCTAAAAAAACCAAAAAAT-3' (SEQ ID No. 18) and 5'-ATTACTCGAGctaTT AACTGAAAATTACATTGC-3' (SEQ ID No. 19).

Thermal profile:
Denaturation 1 minute at 94° C.
Annealing 2 minutes at 41° C. (first 5 cycles), 2 minutes at 45° C. (25 additional cycles)
Extension 2 minutes, 20 sec at 72° C.
Final polishing step 10 minutes at 72° C.

The PCRproduct was gel purified using the GELase® kit. The KpnI/SstI fragment of pCT201 was cloned into vector pRS316. This was then digested with EcoRI and XhoI, the excised AGA2 fragment removed by gel purifying the remaining vector fragment, and ligated to purified AGA1 PCR product digested with EcoRI and XhoI. The resulting clone was pCT211. The KpnI/SstI fragment of pCT211 was subsequently cloned into vector YIplac211 to form vector pIU211.

EXAMPLE 8

Expression in Yeast

Yeast strain *S. cerevisiae* BJ5465 (a ura3-52 trpl leu2D1 his3D200 pep4:HIS2 prb1D1.6R can1 GAL). This strain is a pep4 and prb1 mutant making it deficient in proteases. Three nutritional markers have been deleted and may be, used for plasmid selection: URA3, TRP1, and LEU2. HIS3 has been deleted, but the PEP4 deletion is covered with a HIS marker.

Transformation

Vector pIU211 was cut with BsiWI which occurs uniquely within the AGA1 sequence. Approximately 100 ng of this linearized vector and 200 ng pCT202 were transformed simultaneously into yeast strain BJ5465 by electroporation (protocol 2.6.1). Transformants were selected on SD-CAA plates.

Experimental Induction Conditions

A single colony of yeast transformed with pIU211 and pCT202 was inoculated into 3 ml SD-CAA and grown ~24 hours at 30° C. Cell density at this point was ~$10^7$–$10^8$ cells/ml (i.e., $OD_{600}$~1–3). Sufficient cells were collected by centrifugation to inoculate 3 ml SG-CAA to a starting $OD_{600}$ of ~0.5. This culture was grown ~20 hours at 30° C.

EXAMPLE 9

Fluorescent Labeling of Yeast Cells

The following method was used for the fluorescent labeling of yeast cells:

1. Collect 0.2 OD-ml (at 600 nm) of cells following growth for 20 hours in SG-CAA by centrifuging for ~10–30 sec at 14,000 g.
2. Wash cell pellet by resuspending in TBS and spinning down.
3. Resuspend pellet in appropriate volume of TBS to make 100 ml final volume for incubation. Add the following amounts of labeling reagents, as appropriate: 1 ml of 25 mg/ml FITC-dextran (MW 2,000,000) (Sigma); 1 ml 9E10 Mab ascites fluid (Babco) or 10 ml 9E10 at 100 mg/ml (Santa Cruz Biotechnology); 100 ml 12CA5 Mab (Boehringer-Mannheim) at 10 mg/ml in TBS. Mix by vortexing or pipeting up and down.
4. Incubate 1 hour at room temperature, mixing cells approximately every 20 min by flicking tube, vortexing, or pipeting.
5. Spin down the cells and resuspend in appropriate volume of TBS to make 100 ml final volume. Add secondary reagents as appropriate in the following amounts: 4 ml a-mouse-PE (Sigma); 2 ml a-mouse-FITC (Sigma); 1 ml FITC-dextran.
6. Incubate 30 min at room temp.
7. Spin down and wash as in step 2.
8. Resuspend pellet in ~100 ml 10 mM Tris base, pH 8.3 (for anything labeled with FITC) or TBS for microscopy. For flow cytometry, resuspend in 500 ml 10 mM Tris (final cell density ~$10^6$/ml or more). Samples need to be in 0.5 ml microcentrifuge tubes for flow cytometry. For experiments using biotin-fluorescein, cells were grown, induced, harvested, and labeled as described with 10 mM biotin-fluorescein in place of FITC-dextran as the primary label, and a mixture of 3 mg of streptavidin-PE and 1 mg of RED613-conjugated goat anti-mouse F(ab')$_2$ (Life Technologies, Grand Island, N.Y.) as the secondary labeling reagents.

EXAMPLE 10

Confocal Fluorescence Microscopy

Yeast containing plasmid-directing surface expression of the HA peptide (pCT201) or the scFv fusion (pCT202) were grown for 20 hr in medium containing 2% galactose as the only carbon source and subsequently labeled with mAb 9E10, followed by a secondary anti-mouse IgG-R-phycoerythrin (PE) conjugate and FITC-dextran, as described. The labeled cells were mounted on polylysine-coated slides in 90% glycerol mounting medium containing 1 mg/ml p-phenylenediamine as an anti-bleaching reagent and analyzed with a laser scanning confocal microscope (UIUC Beckman Institute Microscopy Suite) at a rate of 8 seconds with a 63× power objective. Images from DIC, red PE fluorescence, and green FITC fluorescence were collected.

EXAMPLE 11
Flow Cytometric Analysis and Sorting

Labeled yeast cell suspensions were analyzed on a Coulter Epics XL flow cytometer at the Flow Cytometry Center of the UIUC Biotechnology Center. Event rate was maintained near 500 cells/sec. The population was gated by light scatter to avoid examination of clumped cells, and data for 100,000 events were collected. For initial cell sorting experiments, yeast carrying the pCT202 vector were mixed with the untransformed parent strain BJ5465 and sorted based upon FITC signal on a Coulter 753 cell sorting bench modified with CICERO sorting electronics (UIUC Flow Cytometry Center). Presort and sorted samples were plated on non-selective medium, then replica plated onto medium selective for the pCT202 vector. Purity was determined as the fraction of non-selective colonies which are viable on selective plates.

EXAMPLE 12
Ouantitation of Surface Antibody Expression Level

Cells bearing vector pCT202 and Quantum Simply Cellular beads (Sigma, St. Louis, Mo.) were labeled with FITC conjugated mAb 12CA5 (Boehringer Mannheim, Indianapolis, Ind.) at 10 (g/ml in TBS as described and analyzed on a Coulter Epics XL flow cytometer. Comparison of the fluorescence intensity of the yeast sample with the standard beads allowed determination of antibody binding capacity of the displaying yeast cells by linear regression using QuickCal for Quantum Simply Cellular (Sigma).

EXAMPLE 13
Kinetic Analysis of Antigen Dissociation From Cells Displaying scFv Yeast cells bearing plasmid pCT202 were grown and labeled with anti-c-myc mAb 9E10 and FITC-dextran or biotin-fluorescein, as described. A fraction of the labeled population was analyzed flow cytometrically to determine the initial level of fluorescence. Non-fluorescent competitor (5-aminofluorescein) was added to a final concentration of approximately 10 mM (~1000-fold excess) and the FITC or PE fluorescence of the c-myc positive cell population was followed as a function of time at room temperature (21–23° C.) on a Coulter Epics XL. Data were fitted as an exponential decay. The probability that a polyvalent antigen is bound to the cell as a function of time is given by $P=1-(1-e^{-kt})^N$, where N is the valency, k is the kinetic rate constant for dissociation, and t is time. For long times t, this reduces to $P=Ne^{-kt}$. Thus, extrapolation of data for long t to time zero yields P=N, or a fluorescence intensity of $F_{ext}=N\ F_o$, where $F_{ext}$ is the extrapolated fluorescence at the time of competitor addition and $F_o$ is the actual initial fluorescence. The valency of the interaction of surface displayed scFv 4-4-20 and polyvalent FITC-dextran was therefore determined as the y-intercept of the curves in FIG. 11.

Binding to soluble fluorescein (FDS) was assayed by observing fluorescence quenching by whole cells displaying scFv. Cells were suspended at $2\times10^7$ cells/ml in TBS+0.1% BSA in a quartz cuvette thermostatted at 23° C. and titrated with FDS over a range of 0–7.5 nM. Fluorescence at 520 nm was observed with an SLM Aminco SPF-500 spectrofluorometer using 488 nm excitation. Control cells displaying an irrelevant scFv were titrated to obtain a slope for a two-parameter fit of an equilibrium binding model to the data, yielding equilibrium constants and effective scFv concentrations. Following the equilibrium titration, 5-aminofluorescein was added to 1 mM and the change in fluorescence of the sample followed with time to determine $k_{off}$ for FDS.

EXAMPLE 14
Mutagenesis of scFv Gene

Approximately 100 ng of pCT302 were transformed in duplicate into *E. coli* strain XL1-Red (Stratagene, La Jolla, Calif.) according to the manufacturer's protocol. Following 1 hr induction in SOC medium, the two transformant groups were pooled and ½000 of the pool plated on LB medium containing 100 mg/ml ampicillin to determine transformation efficiency. 5 ml of liquid LB medium containing 50 mg/ml ampicillin plus 100 mg/ml carbenicillin (LB-AMP50-CARB100) were inoculated with the remainder of the transformants and grown overnight at 37° C. ($OD_{600}$~1.0). A sufficient volume of this culture was collected to inoculate 50 ml LB-AMP50-CARB100 to $OD_{600}$=0.01 in a baffled shake flask and grown to $OD_{600}$~1.0–1.1 at 37° C. Cells were collected by centrifugation and used to inoculate 200 ml LB-AMP50-CARB100 to $OD_{600}$=0.001, and the culture was grown at 37° C. to $OD_{600}$~1.0. Plasmid DNA was isolated by the QIAGEN® Maxiprep kit (QIAGEN®, Santa Clarita, Calif.). The recovered DNA was retransformed into XL1-Red and the growth cycle repeated three times, yielding a final product subjected to approximately 90 generations of growth in the mutator strain.

Figure 4:
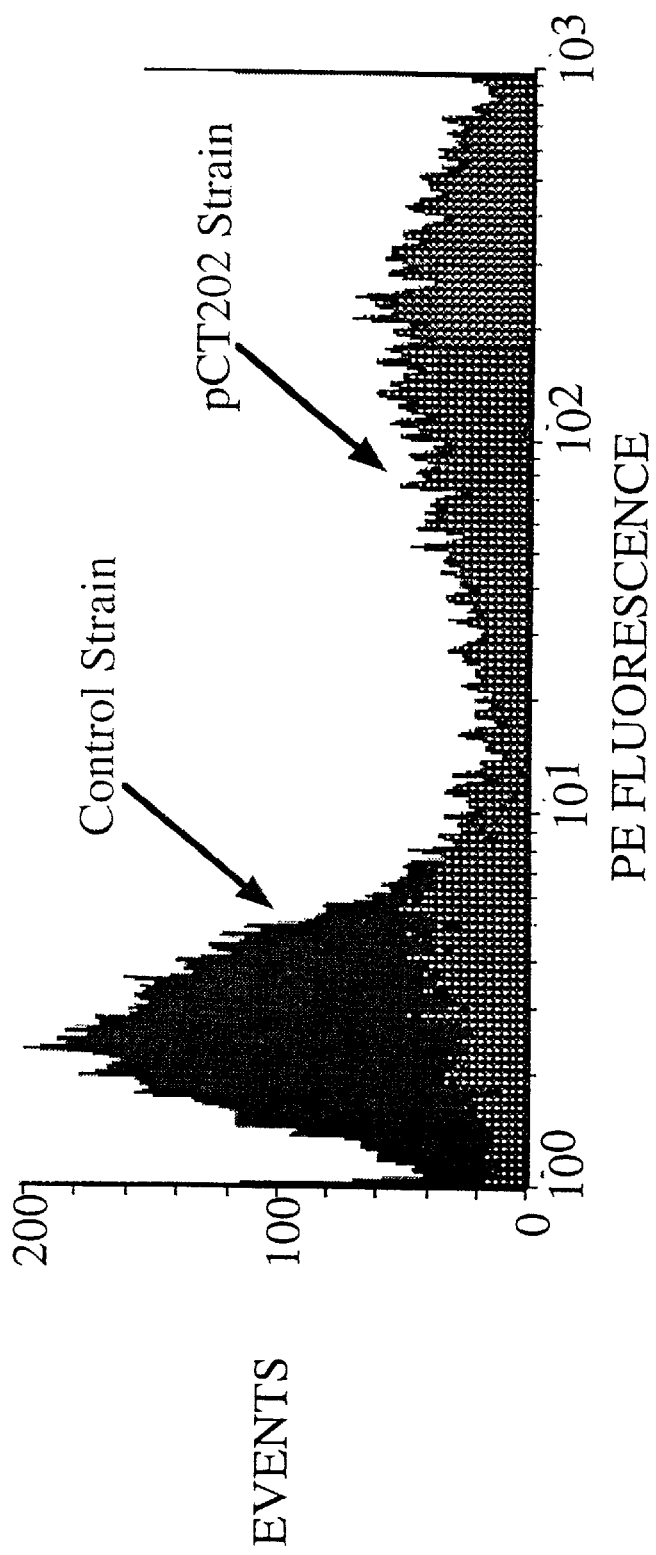
FIG. 4 demonstrates that the displayed fusions can be detected by fluorescence techniques, showing a flow cytometric histogram of yeast labeled with a-c-myc/a-mouse-PE.
Figure 5:
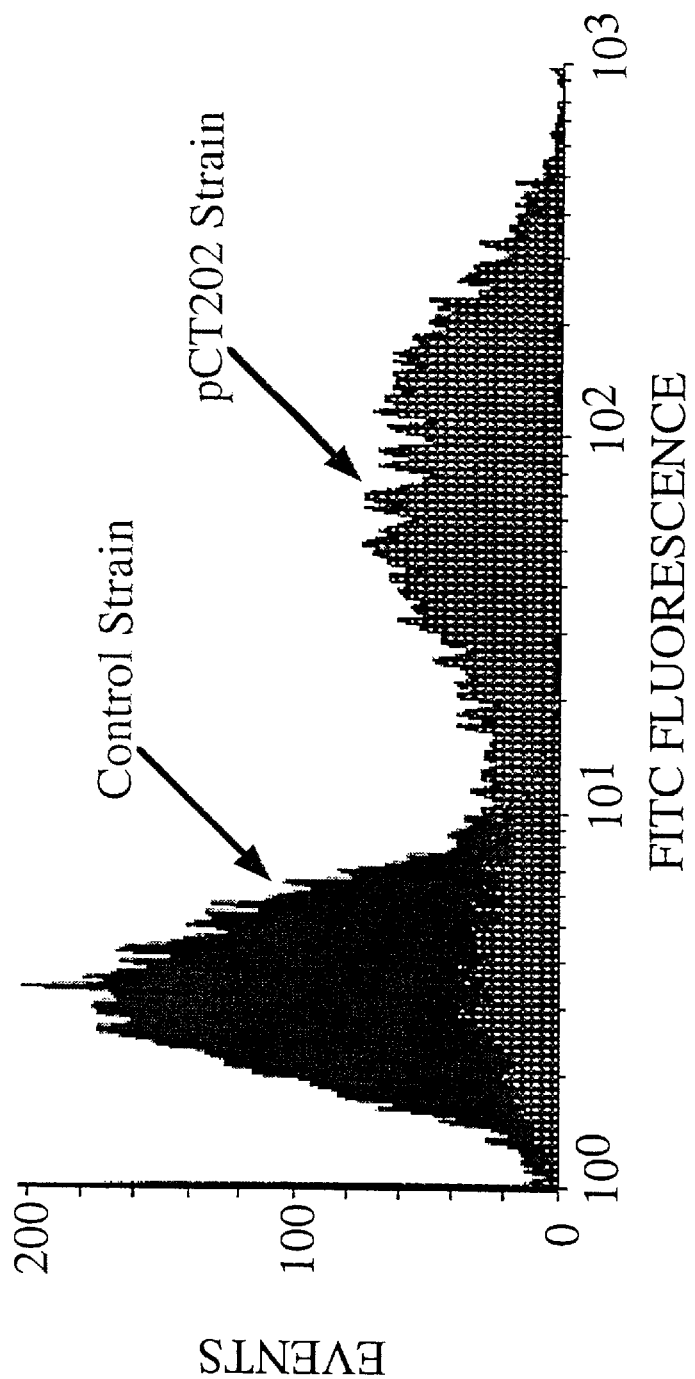
FIG. 5 demonstrates that antigen binding by 4-4-20 scFv can be detected by fluorescence, showing a flow cytometric histogram of yeast labeled with FITC-dextran ($2 \times 10^6$ Da).
Figure 6:
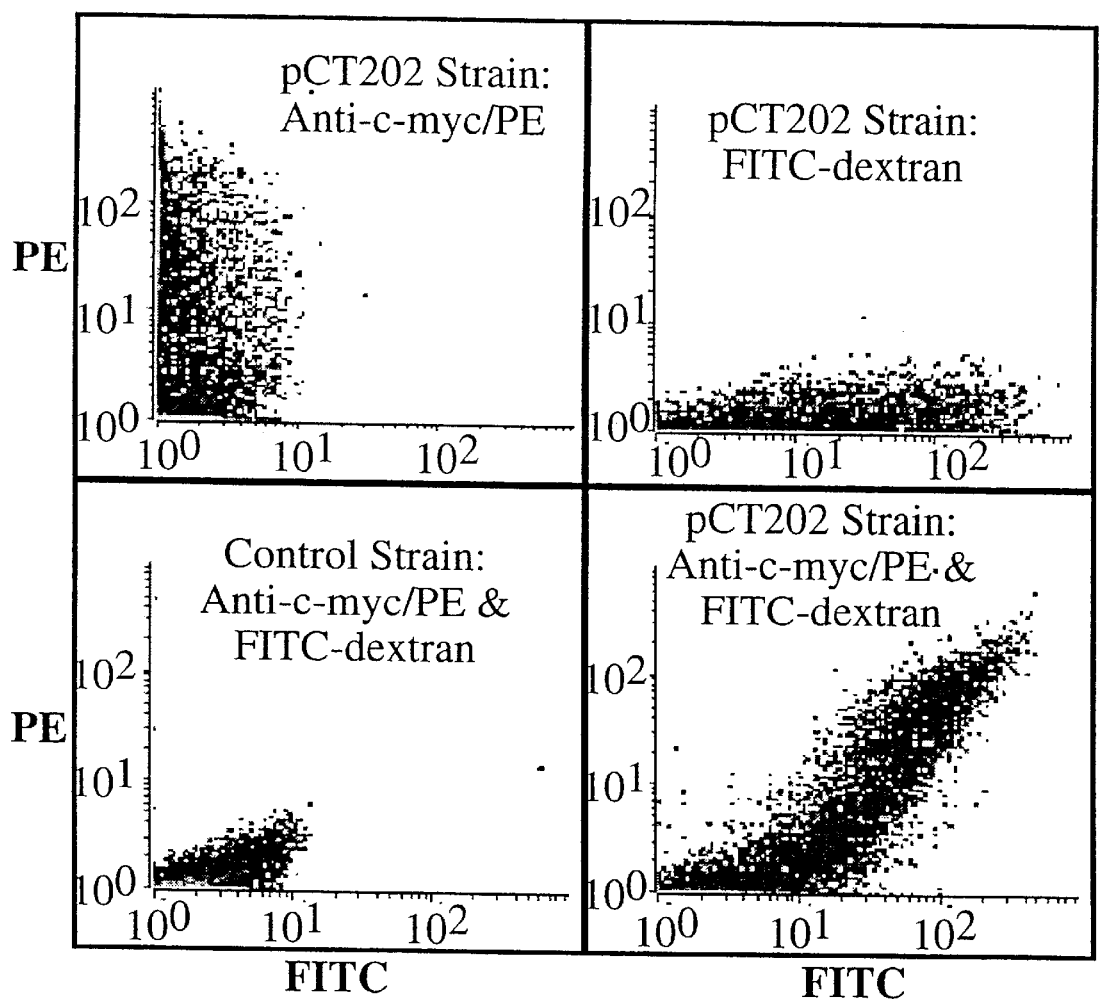
FIG. 6 shows that 4-4-20 activity and c-myc can be detected simultaneously, and demonstrate a 1:1 correlation of fluorescence signals; therefore, variation in intensity signal 1 (FITC) can be normalized for cell-to-cell variation in expression of the protein of interest by the intensity of signal 2 (PE).

EXAMPLE 15
Library Expression and Kinetic Screen 50 mg of mutagenized pCT302 DNA were transformed into yeast strain EBY100 by the method of Gietz and Schiestl in ten separate reactions. The products were pooled, and ½000 of the total plated on selective medium to determine the total number of transformants. The remainder were inoculated into 50 ml of selective glucose medium, grown overnight at 30° C., passaged to $OD_{600}$=0.1, and expanded 10-fold. Selective galactose medium (5 ml) was inoculated to $OD_{600}$=0.5 and grown overnight at 30° C. to $OD_{600}$=1.0–2.0. Samples of $10^7$ cells (1 $OD_{600}$-ml) were labeled with FITC-dextran as described. Following labeling, cells were resuspended in 10 mM 5-aminofluorescein and 9E10 mAb at room temperature for 20 min, at which time samples were rinsed with ice cold buffer to stop competitive dissociation of FITC-dextran and labeled with anti-mouse-PE secondary antibody as described. Samples were sorted on a Coulter 753 bench with a sort window as shown in FIG. 4 and event rate of 4000/sec. $6\times10^7$ cells were examined during sorting round 1 and the window was set to collect 0.2% of the population. The collected cells were regrown in glucose medium and switched to galactose as described prior to repeating the competition and sorting. A total of four rounds of sorting and amplification were performed. $4\times10^7$ cells were examined in round 2, and $2\times10^7$ cells in each of rounds 3 and 4. Rounds 1 and 2 were performed in enrichment mode to provide a high recovery of all positive clones, and rounds 3 and 4 were performed in purify mode to reject coincident negative cells and achieve larger enrichment factors. The products of round 4 were plated to isolate individual clones.

EXAMPLE 16
Establishment of Fusion Display System

A gene coding for a peptide epitope tag fusion with a yeast cell wall protein has been constructed and surface expression of the epitope verified. This cell wall protein, a-agglutinin, is involved in cell-cell adhesion during yeast mating and therefore is exposed on the external cell surface as a receptor for agglutinins on cells of the opposite mating type. Trial mixing and sorting experiments were performed to determine the one-pass and two-pass purification yields and purity for affinity screening by flow cytometry.

EXAMPLE 17

Yeast Mating Agglutinins

In the yeast life cycle, haploid cells occur as one of two possible mating types, a or α. When an a haploid cell and an α haploid cell come into physical contact, they adhere to one another through strong, specific interactions between cell surface adhesion proteins called "agglutinins." Once bound in this fashion, the cells fuse to form a diploid cell. As a platform for antibody display on the yeast cell wall, polypeptide fusions to a subunit of a-agglutinin were constructed. Since the physiological role of agglutinins is to display protein binding sites on the exterior of the cell for specific, high-affinity interaction with other proteins, artifactual steric hindrance from yeast cell wall components was minimal.

As a eucaryote, yeast possesses a secretory apparatus which is highly homologous to that of antibody-secreting B lymphocytes. As a result, artifactual clone-dependent inefficient secretion should be minimized with this host. Numerous studies have revealed striking homology between the yeast and mammalian secretory pathways, such that particular molecules can be exchanged without significant loss of function, both in vivo and in vitro. Expression of mouse BiP functionally replaces yeast BiP, whose expression is essential for growth (Normington, 1989). Expression of mammalian PDI functionally replaces yeast PDI, another essential yeast ER lumenal protein (Gunther et al., 1993). Given the extensive similarities between yeast and mammalian secretion, clonal variability in antibody expression due to misfolding should be substantially reduced in yeast, compared to bacterial hosts. In fact, folding, assembly, and secretion of active antibodies in yeast has been demonstrated previously (Wood et al., '85; Horwitz et al., '88).

Yeast a-agglutinin is synthesized as two subunits: Aga1p, which possesses a phosphatidyl-inositol-glycan tail for anchorage to the cell wall and Aga2p, which binds to α-agglutinin with high affinity ($K_D \approx 1$ nM) (Lipke & Kurjan, 1992). Aga1p and Aga2p are linked by intersubunit disulfide bonds, and Aga2p is released to the growth medium after incubation with reducing agents such as DTT. Although phosphatidyl-inositol-glycan tails are generally localized to a membrane, substantial evidence has accumulated that Aga1p is linked to the fibrous glucan in the cell wall by transglycosylation (de Nobel & Lipke, 1994).

EXAMPLE 18

Fusion Construction

In order to establish the feasibility of using agglutinin fusions to display polypeptides on the yeast cell surface, an "epitope tag" peptide was first genetically fused to Aga2p. It is straightforward to extend this approach to antibody fusions. Passage of scFv molecules through the yeast secretory pathway is efficient, since folding, assembly, and secretion of active IgG's and Fab's has been demonstrated in yeast (Horwitz et al., 1988; Wood et al., 1985).

The AGA2 gene was cloned by PCR from a yeast genomic library and subcloned into an expression vector containing the strong copper-inducible CUP1 promoter which allows 25-fold variation of expression level. Coding sequence for the influenza HA epitope tag (Tyr-Pro-Tyr-Asp-Val-Pro-Asp-Tyr-Ala) (SEQ ID No. 1) was fused to the 3' end of the AGA2 open reading frame, preceded by a Factor Xa site-specific protease cleavage site (Ile-Glu-Gly-Arg) (SEQ ID No. 26). The DNA sequence of this construct is shown in FIG. 7 (SEQ ID No. 21). Convenient restriction sites have been included for in-frame fusion of single-chain antibody genes.

Figure 9A:
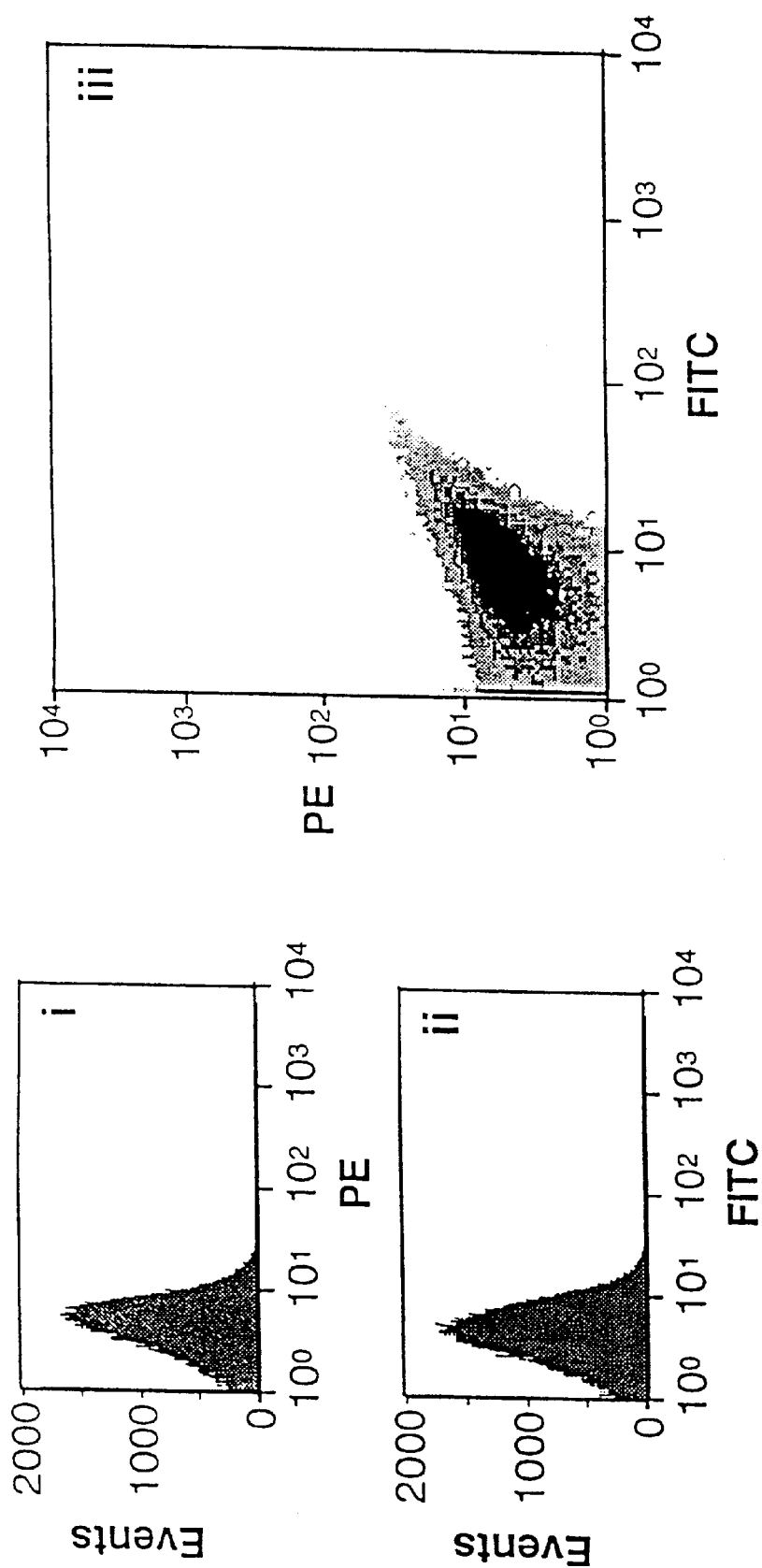
FIG. 9 (Parts A–C) shows flow cytometric analyses of yeast displaying scFv. Yeast strains displaying either (FIG. 9A) an irrelevant peptide or (FIG. 9B) the 4-4-20 scFv were labeled with mAb 9E10 and FITC-dextran. Cells displaying scFv were also treated with 5 mM DTT prior to labeling (FIG. 9C). (i) Univariate histograms of PE fluorescence associated with labeling by 9E10; (ii) univariate histograms of FITC fluorescence; (iii) bivariate histograms showing correlation between PE and FITC fluorescence.
Figure 9B:
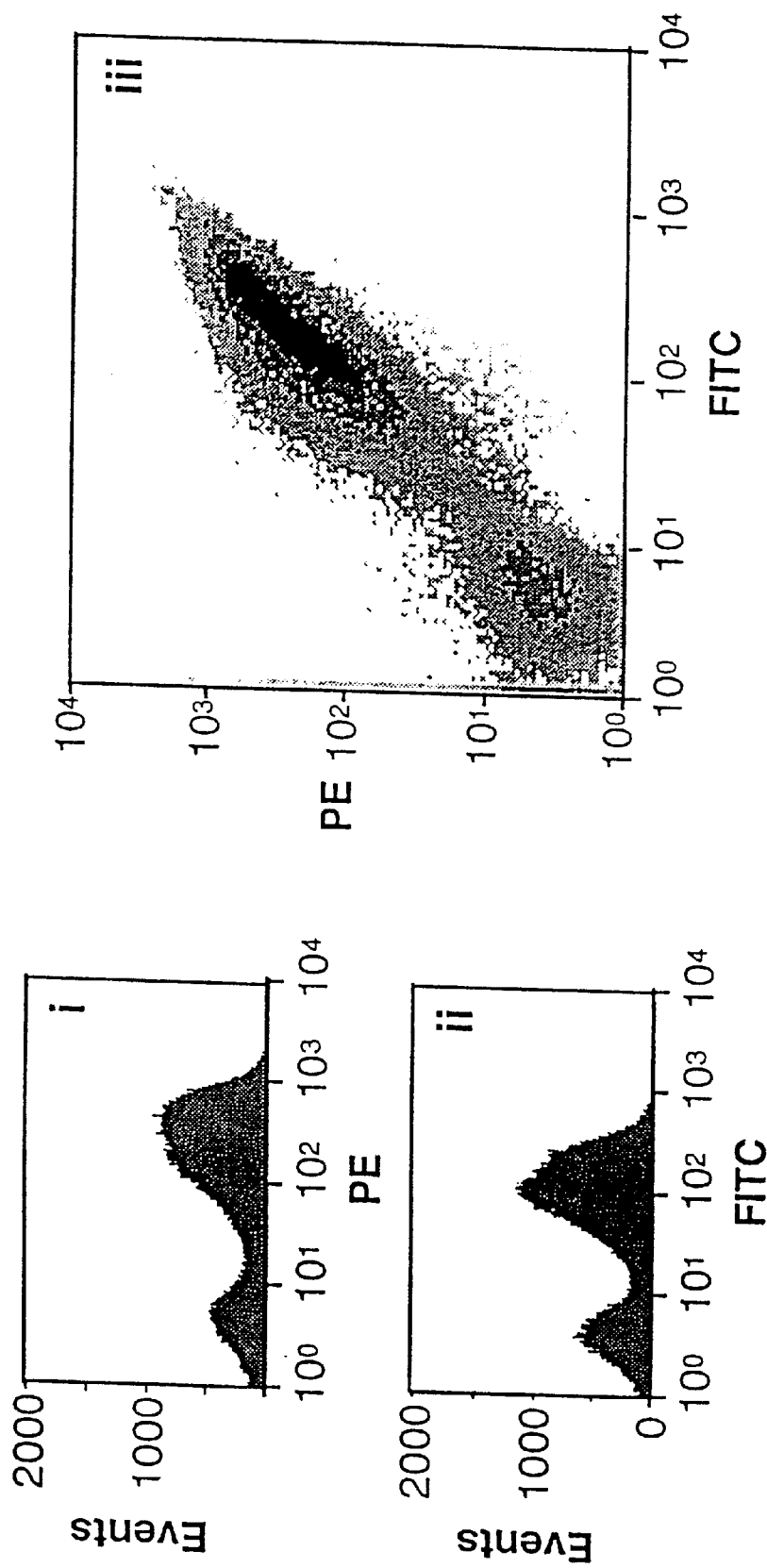
Figure 9C:
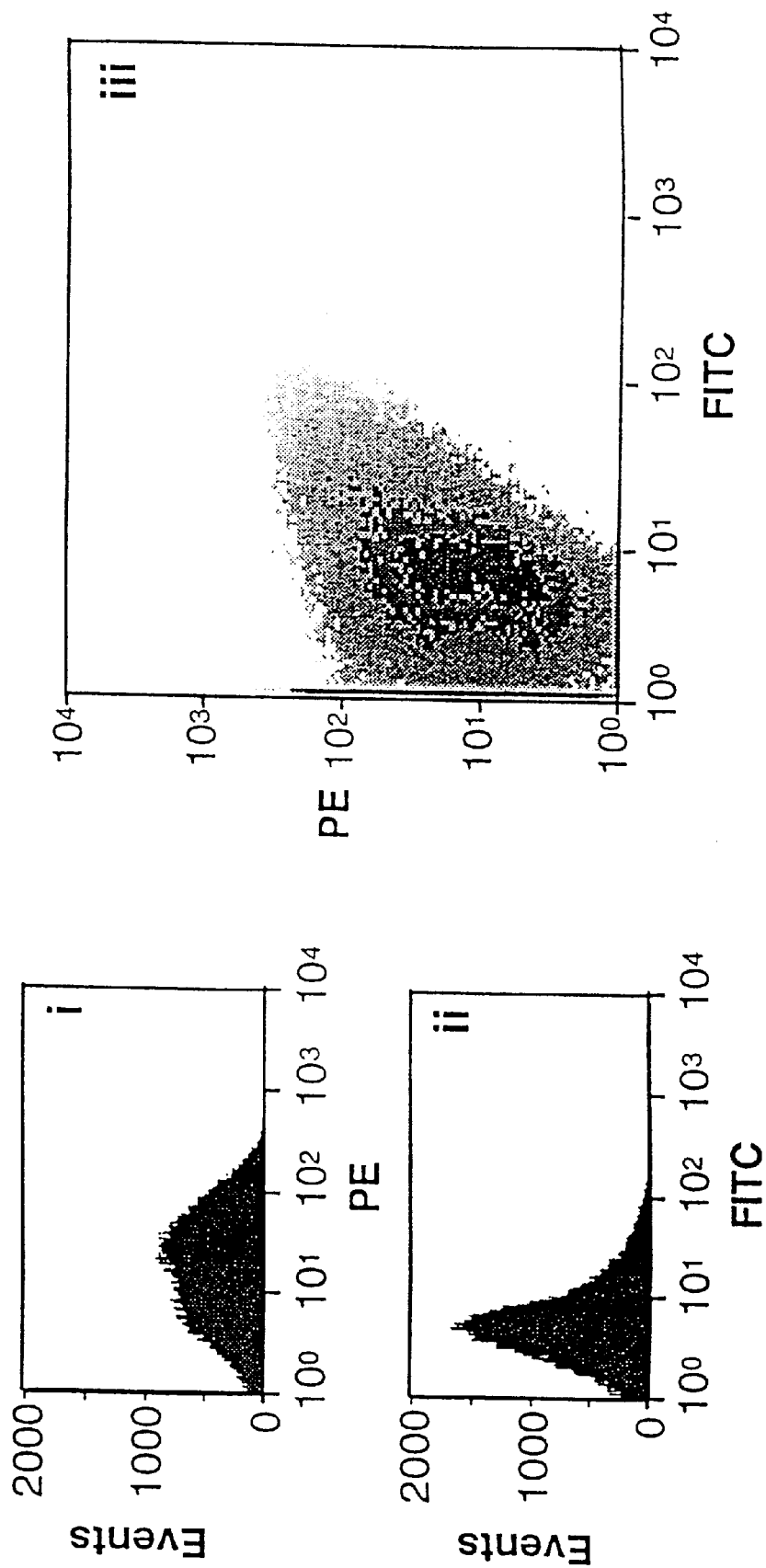

Although the Aga2p-HA fusion is simply a construction intermediate towards the final Aga2p-HA-antibody fusion, it does provide a means for confirming that a fusion peptide is anchored and accessible on the cell surface in this system. Anchorage of the HA peptide to the external cell wall by the fusion has been verified by immunofluorescent staining of whole unfixed cells with the 12CA5 mAb (Boehringer Mannheim, Indianapolis, Ind.), detected by flow cytometry and fluorescence microscopy (FIG. 9). Since whole 12CA5 antibody molecules bind to the HA epitope without any disruptive biochemical treatment of the cell wall, the Aga2p is accessible to the cell exterior for macromolecular recognition.

As described previously, the Aga2p binding subunit is attached to the cell wall through disulfide bonds to Aga1p, which is covalently anchored to other cell wall components. Treatment with DTT abolishes labeling with 12CA5, indicating that the Aga2p-HA fusion is attached to the cell surface by disulfide bonds. The AGA1 gene was cloned by PCR and subcloned downstream of the GAL1 promoter. Expression of AGA1 was induced by switching to galactose growth media.

The HA epitope tag was included in antibody fusions, to enable double fluorescence labeling for both surface antibody levels and binding of fluorescently-labeled antigens. This approach decouples cell-to-cell variations in antibody expression level from single-cell measurements of antigen affinity. For example, indirect immunofluorescence with phycoerythrin-labeled secondary IgG against the a-HA monoclonal antibody provides a measure of surface antibody numbers, while fluorescein-labeled antigen bound to the antibodies provides a measure of binding affinity. Because $\approx 10^4$ copies of a-agglutinin are displayed per cell, stochastic effects on binding measurements are minimal. Since commercial flow cytometers can detect under $10^3$ fluorophore molecules, signal-to-noise ratio should not be problematic. The ratio of green fluorescence (fluorescein, i.e., antigen binding) to red fluorescence (phycoerythrin, i.e., antibody number) is proportional to the fraction of antibodies bound by antigen.

In order to test the separation factors possible by this method, cells expressing the HA epitope tag were mixed at defined ratios with wild-type cells. The mixture of cells was labeled with fluorescein-labeled a-HA IgG and the most highly fluorescent subpopulation was sorted by flow cytometry. The sorted fraction was recultured and the fraction of cells bearing the Aga2p-HA fusion were determined by replica plating for a genetic marker associated with the expression vector. From this information, the single-pass purification possible by this method was estimated.

EXAMPLE 19

Fusion of a Single-Chain Anti-Fluorescein Antibody to a-Agglutinin

An anti-fluorescein single chain antibody based on the monoclonal antibody 4-4-20 has been constructed and characterized (Bird, '88; Davis et al., 1991). This single chain antibody is known to fold stably and retain affinity comparable to Fab fragments. The gene for monoclonal antibody 4-4-20 was fused to the existing AGA2-HA fusion gene for expression on the yeast cell surface.

Monoclonal antibodies against fluorescein are a useful model system for physicochemical studies of antibody-hapten interaction. The kinetics of antibody-antigen binding (Kranz et al., 1982), thermodynamic analysis of complexation (Herron et al., 1986), the role of electrostatic interactions (Omelyanenko et al., 1993), and site-directed mutagenesis of an antibody binding site (Denzin et al., 1993) have been studied using this system.

Functionality of the displayed 4-4-20 fusion was determined by binding to multiply fluorescein-labeled dextran (Sigma). Since antibody binding quenches fluorescein emissions, the detected fluorescein represents moieties tethered to dextran which is bound to yeast via 4-4-20 bound fluorescein.

EXAMPLE 20
Development of Display Scaffold

Yeast possesses two related cell surface receptors known as a- and α-agglutinin that function to mediate cell-cell adhesion between a and α haploid cells as a prelude to fusion to form the diploid (Lu, 1995). α-agglutinin has been shown to be covalently linked to cell wall glucan by the C-terminus (Lu, 1995; Schreuder, 1993), and a-agglutinin is believed to be anchored by a similar linkage (Lu, 1995). Fusion to the C-terminal portion of a-agglutinin has been used previously to anchor enzymes -and viral antigens on the yeast surface (Schreuder, 1993).

Figure 2:
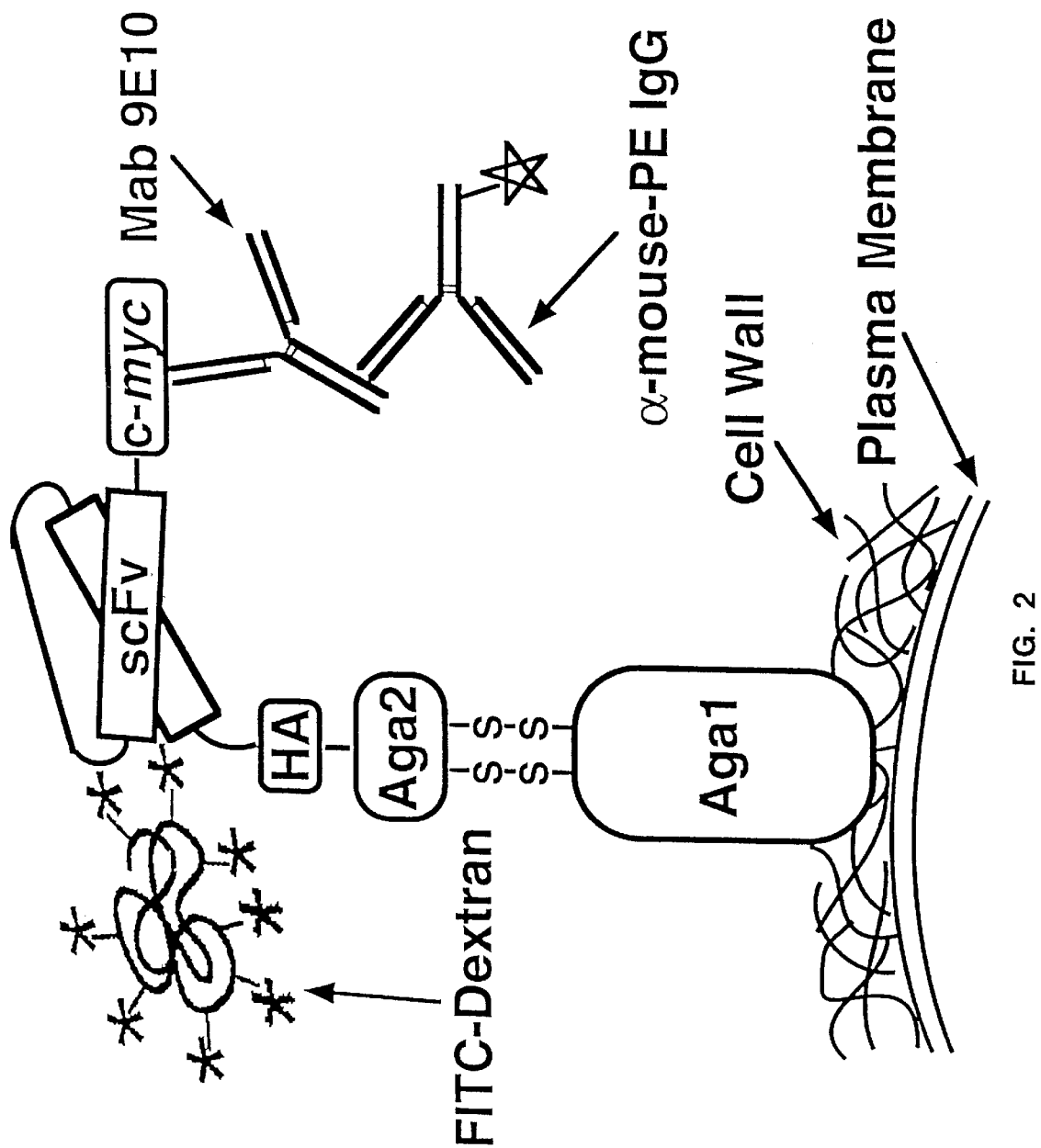
FIG. 2 shows the schematic illustration of surface display on yeast. A nine amino acid peptide epitope from the hemagglutinin antigen (HA) was fused to the C-terminus of the Aga2p subunit of a-agglutinin, followed by the 4-4-20 anti-fluorescein scFv sequence. An additional ten residue epitope tag (c-myc) was fused at the C-terminus of the scFv, allowing quantitation of fusion display independent of antigen binding by either the HA or c-myc tags. The HA or c-myc tag can be used to normalize for variation in the number of displayed fusion proteins in double-label flow cytometry.
Figures 3A, 3B:
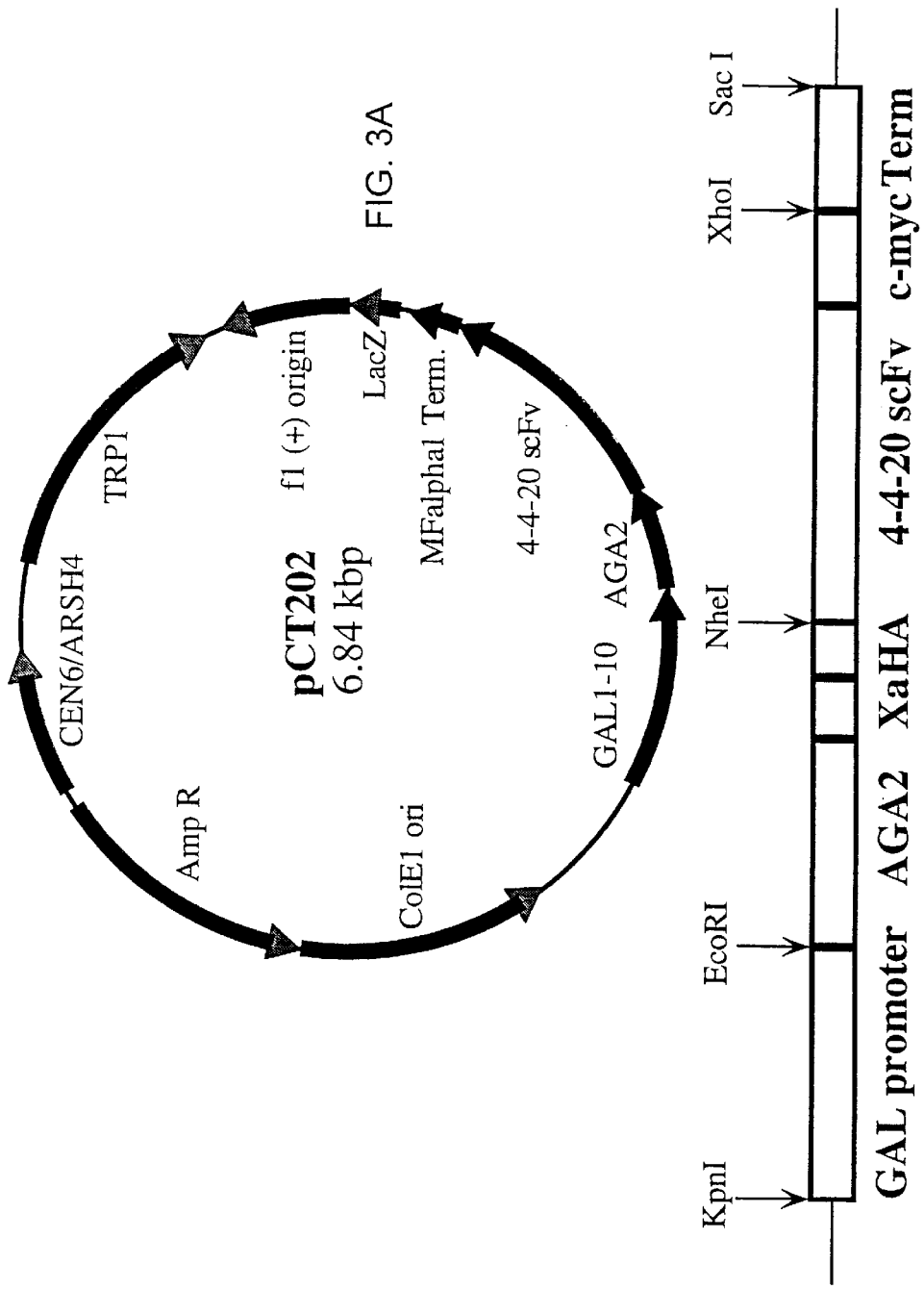
FIG. 3A shows the construction of the vector pCT202.
FIG. 3B shows the specific restriction sites and illustrates the transcriptional regulation by galactose, the N-terminal HA and C-terminal c-myc epitope tags and the Factor Xa protease cleavage site.

As a model system for development of the yeast surface display library screening method, we have displayed a functional anti-fluorescein scFv and c-myc epitope tag on the cell wall of yeast by fusion to a-agglutinin, which unlike α-agglutinin is a two-subunit glycoprotein (FIG. 2). The 725 residue Aga1p subunit anchors the assembly to the cell wall (Roy, 1991) via β-glucan covalent linkage (Lu, 1995); the 69 amino acid binding subunit Aga2p is linked to Aga1p by two disulfide bonds (Cappellaro, 1994). The native a -agglutinin binding activity is localized to the c-terminus of Aga2p (Cappellaro, 1994); thus, this represents a molecular domain with accessibility to extracellular macromolecules and a useful site for tethering proteins for display. A vector for displaying proteins as C-terminal fusions to Aga2p was constructed (FIG. 3).

EXAMPLE 21
Verification of Expression and Surface Localization of scFv

Expression of the Aga2p-scFv fusion is directed by the inducible GAL1 promoter (Johnston, 1984). Growth of yeast on glucose medium allows essentially complete repression of transcription from the GAL1 promoter, an important consideration for avoiding counterselection against sequences which negatively influence host growth. Switching cells to medium containing galactose induces production of the Aga1p and Aga2p fusion gene products, which associate within the secretory pathway and are exported to the cell surface. Surface localization of the Aga2p-scFv fusion has been verified by confocal fluorescence microscopy and flow cytometry. Cells labeled simultaneously with an anti-c-myc mAb and fluorescein-conjugated dextran (FITC-dextran) were examined by laser scanning confocal microscopy (FIG. 8). Control cells bearing a vector which directs display of an irrelevant peptide (i.e., a hemagglutinin (HA) epitope tag only) are not labeled by mAb specific for the c-myc epitope or FITC-dextran (FIG. 8A).

In contrast, cells bearing the surface display vector pCT202 expressing the Aga2p-scFv-c-myc fusion are co-labeled by both the anti c-myc antibody and FITC-dextran (FIG. 8B), demonstrating that the antigen binding site is accessible to very large macromolecules. Both of these strains are positively stained by mAb 12CA5 directed against the HA epitope tag. Accessibility of the fusion for binding to both an intact IgG (150 kDa) and a $2 \times 10^6$ Da dextran polymer indicates an absence of significant steric hindrance from cell wall components, a significant advantage relative to E coli surface displayed proteins which are buried within a lipopolysaccharide layer that forms a barrier to macromolecular diffusion.

Two-color flow cytometric analysis of these yeast strains likewise demonstrates accessibly displayed scFv on the cell surface. Negative control and scFv displaying strains were labeled with the anti-c-myc mAb 9E10 and FITC-dextran simultaneously. Bivariate histograms demonstrate a linear relationship between the intensity of phycoerythrin fluorescence (level of mAb 9E10 binding) and FITC fluorescence (antigen binding) for the cell population carrying the 4-4-20 display plasmid, while the control population exhibits background fluorescence (FIGS. 9A and B). The distribution of fluorescence intensity within the positive fraction illustrates the importance of correcting the antigen binding signal for cell-to-cell variability in the number of displayed fusions, as determined by epitope tag labeling.

Quantitation of the display efficiency by comparison of an scFv-displaying cell population with calibration standards of known antibody binding capacities yields an average value of greater than $3 \times 10^4$ fusions per cell. Treatment of cells displaying the Aga2p-scFv fusion with dithiothreitol prior to labeling eliminated staining of the cell surface by both FITC-dextran and mAb 9E10 (FIG. 9C), consistent with adherence of the fusion protein to the cell surface by a specific disulfide bonding interaction between the recombinant Aga2p subunit and Aga1p. This property illustrates another important feature of the yeast display system, namely that proteins can be simply released from the cell surface by reduction for further characterization.

To examine further the specificity of the 4-4-20/fluorescein interaction, a competitive dissociation assay was performed using a non-fluorescent analog of fluorescein, 5-aminofluorescein. Analysis of these data yields a monovalent dissociation rate constant ($k_{off}$) at 21° C. of $3.7 \times 10^{-3}$ sec$^{-1}$ for FITC-Dextran, and $3.9 \times 10^{-3}$ sec$^{-1}$ for fluorescein-biotin. Extrapolation of the exponential fit to t=0 sec shows that the average valency of the interaction of a FITC-dextran molecule with scFv is less than 1.5. Similar results were obtained using fluoresceinated inulin, fluorescein-conjugated bovine serum albumin, and fluorescein-biotin as the competitor, indicating that the labeling of cells by FITC-dextran or fluorescein-biotin is due to a specific interaction between the displayed fusion and the fluorescein moiety. Furthermore, dissociation kinetics of fluorescein disodium salt (FDS) from surface displayed 4-4-20 scFv matched those from yeast-produced soluble 4-4-20 scFv as observed by spectrofluorometry.

EXAMPLE 22

Enrichment of Displaying Cells by Flow Cytometric Cell Sorting

To determine the effectiveness of flow cytometric sorting with yeast surface display, mixtures of yeast bearing the surface display vector with those lacking the associated selectable marker were sorted and purities independently determined by replica plating. Significant enrichment factors (up to 600-fold) are obtained (TABLE I). Thus, rare clones may be selected from yeast displayed libraries by initially enriching positive cells at relaxed stringency and high yield to provide a smaller population which can then be subjected to several passes of more stringent sorting to isolate rare clones.

TABLE I

Cells displaying 4-4-20 can be selectively enriched by flow cytometry

| Initial Fraction w/ pCT202 | Replica Colonies | Sorted Fraction w/ pCT202 | Enrichment Factor |
|---|---|---|---|
| 14% | 48/58 | 83% | 6x |
| 0.5% | 87/92 | 95% | 200x |
| !!--0.1%* | 34/58 | 59% | 600x |

*Initial fraction was estimated by flow cytometry.

Figure 10A:
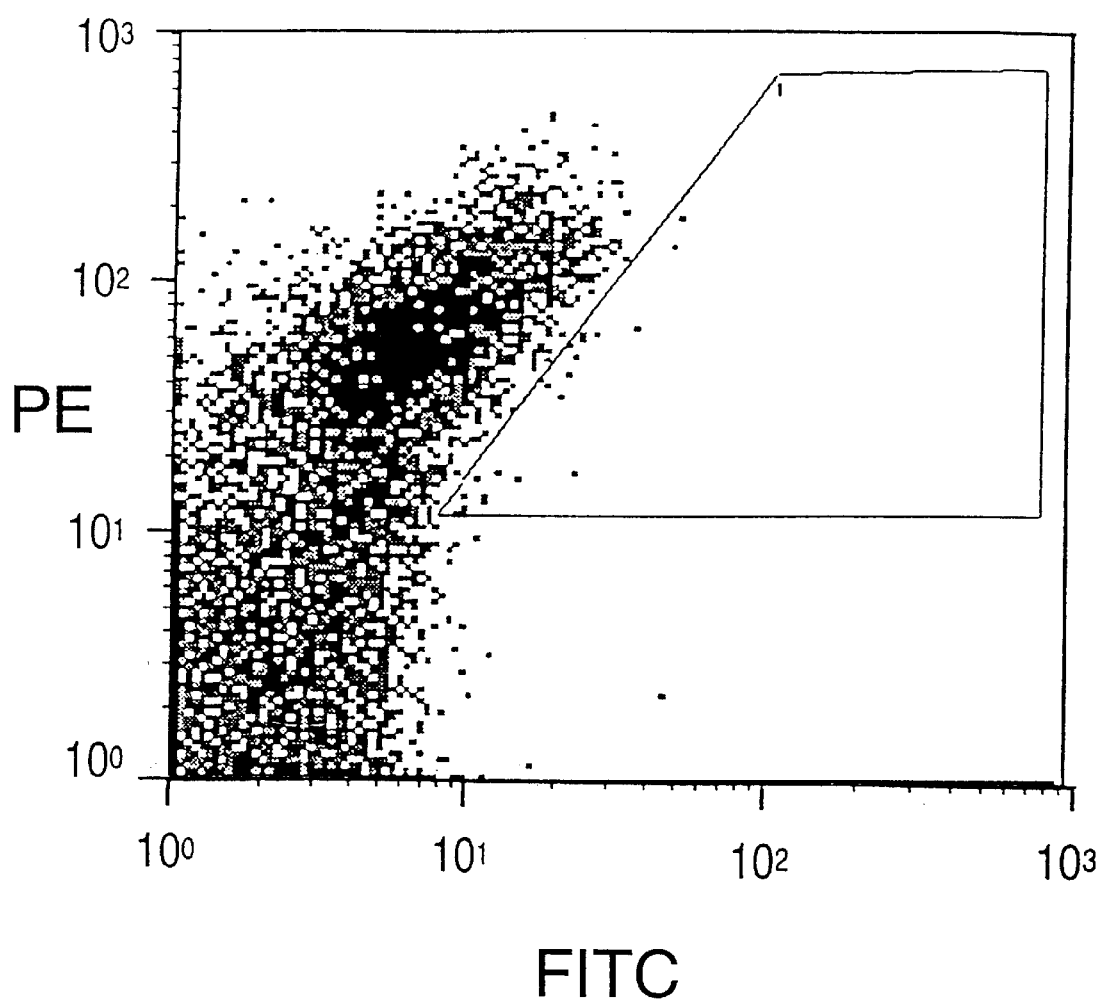
FIG. 10 (Parts A–B) demonstrates the enrichment of yeast displaying improved scFv variants by kinetic selection and flow cytometric cell sorting. Yeast expressing a mutagenized 4-4-20 scFv library (FIG. 10A) and a yeast pool resulting from three rounds of kinetic selection and amplification (FIG. 10B) were subjected to competitive dissociation of fluorescent antigen with 5-aminofluorescein, leaving cells displaying the tightest binding mutants with the highest ratio of FITC intensity/PE intensity.
Figure 10B:
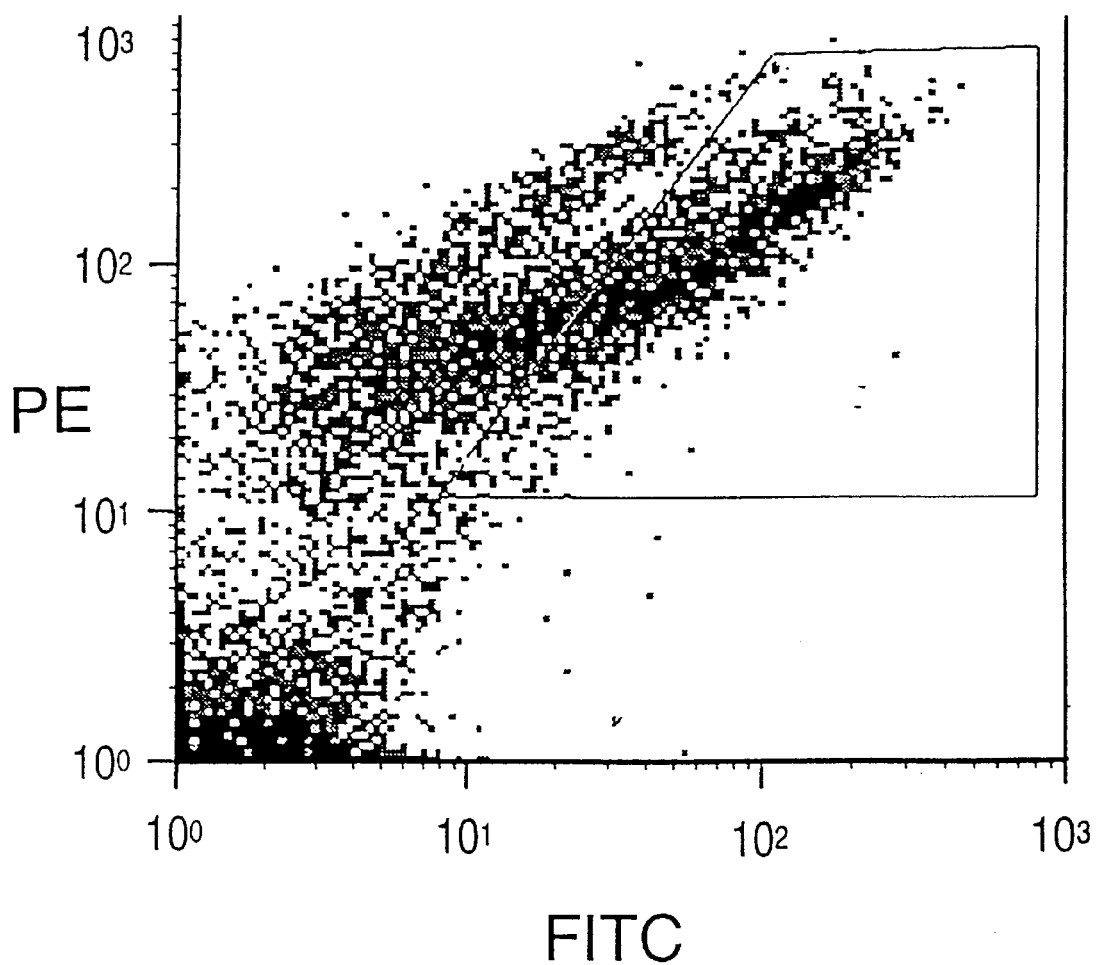

EXAMPLE 23
Isolation of Mutant scFv With Lower $k_{off}$ From a Yeast Displayed Mutagenized Library Selection of scFv genes randomly mutagenized by propagation in a "mutator" strain of E. Coli has been described (Low, 1996). A library of ~5×10⁵ 4-4-20 scFv mutants created by propagation of the yeast surface display vector in such a strain was expressed in yeast. The pool of cells displaying the scFv library were subjected to kinetic selection by competition of FITC-dextran labeled cells with 5-aminofluorescein. c-myc positive cells exhibiting the highest ratio of FITC to PE fluorescence were collected by flow cytometric sorting (FIG. 10A), amplified by regrowth under fusion repressing conditions (glucose carbon source), induced for surface fusion display, and resorted. Cells demonstrating a substantially increased persistence time of labeling by FITC-dextran were dramatically enriched following three rounds of sorting and amplification (FIG. 10).

Figure 11:
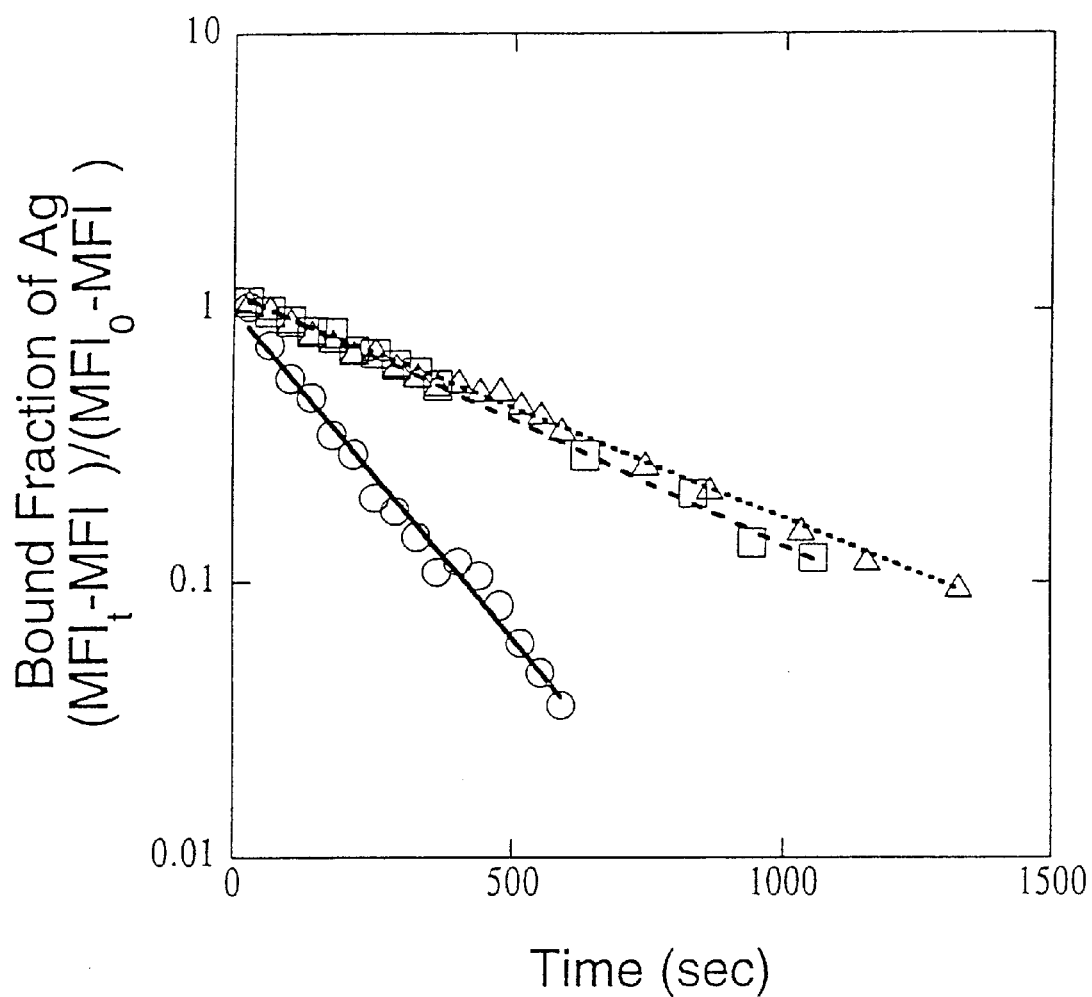
FIG. 11 shows dissociation kinetics of the interaction between fluorescein and surface displayed scFv. Yeast displaying 4-4-20 scFv (circles), mutant 4M1.1 (squares) isolated from the library, and mutant 4M1.2 (triangles) were labeled with mAb 9E10 and FITC-dextran. 5-aminofluorescein was added as a competitor. Mean intensity of FITC fluorescence of the 9E10 positive population of cells was followed as a function of time. The slope of the line is equal to the kinetic dissociation rate, and the extrapolated value at time t=0 sec is equal to the valency of the interaction. $MFI_i$= relative mean fluorescence intensity of yeast at time t=i.

FITC-dextran dissociation kinetics for two individual clones selected from the scFv library differed by 2.9-fold compared to wild-type 4-4-20 scFv (FIG. 11). Rate constants for the mutants were $1.9 \times 10^{-3}$ sec$^{-1}$ (mutant 4M1.1) and $2.0 \times 10^{-3}$ sec$^{-1}$ (4M1.2) at 23° C., compared to $5.6 \times 10^{-3}$ sec$^{-1}$ for wild-type; similar experiments yielded $k_{off}$ values for fluorescein-biotin of $2.4 \times 110^{-3}$ sec$^{-1}$, $2.8 \times 10^{-3}$ sec$^{-1}$, and $5.0 \times 10^{-3}$ sec$^{-1}$, respectively. Additionally, soluble fluorescein dissociation kinetics determined by spectrofluorometry demonstrated a 2.2-fold improvement for both mutants relative to wild-type, and initial equilibrium fluorescence quenching experiments suggest a similar improvement in the affinity constant of the binding reaction. Isolation of clones with only threefold reduced off-rate demonstrates the capability of this screening method to achieve precise quantitative distinctions.

Of 26 selected clones individually analyzed, two were identically improved in $k_{off}$ (4M1.1 and 4M1.2, described above); two demonstrated wild-type $k_{off}$ with a decrease in c-myc labeling skewing the linear expression level/activity relationship; one exhibited wild-type $k_{off}$ and c-myc labeling; and 21 bound with an apparent $k_{off}$ approximately 10-fold lower than wild-type only to polyvalent $2 \times 10^6$ Da FITC-dextran, but not to monovalent FITC-dextran or fluorescein-biotin. Enrichment for clones with increased avidity resulted from use of polyvalent antigen (approximately 90 fluoresceins per dextran); avidity effects can be effectively avoided by appropriate design of screening conditions to ensure monovalent antigen binding. Furthermore, selection of epitope tag mutants can be eliminated by alternately detecting expression level by c-myc and HA tag labeling in sequential sorting rounds, or by alternative mutagenesis strategies targeting changes only to the scFv gene.

These results show that scFv fragments can be displayed on the surface of yeast in a manner accessible for macromolecular recognition and amenable to combinatorial library construction and screening. The displayed scFv specifically binds antigen—the first demonstration of a functional antibody fragment displayed on the yeast cell surface. The application of this display system to library methods for in vitro antibody affinity maturation and for display of other mammalian proteins is a significant complementary alternative to existing technologies such as phage display, bacterial surface display, and the yeast two-hybrid method. Indeed, the literal first-attempt success of the yeast display system in recovery of improved fluorescein-binding scFv mutants from a relatively small library under non-optimized screening conditions clearly demonstrates the robustness of this technology. The demonstrated highly quantitative kinetic analysis of surface-tethered scFv and fine discrimination of clones with similar binding characteristics further attests to the great potential of yeast display for combinatorial optimization of proteins.

EXAMPLE 24
Display of an Antibody to the T Cell Receptor in the Yeast Display System Herein, a scFv (KJ16) specific for the Vb8 region of the T cell receptor (Roehm et al., 1985) was expressed in the yeast display system. This scFv-KJ16 inhibited the activity of T cells by competitively blocking the recognition of a TCR ligand such as the superantigen staphylococcal enterotoxin B (Cho et al., 1995). Since the affinity variants of this scFv may show enhanced T cell inhibition, the use of the yeast display system in engineering higher affinity forms of scFv-KJ16 were examined.

A screen based on equilibrium binding of cell surface scFv to fluorescently-labeled antigen, a Vb8 single-chain TCR (Schlueter et al., 1996) was developed. Using two-channel flow sorting, selection was also based on the binding of a fluorescently-labeled anti-c-myc antibody to a ten-residue c-myc tag at the carboxy-terminus of the scFv. Variant scFv with a higher affinity for the TCR or with a lower affinity for the- anti-c-myc antibody were isolated. As expected, the former had a mutation in a CDR ($V_L$CDR1) and the latter had a mutation in the c-myc epitope. Thus, these findings demonstrate that the yeast display approach can be used either to isolate higher affinity scFv or to identify the epitopes of a displayed protein recognized by a particular Mab.

Plasmids and Strains

The scFv-KJ16 $V_L$ and $V_H$ genes joined by a modified 205 linker (Cho et al., 1995) were subcloned by PCR into the vector pCR-Script (Stratagene, La Jolla, Calif.) following the manufacturer's protocol. A c-myc epitope tag was included at the carboxy-terminus of the scFv. The ~800-bp NheI/XhoI fragment containing the scFv was excised from pCR-Script and ligated into the yeast surface display vector pCT202 containing a nine-residue epitope tag (HA) and the AGA2 open reading frame downstream of the inducible GAL1 promoter. The resultant construct was transformed by the lithium acetate (LiAc) transformation method of Gietz and Schiestl (Gietz et al., 1995) into the S. cerevisiae strain BJ5465 (a ura3-52 trp1 leu2D1 his3D200 pep4::HIS2 prbD1.6 can1 GAL; Yeast Genetic Stock Center, Berkeley, Calif.) containing a chromosomally integrated AGAL controlled by the GAL1 promoter (strain EBY100).

EXAMPLE 25
Induction and Detection of scFv-KJ16 on the Yeast Surface

Yeast cells transformed with pCT202/scFv-KJ16 were grown overnight at 30° C. with shaking in 3 ml selective glucose medium SD-CAA (glucose 2 wt %, Difco yeast nitrogen base 0.67 wt %, casamino acids 0.5 wt %). After ~18–20 hours, recombinant AGA1+AGA2-scFv expression was induced at 20° C. with shaking in 5 ml selective galactose medium (SG-CAA, where 2% galactose replaces the glucose in SD-CAA). Cultures were harvested after ~20–24 hours (1–2 doublings) by centrifugation, washed with PBS (10 mM $NaPO_4$, 150 mM NaCl, pH 7.3) containing 0.1% bovine serum albumin and 0.05% azide, and incubated 45 minutes on ice with 25 mL of 10 mg/ml anti-HA Mab 12CA5 (Boehringer Mannheim, Indianapolis, Ind.), anti-c-myc Mab 9E10 (1:100 dilution of raw ascites fluid; Berkeley Antibody Co., Richmond, Calif.), or biotinylated-scTCR [~360 nM] prepared from inclusion bodies expressed in E. coli (Schodin et al., 1996). Cells were washed with PBS and incubated 30 minutes on ice with either FITC-labeled F(ab')$_2$ goat anti-mouse IgG (1:50; Kirkegaard and Perry Labs, Inc., Gaithersburg, MD) or a streptavidin-phycoerythrin (SA-PE) conjugate (1:100; PharMingen, San Diego, Calif.; ). Labeled yeast cells were analyzed on a Coulter Epics XL flow cytometer at the Flow Cytometry Center of the UIUC Biotechnology Center. Event rate was ~250 cells/sec. Data for 10,000 events was collected, and the population was gated according to light scatter (size) to prevent analysis of cell clumps. These conditions were also used to generate equilibrium antigen binding isotherms after incubation of scFv-KJ16 yeast with various dilutions of scTCR. Scatchard analysis was performed to determine the $K_D$ values, using the estimated concentration of the biotinylated-scTCR and mean fluorescence units taken directly from flow data.

EXAMPLE 26
Production of a scFv-KJ16 Random Mutant Library

Approximately 50 ng of pCT202/scFv-KJ16 were transformed into E. coli XL1-Red cells (Stratagene, La Jolla, Calif.) according to the manufacturer's protocol. Following a 1 hour induction in SOC medium, the recovery was centrifuged at 2000 rpm for 5 minutes and resuspended in 500 ml of liquid LB medium containing 100 mg/ml ampicillin plus 50 mg/ml carbenicillin (LB-AMP100-CARB50). The resuspension was added to 15-ml LB-AMP100-CARB50 in a 50-ml Erlenmeyer flask and grown at 37° C. with shaking. The culture was replenished with a fresh 15-ml LB-AMP100-CARB50 at mid-log phase ($OD_{600}$~0.2–0.4), then grown to saturation ($OD_{600}$~1.0–1.1; this was considered one "cycle" or round of mutation). A small fraction of this culture (0.75 ml) was added to the next cycle (15-ml LB-AMP100-CARB50). After six cycles of growth, Wizard Miniprep (Promega, Madison, Wis.) DNA plasmid preparations were performed on the 15-ml culture. Approximately 4.5 mg of pCT202/scFv-KJ16 DNA from cycle six were transformed into each of 3 tubes of yeast strain EBY100 using the LiAc method (Gietz et al., 1995). The 3 reactions were pooled and after resuspension in 1-ml $ddH_2O$, ½₀₀₀₀of the pool plated on selective plates to determine transformation efficiency. Fifty milliliters of SD-CAA were inoculated with the remainder of the culture, grown overnight at 30° C. with shaking, passaged to $OD_{600}$=0.05, and grown overnight at 30° C. to $OD_{600}$>1.0. Five milliliters of SG-CAA were then inoculated to $OD_{600}$~0.5 and grown overnight at 30° C. with shaking to $OD_{600}$=1.0–2.0.

EXAMPLE 27
Selection of scFv-KJ16 Mutant Library by FACS

Cells were double-labeled as described above with anti-c-myc Mab and biotinylated-scTCR (used at a concentration ~10 nM). The reaction volume was adjusted to maintain ~10-fold molar excess of antigen (scTCR) over surface scFv. Samples were sorted on a Coulter 753 bench with a sort window as shown in FIG. 3 and an event rate of 4,000 cells/sec. A total of $8 \times 10^7$ cells were examined during the first sorting round, with 0.1–0.4% of the population collected. The collected cells were regrown at 30° C. in SD-CAA and switched to SG-CAA prior to the next round of sorting. A total of 4 rounds of sorting was performed, with the first 2 sorts in enrichment mode (high recovery of all positive clones) and the last 2 sorts in purification mode (coincident negative cells rejected). Immediately following the last sort, the collected cells were re-sorted and plated on selective plates to isolate individual clones.

EXAMPLE 28
Rescue and Sequencing of Mutant scFv-KJ16 Genes

Plasmids from scFv-KJ16 yeast (wt and 2 mutants) were rescued according to the protocol described by Ward (Ward, 1991), except that cells were disrupted with a bead beater (BioSpec Products, Inc., Bartlesville, Okla.) for 2 minutes instead of vortexing. Cells were centrifuged for I minute and the upper (aqueous) phase collected. A Wizard® miniprep kit (Promega, Madison, Wis.) was used to prepare the plasmid DNA and E. coli DH5α competent cells (GibcoBRL, Gaithersburg, Md.) were transformed with 1 ml of the DNA preparation using the $CaCl_2$ method. Transformations were plated on LB-AMP50. Sequencing of wt scFv-KJ16 and two mutants (mut4 and mut7) was performed using primers that flank the scFv of the display vector and fluorescence automated sequencing (Genetic Engineering Facility of the UIUC Biotechnology Center).

EXAMPLE 29
TCR Binding by Yeast Cell Surface scFv

The monoclonal anti-TCR antibody KJ16 recognizes a conformational epitope on the Vb8 chain of the TCR (Brodnicki et al., 1996). KJ16 has been used for many in vivo studies in mice, including efforts to target and delete the Vb8 population of T cells (Born et al., 1987, McDuffie et al., 1986, Roehm et al., 1985). To evaluate the possible effects of varying antibody affinity in mediating these effects, the use of a yeast display system to identify KJ16 variants with increased affinity for TCR was examined. The scFv gene from the anti-TCR antibody KJ16 has been cloned previously and the scFv protein exhibited approximately the same affinity, $K_D$~120 nM, as KJ16 Fab fragments (Cho et al., 1995).

The scFv-KJ16 coding sequence was subcloned so as to be expressed as a fusion polypeptide with the Aga2p agglutinin subunit expressed on the yeast cell surface. The fusion polypeptide includes a hemagglutinin (HA) epitope tag N terminal to the scFv and a c-myc epitope tag at the carboxy-terminus. The inclusion of these epitopes allows monoclonal anti-HA (12CA5) and anti-c-myc (9E10) antibodies to be used in flow cytometry to quantify surface expression of the full length scFv independently of antigen-binding activity. Such normalization helps account for the effects of cell-to-cell variability in surface levels of the fusion polypeptide. As discussed below, the availability of two independent epitope tags can also control for the selection of individual epitope mutants that might not be desired in screening for ligand binding mutants. To evaluate the binding properties of cell surface scFv, a soluble single-chain Vb8-Va3 TCR(Schodin et al., 1996) was biotinylated and the bound ligand was detected with a phycoerythrin-streptavidin conjugate.

Figure 12B:
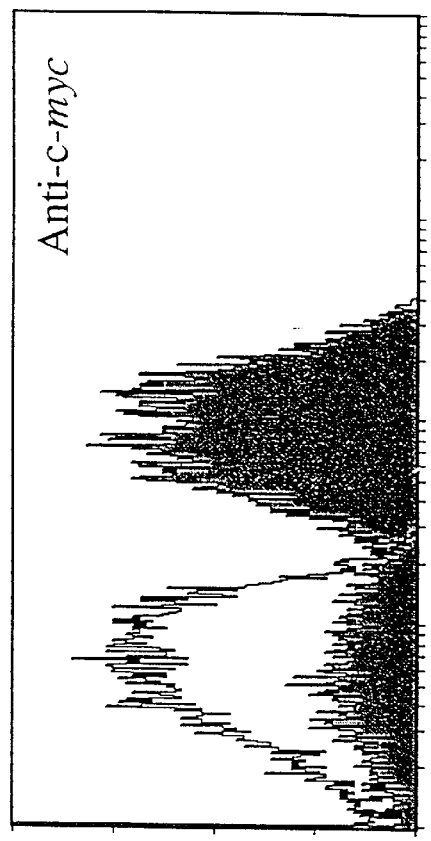
FIG. 12 (Parts A–D) shows the expression levels and antigen binding properties of yeast surface displayed scFv-KJ16 (shaded) and control Aga2p/HA (unshaded). Yeast strain EBY100 was transformed with scFv-KJ16 cloned into the yeast display vector pCT202 or the pCT202 vector alone. After induction in galactose medium at 20° C. overnight, cells were stained with fluorescent antibodies and analyzed by flow cytometry.
(FIG. 12A) scFv-KJ16/yeast or Aga2p/HA/yeast stained with mouse anti-HA Mab (12CA5) followed by FITC-labeled goat anti-mouse IgG, (FIG. 12B) scFv-KJl6/yeast or Aga2p/HA/yeast stained with mouse anti-c-myc Mab (9E10) followed by FITC-labeled goat anti-mouse IgG, (FIG. 12C) scFv-KJ16/yeast or Aga2p/HA/ yeast stained with biotinylated-scTCR at ~10 nM followed by a streptavidin-phycoerythrin conjugate, and (FIG. 12D) scFv-KJ16/yeast stained with biotinylated-scTCR followed by a streptavidin-phycoerythrin conjugate in the presence (shaded) or absence (unshaded) of intact IgG KJ16 at 100 mg/ml.

FIG. 12 shows that yeast transformed with the scFv-KJ16/Aga2 plasmid expressed the HA epitope (FIG. 12A) and the c-myc epitope (FIG. 12B). Control yeast transfected with only the Aga2p/HA expression vector were positive for the anti-HA Mab but not for the anti-c-myc antibody. The fraction of cells in the non-fluorescent population has been found to depend on plasmid stability and culture growth phase, but the physiological processes that are involved are unknown. Nevertheless, decreasing the induction temperature to 20° C. and decreasing the induction time to less than two culture doublings produces populations with >75% of the cells displaying the scFv-KJ16. scFv-4-4-20 was displayed with this system with approximately the same proportion of positive cells.

Figure 12D:
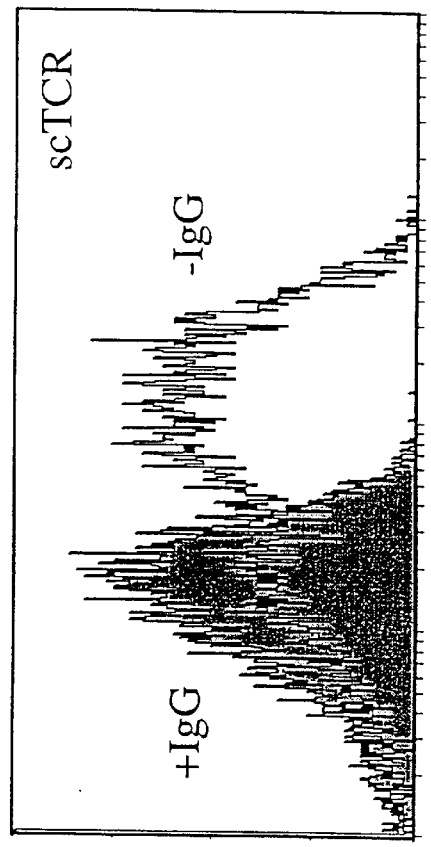
Figure 12A:
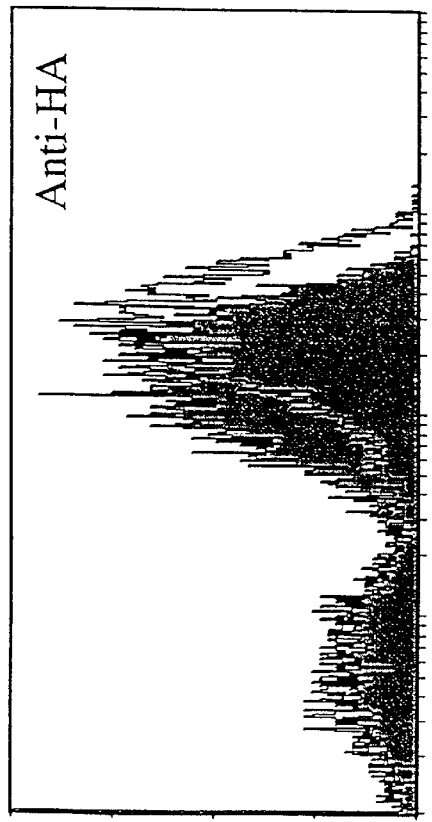
Figure 12C:
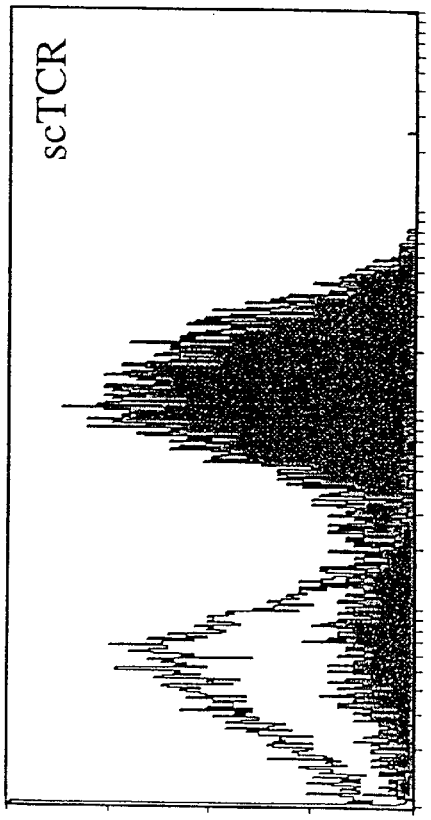

Binding of biotinylated scTCR to cell surface scFv was also detected by flow cytometry (FIG. 12C). The fraction of cells that expressed active scFv was similar to that detected with anti-HA and c-myc antibodies, consistent with the expression of full length, properly folded scFv. Furthermore, two-color histograms demonstrated a tight correlation of scTCR binding with both HA and c-myc epitope display. Biotinylated-scTCR binding is specific to yeast displaying the scFv-KJ16, and was completely inhibited by excess soluble KJ16 IgG (FIG. 12D).

The approximate affinity of the surface displayed scFv-KJ16 was determined in situ on the cell wall by titrating whole cells with varying concentrations of biotinylated scTCR. Equilibrium binding was measured by analyzing cell-bound scTCR by flow cytometry. Scatchard analysis of the binding data (FIG. 13) yielded a $K_D$ of 500 nM, within five fold of that observed for soluble scFv-KJ16. Such agreement is reasonable, since $K_D$ was calculated under the assumption that 100% of the scTCRwas active, likely to be an overestimate (i.e. if only 20% were correctly folded, then the surface scFv would have a $K_D$~100 nM). Previously, a substantial fraction of the scTCR purified from solubilized *E. coli* inclusion bodies is incorrectly folded was found (Schodin et al., 1996).

EXAMPLE 30
Selection of Mutagenized scFv-KJ16/Yeast by Fluorescence-Activated Cell Sorting An *E. coli* mutator strain has been used to mutagenize an scFv for affinity maturation by phage display (Low et al., 1996). This approach was successful in identifying a mutant of scFv-4-4-20 with higher affinity for fluorescein using yeast display. A strength of this mutagenesis approach is its simplicity, requiring only *E. coli* transformation and cell growth. Furthermore, the *E. coli* mutator strain introduces mutations throughout the expression plasmid, and therefore does not bias changes to portions of the scFv believed to be important for determining binding characteristics. Whether this aspect of mutator strain mutagenesis is advantageous depends on the ability to identify key residues that might influence antigen binding, based on available structural information. Examination of published affinity maturation studies suggest that the location of such residues, generally in non-contact residues, is not yet predictable a priori (Hawkins et al., 1993, Patten et al., 1996, Schier et al., 1996, Thompson et al., 1996, Yang et al., 1995, Yelton et al., 1995).

To apply this strategy to scFv-KJ16, the scFv-KJ16/Aga2 plasmid was propagated in the *E. coli* mutator strain XL1-Red (Stratagene) for six cycles of growth. This procedure was predicted to introduce an average of two to three point mutations in the scFv coding sequence, based on a mutation rate per cycle of 1 in 2000 bps. The resultant plasmid preparation was transformed into yeast yielding a library size of approximately $3\times10^5$ transformants. In other work, larger libraries ($10^7$) have been obtained by further optimization of transformation procedures and by pooling independent transformations. This number does not represent an upper size limit for library construction, as further efforts at optimization and scaleup could be straightforwardly applied.

Figure 13:
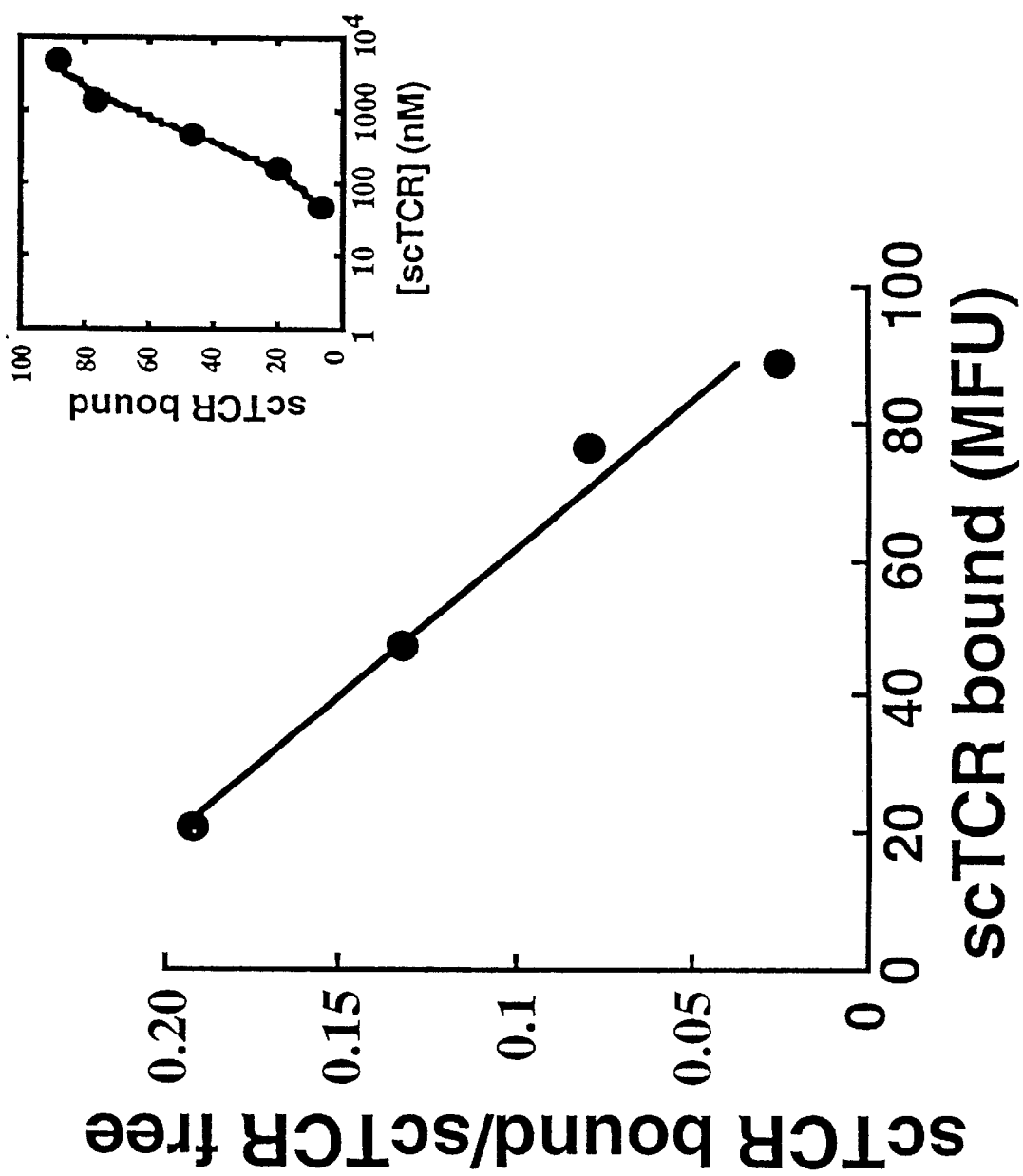
FIG. 13 shows the equilibrium antigen binding isotherm of cell wall displayed scFv-KJ16, determined by flow cytometry. Yeast strain EBY100 displaying surface scFv-KJ16 was incubated with varying concentrations of biotinylated-scTCR, labeled with a streptavidin-phycoerythrin conjugate, and detected by flow cytometry. Data was plotted as a Scatchard diagram or as a titration (inset) and an effective $K_D$ ~500 nM was determined. MFU refers to mean fluorescence units.
Figure 14A:
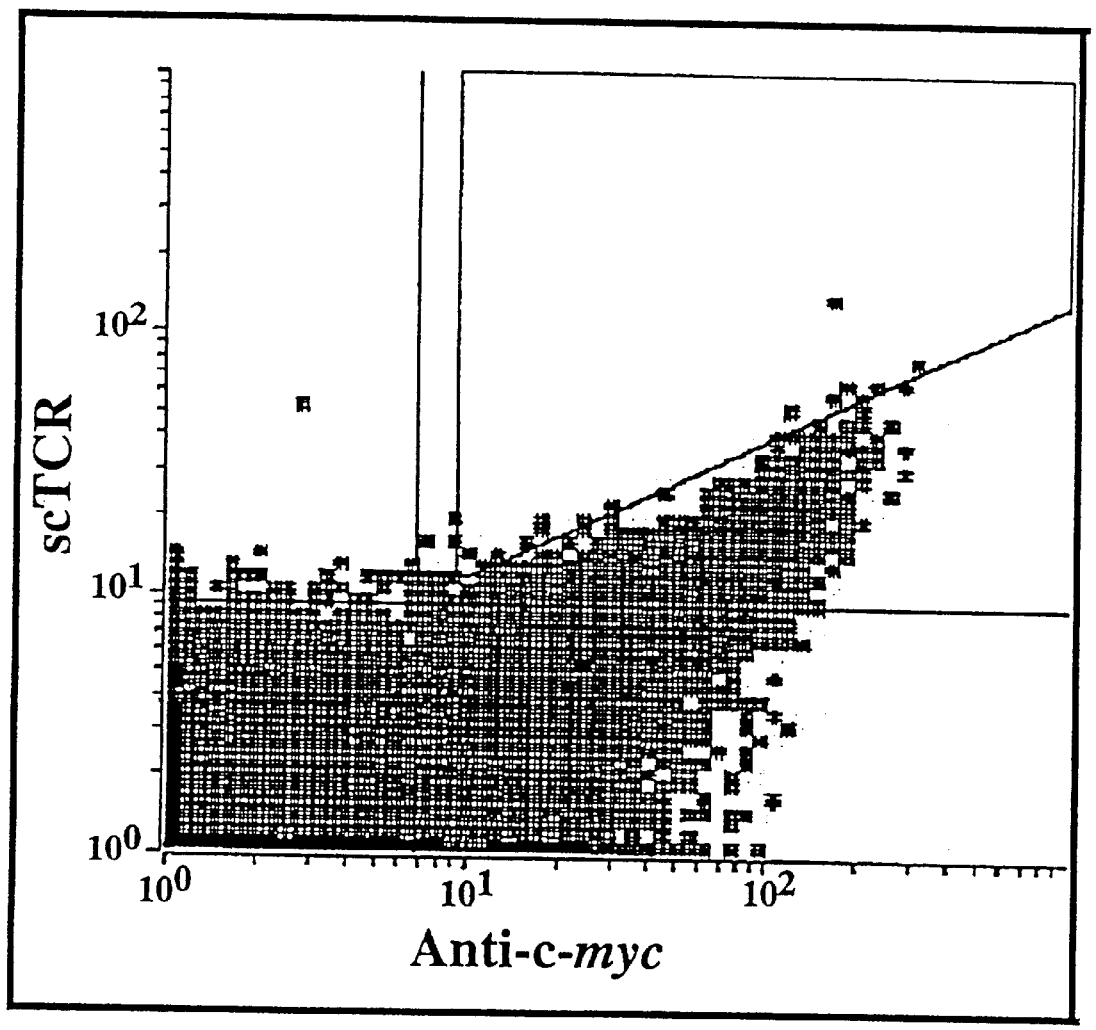
(FIG. 14A) Representative histogram from the first round of cell sorting, with the sorting window indicated, and (FIG. 14B) representative histogram from the fourth (final) round of sorting, illustrating an enrichment of the population in the sorting window.
Figure 14B:
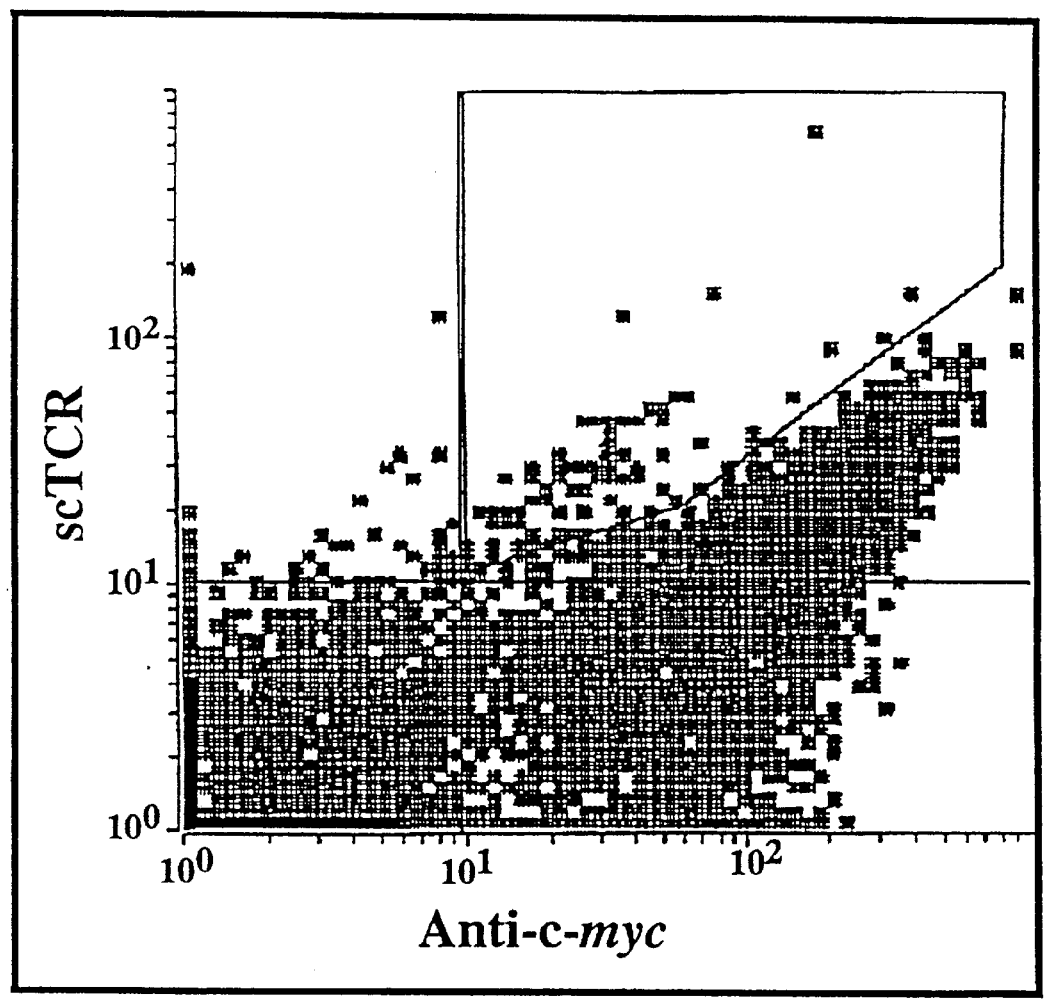
FIG. 14 (Parts A–B) shows the two dimensional fluorescence histograms and sorting window used to select scFv-KJ16 mutants. scFv-KJ16 cloned into the display vector pCT202 was transformed into the E. coli mutator strain XL1-Red (Stratagene) and propagated for six overnight growth cycles. Plasmids of the mutant library were purified and used in LiAc transformation (Gietz et al., 1995) of EBY100 yeast. After induction at 30° C., yeast were sorted using a fluorescence-activated cell sorter.

The mutagenized yeast library was subjected to four successive cycles of sorting and amplification, using a double stain for anti-c-myc antibody binding (FITC) and biotinylated-scTCR binding (PE). Biotinylated TCR was used at a 1:5000 dilution (~10 nM) that yielded just below the detectable threshold of binding by wt scFv-KJ16/yeast (FIG. 13). The two channel fluorescence profiles of the mutated scFv-KJ16 sample after one sorting cycle (FIG. 14A) and after four sorting cycles (FIG. 4B) are shown. Cells that exhibited fluorescence above the diagonal window shown in FIG. 14 were collected for regrowth. The rationale for this diagonal window was that in any given round the sort criteria were based on antigen binding per displayed polypeptide fusion. For example, selection based only on higher PE fluorescence levels (i.e. scTCR binding) would include not only those mutants with higher affinity scFv, but those that display a higher density of scFv per yeast cell. The latter mutants would in principle be eliminated by including the anti-c-myc antibody as one of the two parameters to normalize for surface expression variability. The first two sorting rounds were performed in enrichment mode, isolating the ~0.5% of the cell population with the highest fluorescence and not setting the sort software to reject coincidences (two cells in the same sorted droplet). The final two sorting rounds were performed for purity, with high coincidence rejection. After the fourth cycle, cells were resorted immediately and plated. Ten colonies (mut1-10) were selected for further analysis.

EXAMPLE 31
Characterization of Mutant scFv-Yeast

Figure 15:
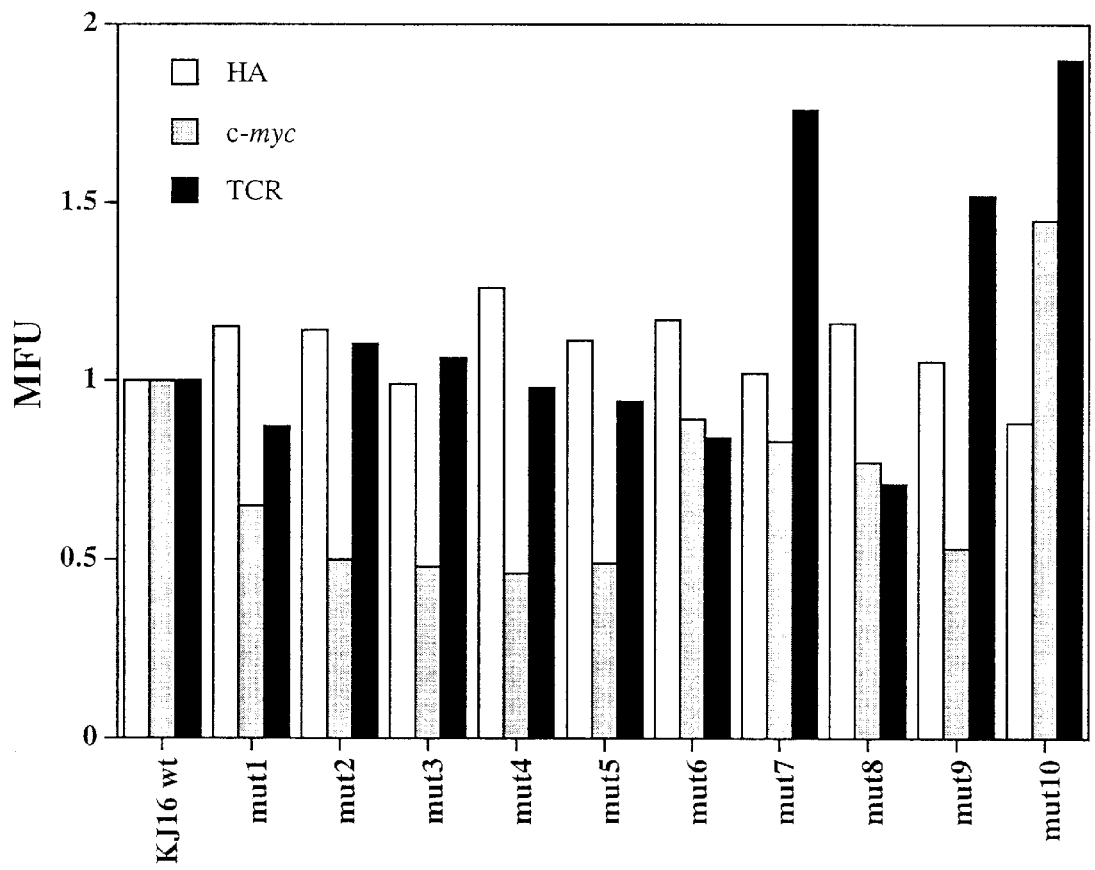
FIG. 15 shows the mean levels of binding to anti-HA Mab, anti-c-myc Mab, or biotinylated-scTCR for ten randomly selected clones from the final sort shown in FIG. 14B. Ten mutants and wt scFv-KJ16/yeast were induced in galactose medium at 30° C. overnight. Cells were analyzed by flow cytometry after staining with mouse anti-HA Mab followed by FITC-labeled goat anti-mouse IgG (open bars), mouse anti-c-myc followed by FITC-labeled goat anti-mouse IgG (gray bars), or biotinylated-scTCR at ~40 nM followed by a streptavidin-phycoerythrin conjugate (black bars).

Each of the 10 selected mutants were labeled with anti-HA antibody, anti-c-myc antibody, and biotinylated-TCR and was analyzed by flow cytometry (FIG. 15). As might be expected, one clone (mut6) appeared phenotypically similar to wt scFv-KJ16/yeast. Another clone (mut7) was found to exhibit higher TCR binding levels, a result confirmed by several independent titrations. Finally, a number of the mutants (mut1-5, 8, 9) consistently showed reduced binding to the anti-c-myc antibody compared to binding of the anti-HA antibody or the biotinylated scTCR. The presence of this class of mutants could be explained by the diagonal sort window specification: as shown in FIG. 14, cells can "move" into the sort window either by increasing scTCR (PE) binding at constant c-myc (FITC) signal, or alternatively by decreasing c-myc (FITC) binding at constant scTCR (PE) signal. The selection of these mutants could be easily circumvented by using both epitope tags in the fusion, HA and c-myc. Thus, by alternating labeling of each of these epitope tags in each round of sorting, diminished binding to one of the epitope tags would not be enriched in consecutive sorting rounds as in this case.

Fluorescence histograms of the presumptive c-myc epitope mutant (mut4), the scTCR binding mutant (mut7) and another mutant (mut10) were compared with the wt scFv (FIG. 16). Mut4 (FIGS. 16A and 16B) showed a reduction in anti-c-myc labeling, mut7 showed enhanced scTCR binding (FIGS. 16C and 16D), and mut10 did not show a shift in either, but the fraction of cells that were positive was higher than with the wt scFv (FIGS. 16E and 16F). As shown in FIGS. 16E and 16F, close to 100% of mut10 cells were positive for each of the agents tested. This contrasts with each of the other mutants (e.g. see mut4 and mut7) which resembled the wt scFv-KJ16 yeast in exhibiting two distinct populations of cells, one with reduced levels of cell surface scFv. Enhanced plasmid stability of mut10 and repeated failures to rescue the expression plasmid from mut10 into *E. coli* suggest that chromosomal integration has occurred with this mutant plasmid. Thus, the altered surface expression characteristics of mut10 appear to be a consequence of integration of the expression plasmid.

Figure 17:
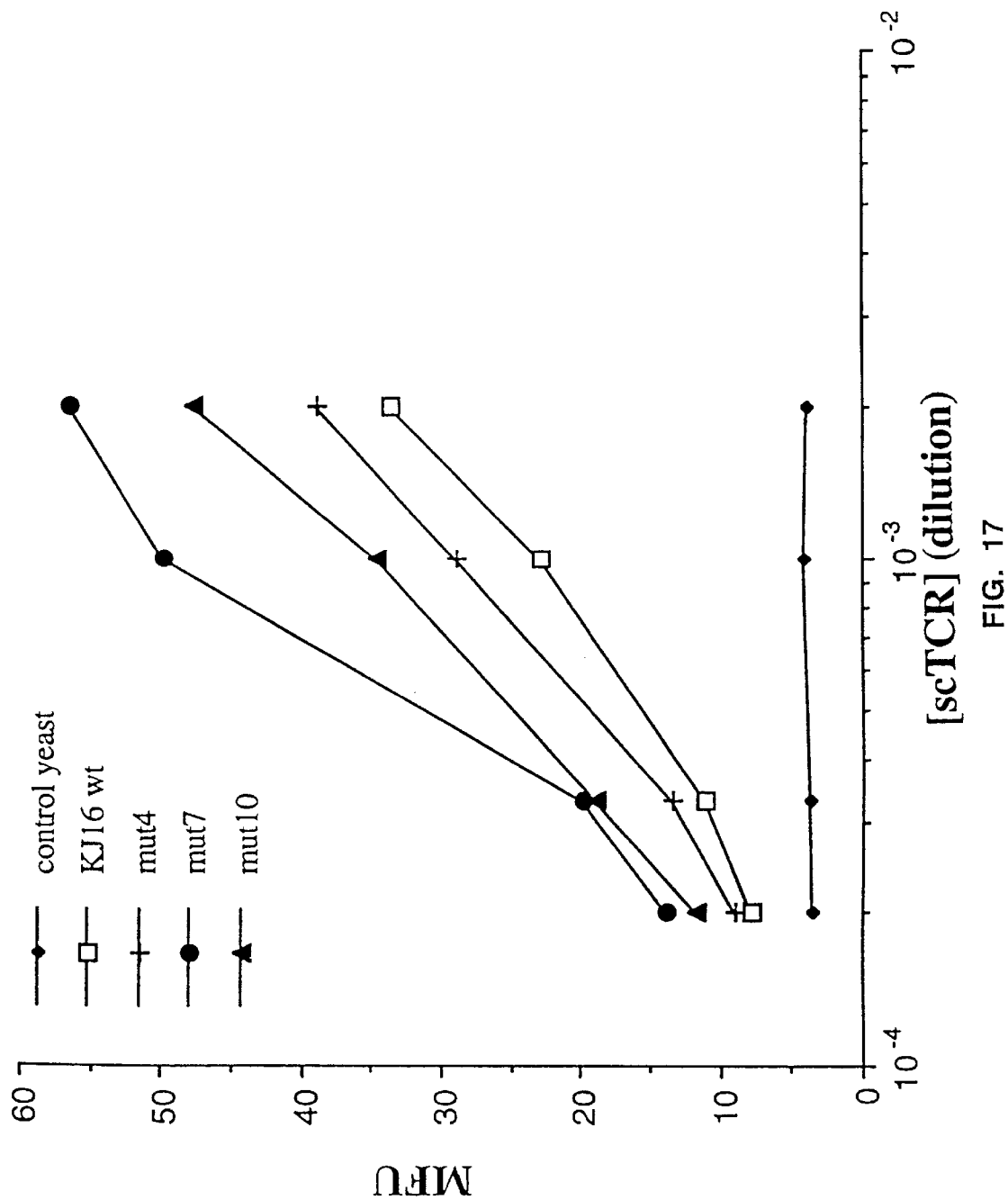
FIG. 17 shows the equilibrium antigen binding isotherms for three mutants shown in FIG. 16. Aga2p/HA/yeast, wt scFv-KJ16/yeast, and three mutant scFv-KJ16/yeast characterized in FIG. 16 were stained with various dilutions of biotinylated-scTCR followed by a streptavidin-phycoerythrin conjugate. After analysis by flow cytometry, binding isotherms were graphed with MFU as a function of scTCR dilution.

Binding affinity to scTCR was estimated for the mutants shown in FIG. 16 by titration with soluble biotinylated scTCR (FIG. 17). Nonlinear curve fitting of this data indicate unaltered $K_D$ for mut4 and mut10, but a threefold increased affinity for mut7. The increase in mean fluorescence of mut10 is due to the absence of a nonfluorescent tail in the distribution rather than increased scTCR binding, as is evident in FIGS. 16E and 16F.

EXAMPLE 32
Sequences of Mutant scFv

The nucleotide sequences of the wt-scFv-KJ16 cloned into the yeast display plasmid, and mut4 and mut7 following rescue of the plasmids from yeast was determined (FIG. 18) (SEQ ID Nos. 22–24). The wt scFv–KJ16 contained two silent changes from the originally published scFv sequence (Cho et al., 1995). These may have been introduced by PCR prior to cloning of the scFv into the yeast display plasmid. The mut4 sequence contained one mutation and mut7 contained two mutations. The only mutation in mut4 was present in the c-myc epitope (Lys to Glu), consistent with its reduced binding by anti-c-myc antibody as described above. Mut7 contained a change from Arg to Lys in a framework region of the $V_L$ region and a change from Ser to Arg in CDR1 of the $V_L$ chain. The latter mutation is consistent with the higher binding affinity observed for mut7.

Discussion

Phage display has been used for the selection of scFv with higher antigen binding affinity, as well as isolation of new scFv's from naive libraries (Hoogenboom, 1997). However, there have been difficulties in the expression of some mammalian proteins in *E. coli*, in part because of toxicity, codon bias, or folding problems (e.g. Knappik & Pluckthun, 1995, Ulrich et al., 1995, Walker & Gilbert, 1994). Yeast expression can potentially obviate some of these problems, by offering the advantage that proteins can be expressed with eucaryotic post-translational modifications (e.g., glycosylation and efficient disulfide isomerization). Furthermore, phage display does not generally possess the quantitative precision to discriminate between mutants with binding affinity differing by less than five-fold (Kretzschmar et al., 1995). By contrast, fluorescence labeling and sorting allowed the isolation of 4-4-20 scFv clones with only 3 fold increased affinity. Since most large changes in antigen binding affinity result from directed combination of point mutations, each with smaller effects (Hawkins et al., 1993, Schier et al., 1996, Yang et al., 1995), the capability to identify subtle improvements in affinity could be of significant value. With these advantages in mind, the use of a yeast display system for the affinity maturation of an anti-T cell receptor scFv was developed.

A scFv that is specific for the Vb8 region of a mouse TCR was used in order to generate anti-TCR reagents that may ultimately have enhanced T cell targeting properties in vivo (Cho et al., 1997, Cho et al., 1995). The active scFv was expressed as an Aga2p fusion protein on the surface of yeast, with an affinity that was similar to the native scFv (~500 nM compared to 120 nM for the scFv). To select higher affinity scFv, random mutagenesis with a DNA-repair deficient strain of *E. coli* yielded a mutation frequency of ~-2 to 3 per 1000 base pairs after six growth cycles. Flow cytometry with fluorescently labeled scTCR and anti-c-myc antibodies was used to sort cells displaying scFv's with increased scTCR affinity. The anti-c-myc antibody was included as a second criteria for selection to control for mutants with increased TCR binding due not to higher affinity but because of higher cell surface expression of the scFv-c-myc fusion. After multiple rounds of selection, three mutant phenotypic classes were observed: 1) reduced binding to the c-myc antibody but unaltered scTCR binding (mutl-5, 8, 9); 2) enhanced binding to the scTCR with unaltered c-myc labeling (mut7); and 3) higher efficiency surface expression due to chromosomal vector integration (mut10).

The isolation of classes of mutants that are represented by mut4 and mut7 could be predicted from the selection criteria illustrated in FIG. 14. That is, any mutant cell that was identified above the diagonal sort window boundary could be accounted for by either of the properties described for mut4 and mut7, since either an increase in scTCR (PE) signal or a decrease in c-myc (FITC) signal places a cell in the sorting window. This does not represent a substantial problem for this approach, however, because of the availability of two independent epitope tags. By utilizing the HA and c-myc tags in alternating sorting cycles, progressive enrichment for diminished labeling of one of the epitope tags should not occur.

The isolation of epitope tag mutants highlights an additional application for yeast surface display: mapping of epitopes recognized by monoclonal antibodies. Although alternative strategies that use peptide libraries have been successful in this regard for linear epitopes (Daniels & Lane, 1996), the approach described here can be extended to conformational epitopes. Accordingly, a properly folded protein can be displayed on the yeast cell surface and straightforward random mutagenesis as described herein can be applied to identify epitope residues from non-contiguous polypeptide sequence. Since nonfolded proteins are retained and degraded by the eucaryotic secretory quality control apparatus and varied expression levels are identified by HA or c-myc labeling, false identification of epitope residues should be minimized by this procedure. The described approach is substantially easier than alanine scanning mutagenesis.

It is not clear why mut10 was enriched in this screen, since its average single chain T cell receptor labeling per c-myc labeling was unaltered. It is possible that the higher fraction of positively labeled cells biased this clone for enrichment due to random spillover into the sort window. In any case, neither scTCR or c-myc labeling were different for this clone, and structural rearrangements of the expression plasmid indicate that it had integrated into a chromosome.

The identification of a single unique CDR mutation in mut7 is consistent with the finding that this mutant scFv has enhanced binding to the T cell receptor. Future efforts to obtain only scFv with higher affinity for the T cell receptor (and not c-myc mutants) involves alternate selection with anti-HA and anti-c-myc antibodies to control for cell surface levels of the scFv. This strategy, combined with DNA shuffling techniques among selected mutants (Stemmer, 1994), should allow the isolation of scFv-KJ16 with considerably higher affinity than the wt scFv ($K_D$~120 nM). Such mutant KJ16 scFv's can be used to test T cell signaling kinetic phenomena, as well as targeting of T cell-mediated killing via bispecific antibodies (Cho et al., 1997, Rabinowitz et al., 1996).

The present invention demonstrates the purposeful isolation of affinity matured antibodies via cell surface display. As described above, off-rate selection was employed to identify mutants with decreased dissociation rates, whereas in the expression of scFv-KJ16, equilibrated antigen binding was used. These two approaches are complementary, and depend on the affinity of the starting scFv. For $K_D$>1 nM, it is reasonable to pursue the strategy of equilibration with soluble labeled antigen as dissociation rates would be too rapid to allow effective discrimination of kinetic variation. Furthermore, at these lower affinities bulk soluble antigen is not substantially depleted from the labeling reaction mix, given that displayed scFv is present at effective concentrations of approximately 1–10 nM. By contrast, tightly binding antibodies such as 4-4-20 ($K_D$=0.4 nM) would deplete soluble labeled antigens at concentrations below $K_D$ unless inconveniently large labeling volumes were employed. However, dissociation kinetics for such tightly binding antibodies are slow enough to enable quenching, sorting, and analysis via manual mixing procedures. Thus, one could employ a strategy whereby scFv's would be affinity matured via cycles of equilibrium-based screening and mutagenesis to reach $K_D$~1 nM, followed by cycles of off-rate screening and mutagenesis to obtain still further improvement.

Cell surface display and flow cytometric screening allows selection of clones from a library based on kinetic binding parameters such as $K_D$ and the dissociation rate constant ($k_{diss}$). Binding parameters of selected mutants may then be quantitatively estimated in situ in the display format without a need for subcloning or soluble expression, as shown in FIG. 17. By contrast, selection of phage displayed antibodies often involves increasingly stringent wash and elution conditions, even to the extent of pH 2 and 8 M GuHCl. Such stringency selection has poor quantitative precision and may not always relate directly to binding parameters such as $K_D$ or $k_{diss}$ under ambient or physiological conditions.

Bacterial cell surface display systems have been described (Gunneriusson et al., 1996) for engineering of antibodies and other proteins. These systems possess some of the advantages of the present yeast display system, although they do not provide the post-translational processing capabilities of the eucaryotic secretory pathway. Access of macromolecules to the displayed protein on bacteria may also be restricted by the diffusion barrier presented by the lipopolysaccharide layer (Roberts, 1996). For this reason, binding to soluble protein antigens or epitope tag labeling with monoclonal antibodies is not possible. Surface display systems in cultured mammalian cells are also available (Rode et al., 1996), but construction and screening of combinatorial libraries for these systems are not as rapid or as versatile as for yeast.

A fairly small library ($3\times10^5$) was screened to isolate the mutants described herein. This does not represent an upper limit on yeast library size. Yeast libraries with $10^7$ clones have been constructed and further increases in library size, if necessary, would be attainable. The present invention shows that yeast surface display can be used to isolate a mutant scFv with increased affinity and that mutants with altered mAb epitopes can be enriched or excluded as desired. Further, the $K_D$ can be estimated in situ in the display format without necessitating subcloning and soluble expression. Quantitative optimization of the screening conditions will enable further improvements in this method. Applications of yeast surface display extend beyond antibody affinity maturation, to the isolation of binding domains from cDNA expression libraries, or isolation of mutant receptors or ligands on the direct basis of kinetic and equilibrium binding parameters.

EXAMPLE 33

Displayability and Expression of the T Cell Receptor in the Yeast Display System The present invention is also directed to a new process for engineering the T cell receptor for improved binding properties, e.g., to peptide-MHC complexes or superantigens. This invention establishes a method for displaying a T cell receptor in a yeast surface display library format. This method can be used: 1) in general, to express polypeptides that are not normally expressed on the surface or yeast, and 2) more specifically, to engineer higher affinity T cell receptors for a ligand of choice.

Protein engineering has not reached a level of development that allows rational and directed engineering of increased affinity binding. As a result, approaches have been developed that identify improved mutants from large mutant populations. The most widely used approach is "phage display", which has used to engineer antibodies, especially in the form of linked, "single-chain" antibodies. However phage display methodology has been unable to display single-chain T cell receptors (scTCRs) successfully. This is most likely because folding of isolated single-chain T cell receptors is very inefficient in the absence of the other components of the CD3 complex and the protein folding machinery of the eucaryotic endoplasmic reticulum; the bacterial periplasm is unable to effectively fold these fragments.

Figure 19:
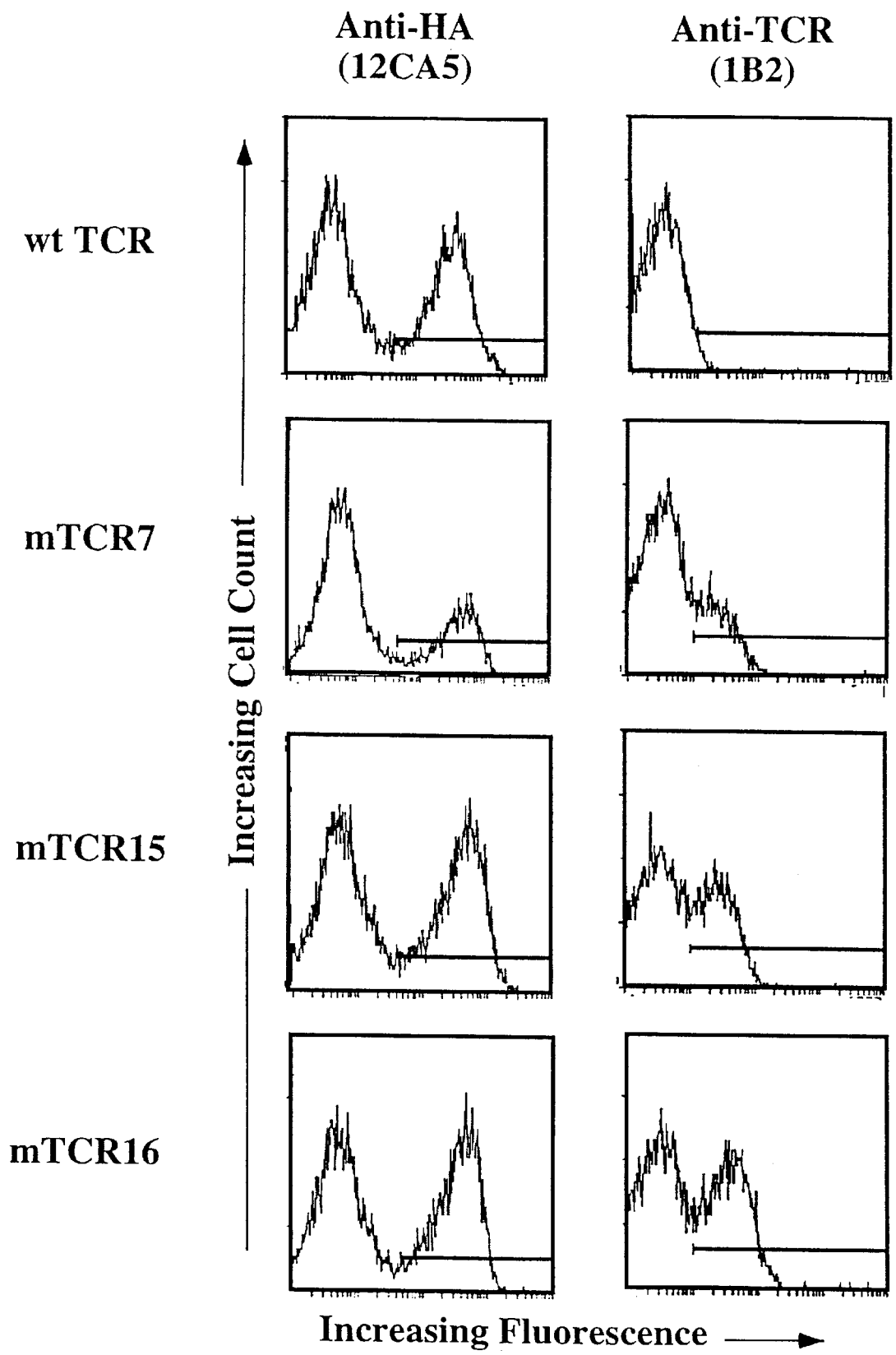
FIG. 19 shows the flow cytometry profiles of antibody binding to yeast that have been transformed with a plasmid that contains a T cell receptor single-chain (VαVβ) gene. The normal or wild type (wt) sequence is compared with several mutants (mTCR7, mTCR15, mTCR16) that were selected after random mutagenesis of the scTCR plasmid. Selection involved binding of the antibody 1B2, which recognizes a conformational epitope on the T cell receptor, followed by several round of fluorescent-activated cell sorting. In the first panel, the yeast cells were stained with an antibody (12CA5) to the HA tag. In the second panel, the yeast cells were stained with an antibody (1B2) to the T cell receptor. Although the HA epitope is expressed on the surface in each case, only those cells that express a mutagenized plasmid are capable of expressing the native T cell receptor (1B2 positive).
Figure 20:
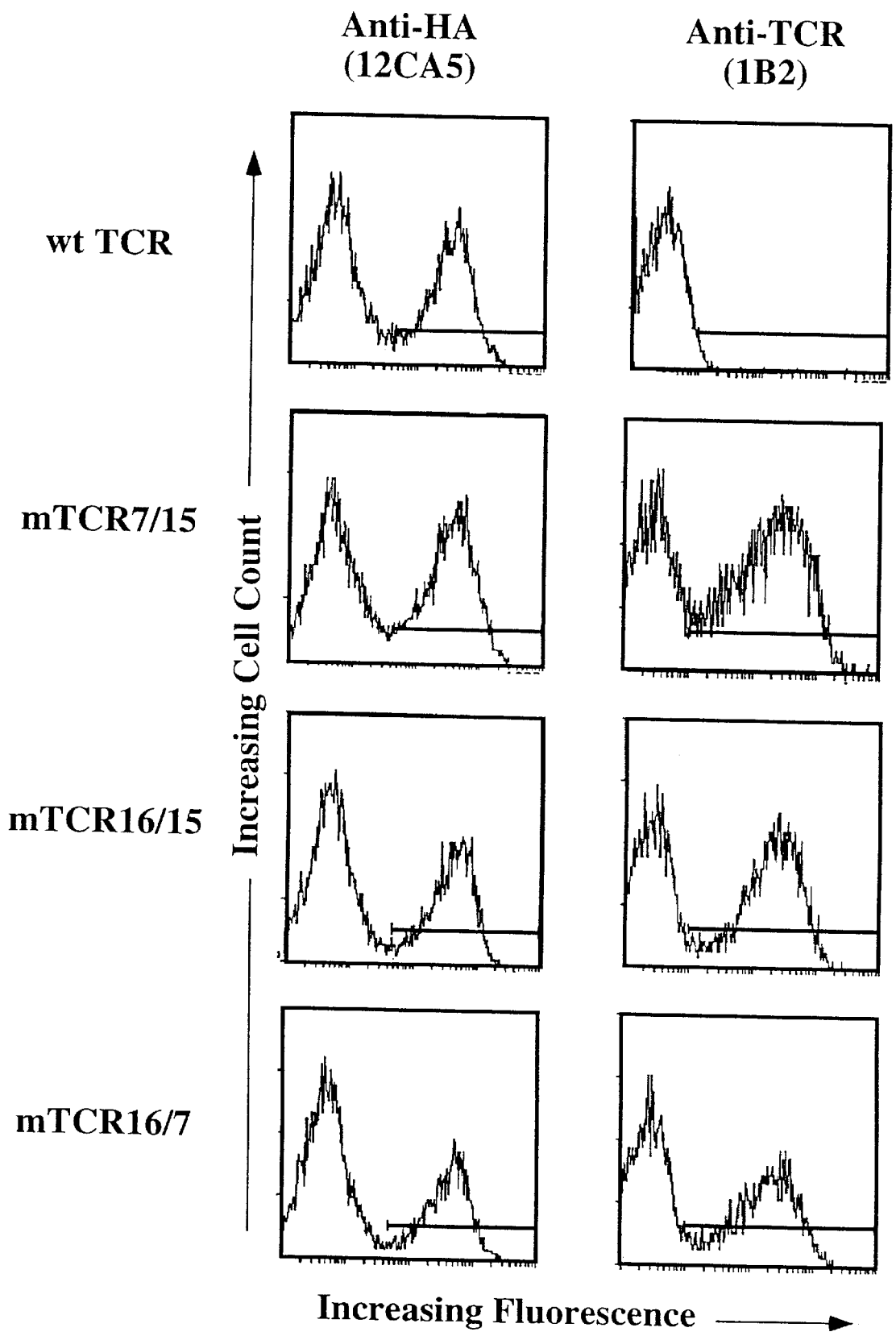
FIG. 20 shows the flow cytometry profiles of antibody binding to yeast that have been transformed with double mutants from the selection shown in FIG. 19. Cells were stained for flow cytometry as described in FIG. 19. Double mutants expressed an increase in level of the T cell receptor (i.e. 1B2-reactive material). The results show that by combining single mutations it is possible to enhance the level of cell surface expression of the T cell receptor.

The establishment of a yeast surface displayed T cell receptor is illustrated in FIGS. 19 through 21 (SEQ ID No. 25). A key improvement has been to isolate a mutant T cell receptor which can be displayed in this system. The wild-type T cell receptor is not functionally displayed, as shown by the absence of binding by an antibody (1B2) that is specific for the native conformation of the T cell receptor (FIG. 19). By mutating the T cell receptor and screening a library for 1B2 binding, a mutant single chain T cell receptor displayed in yeast was identified. This establishes a system which can now be used to isolate mutant single chain T cell receptors with improved binding properties.

The present invention provides a yeast cell-surface display system successful in expressing the T cell receptor. Second, expression of the full length T cell receptor could only be achieved after randomly mutagenizing the T cell receptor gene and then selecting by flow cytometry for surface expression. This method thereby exploited an evolutionary approach to "correcting" the expression defect in the T cell receptor.

This same approach could be applied to any polypeptide which in its wild-type form is not displayed efficiently. Selection for "displayability" has been reduced to practice for the T cell receptor, as described in examples 33–37. Once displayable mutant versions of the polypeptide are obtained, these versions can then be subjected to the screening processes for improved binding properties that are described in examples 1–32.

Improved T cell receptor molecules are useful in therapies for cancer, sepsis, and autoimmune diseases such as arthritis, diabetes, or multiple sclerosis. For example, soluble forms of high affinity T cell receptors would act as antagonists of detrimental T-cell mediated autoimmune diseases and thereby provide potential treatments for these diseases. Analogous strategies have been successfully employed with a soluble tumor necrosis factor receptor (TNF-R) and forms of this receptor are in clinical trials for septic shock and rheumatoid arthritis (Moosmayer et al., 1995).

In the methods of the present invention, yeast surface display allows single chain T cell receptors to be engineered to bind with high affinity to MHC-peptide complexes or superantigens. Such molecules would find a variety of medical uses. Examples include, but are not limited to: 1) interfering with inappropriate T cell attacks on healthy tissue in autoimmune diseases such as arthritis, diabetes, and multiple sclerosis; 2) interfering with septic shock due to bacterial superantigen that interact with T cells, leading to massive inflammatory reactions; and 3) destruction of tumor cells that bear T cell receptor ligands (e.g. specific tumor peptide/MHC complexes) by using high affinity T cell receptor together with anti-CD3 bispecific agents to redirect T cells to attack the cancerous cells.

Plasmids and Strains

The single-chain TCR gene (V(8.2-linker-V(3.1) gene joined by a modified 205 linker (Cho et al., 1995) was subcloned by PCR into the vector pCR-Script (Stratagene, La Jolla, Calif.) following the manufacturer's protocol. A 6-His epitope tag was included at the carboxy-terminus of the scTCR for purification purposes. The ~800-bp NheI/XhoI fragment containing the scTCR was excised from pCR-Script and ligated into the yeast surface display vector pCT202 containing a nine-residue epitope tag (HA) and the AGA2 open reading frame downstream of the inducible GAL1 promoter. The resultant construct was transformed by the lithium acetate (LiAc) transformation method of Gietz and Schiestl (Gietz et al., 1995) into the *S. cerevisiae* strain BJ5465 (aura3-52 trp1 leu2D1 his3D200 pep4::HIS2 prbD1.6 can1 GAL; Yeast Genetic Stock Center, Berkeley, Calif.) containing a chromosomally integrated AGA1 controlled by the GAL1 promoter (strain EBY100).

EXAMPLE 34
Production of an scTCR Random Mutant Library

Approximately 50 ng of pCT202/scTCR were transformed into *E. coli* XL1-Red cells (Stratagene, La Jolla, Calif.) according to the manufacturer's protocol. Following a 1 hour induction in SOC medium, the recovery was centrifuged at 2000 rpm for 5 min. and resuspended in 500 ml of liquid LB medium containing 100 mg/ml ampicillin plus 50 mg/ml carbenicillin (LB-AMP100-CARB50). The resuspension was added to 15-ml LB-AMP100-CARB50 in a 50-ml Erlenmeyer flask and grown at 37° C. with shaking. The culture was replenished with a fresh 15-ml LB-AMP100-CARB50 at mid-log phase ($OD_{600}$(0.2–0.4), then grown to saturation ($OD_{600}$~1.0–1.1; this was considered one "cycle" or round of mutation). A small fraction of this culture (0.75 ml) was added to the next cycle (15-ml LB-AMP100-CARB50). After six cycles of growth, Wizard® miniprep (Promega, Madison, Wis.) DNA plasmid preparations were performed on the 15-ml culture. Approximately 10 mg of pCT202/scTCR DNA from cycle six were transformed into each of 10 tubes of yeast strain EBY100 using the LiAc method. The 10 reactions were pooled after resuspension in 1-ml dd$H_2O$/tube, $\frac{1}{10,000}$ of the pool plated on selective plates to determine transformation efficiency. The library size was approximately $7 \times 10^6$. A 50 ml volume of SD-CAA (glucose 2 wt %, Difco yeast nitrogen base 0.67 wt %, casamino acids 0.5 wt %o) was inoculated with the remainder of the culture, grown overnight at 30° C. with shaking, passaged to $OD_{600}$=0.05, and grown overnight at 30° C. to $OD_{600}$>1.0. Five milliliters of selective galactose medium SG-CAA (where 2% galactose replaces the glucose in SD-CAA) were then inoculated to $OD_{600}$=0.5 and grown overnight at 20° C. with shaking for ~20–24 h (1–2 doublings).

EXAMPLE 35
Selection of scTCR Mutant Library by Fluorescence-Activated Cell Sorting Cells were labeled with 25 mL Mab 1B2 (anti-Vb8.2Va3.1; prepared from ascites fluid and conjugated to biotin) at a concentration of 20 mg/ml. Samples were sorted on a Coulter 753 bench with an event rate of ~4,000 cells/sec (Flow Cytometry Center, UIUC Biotechnology Center). A total of $6 \times 10^7$ cells were examined during the first sorting round, with ~5% of the population collected. The collected cells were regrown between sorts at 30° C. in 4 ml selective glucose medium SD-CAA. After ~18–20 hours, recombinant AGA1 +AGA2-scFv expression was induced at 20° C. with shaking in 5 ml SG-CAA. A total of 3 rounds of sorting was performed, with the first sort in enrichment mode (high recovery of all positive clones) and the last 2 sorts in purification mode (coincident negative cells rejected). Immediately following the last sort, the collected cells were re-sorted, collected as two separate populations ("high expression" and "low expression"), and plated on selective plates to isolate individual clones. Twenty clones were examined by flow cytometry.

EXAMPLE 36
Induction and Detection of Mutant scTCR on the Yeast Surface

Individual clones from the pCT202/scTCR library sorting were grown overnight at 30° C. with shaking in 3 ml SD-CAA followed by induction in SG-CAA as described above. Cultures were harvested after (20–24 hours (1–2 doublings) by centrifugation, washed with PBS (10 mM $NaPO_4$, 150 mM NaCl, pH 7.3) containing 0.1% bovine serum albumin and 0.05% azide, and incubated 45 minutes on ice with 25 (L of 10 mg/ml anti-HA Mab 12CA5 (Boehringer Mannheim, Indianapolis, Ind.), or biotinylated-1B2 Mab (20 mg/ml) prepared from ascites fluid. Cells were washed with PBS and incubated 30 minutes on ice with either FITC-labeled F(ab')$_2$ goat anti-mouse IgG (1:50; Kirkegaard and Perry Labs, Inc., Gaithersburg, Md.) or a streptavidin-phycoerythrin (SA-PE) conjugate (1:100; PharMingen, San Diego, Calif.). Labeled yeast cells were analyzed on a Coulter Epics XL flow cytometer. Event rate was ~250 cells/sec. Data for 10,000 events was collected, and the population was gated according to light scatter (size) to prevent analysis of cell clumps. Results from the wild type (wt) TCR and several representative TCR mutants are shown in FIG. 19. Double mutants containing the combined mutations from several of these isolates were also constructed and the results of flow cytometry of these are shown in FIG. 20.

EXAMPLE 37
Rescue and Sequencing of Mutant scTCR Genes

Plasmids from scTCR yeast (wt and 20 mutants) were rescued according to the protocol described by Ward (Ward, 1991), except that cells were disrupted with a bead beater (BioSpec Products, Inc., Bartlesville, Okla.) for 2 minutes instead of vortexing. Cells were centrifuged for 1 minute and the upper (aqueous) phase collected. A Wizard® DNA Clean-Up kit (Promega, Madison, Wis.) was used to prepare the plasmid DNA and *E. coli* DH5α ElectroMAX® competent cells (GibcoBRL, Gaithersburg, Md.) were transformed via electroporation with 1 ml of the DNA preparation. Transformations were plated on LB-AMP50. Sequencing of wt scTCR and 20 mutants (mTCR1-mTCR20) was performed using primers that flank the scTCR of the display vector and fluorescence automated sequencing (Genetic Engineering Facility of the UIUC Biotechnology Center). Single mutations were found in the TCR for each of the isolates shown (FIG. 21).

EXAMPLE 38
Surface Display and Soluble Expression of Single Double and Triple TCR Mutants The single-site mutants included the following residues: VaL43P (mTCR7), VaL104P (mTCR16), and VbG17E (mTCR15). Combination of these mutations into double or triple mutants yielded surface display of the scTCR at even higher levels.

Figure 22:
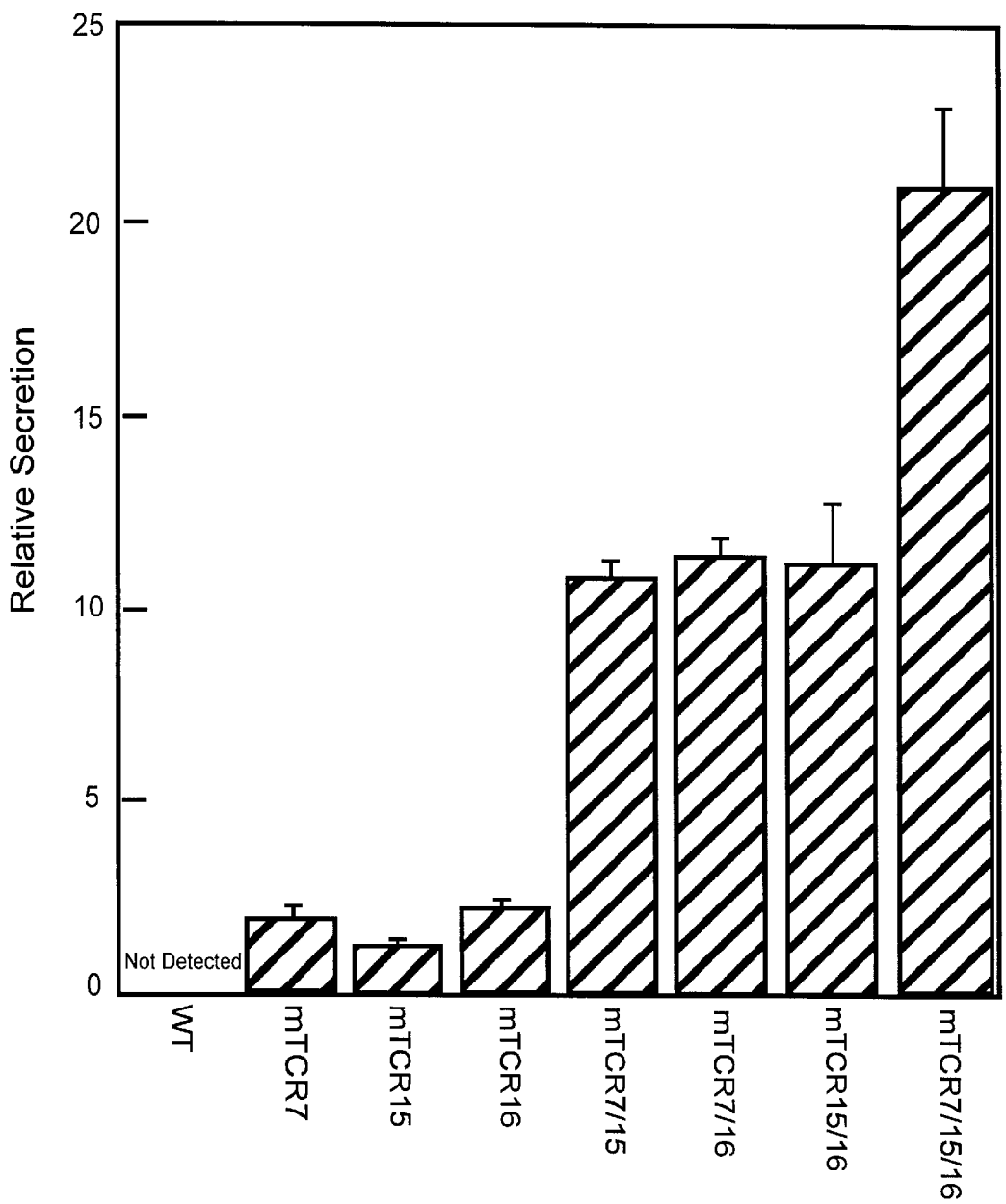
FIG. 22 shows relative secretion levels of scTCR. Soluble expression levels (arbitrary units) of scTCR produced using low copy yeast expression system. Triplicate cultures from independent clones were analyzed for 1B2 ELISA activity.

To examine the mutant scTCRs selected by the yeast surface display in more detail, the single (mTCR7, mTCR15, mTCR16), double (mTCR7/15, mTCR7/16, mTCR15/16) and triple (mTCR7/15/16) mutants were cloned into a yeast secretion plasmid, with a synthetic pre pro region based on a consensus signal sequence (Clements et al., 1991) under the control of the inducible GAL 1–10 promoter. The constructs were expressed in yeast and the resultant supernatants were monitored in a quantitative 1B2 binding assay as a measure of properly folded TCR protein. The expression levels of 1B2 active scTCR mutants varied from undetectable levels for the wild type scTCR to the triple mutant, that expressed the highest levels (FIG. 22). The order of secretion levels was: triple mutant >double mutants >single mutants >wild type. Selected scTCR double mutants were affinity purified using an anti-TCR antibody column (KJ16-Affigel) and the absolute secretion levels using the low copy expression system were found to be approximately 100 mg/L.

EXAMPLE 39
Comparison of TCR Secretion and Surface Display Levels

Figure 23A:
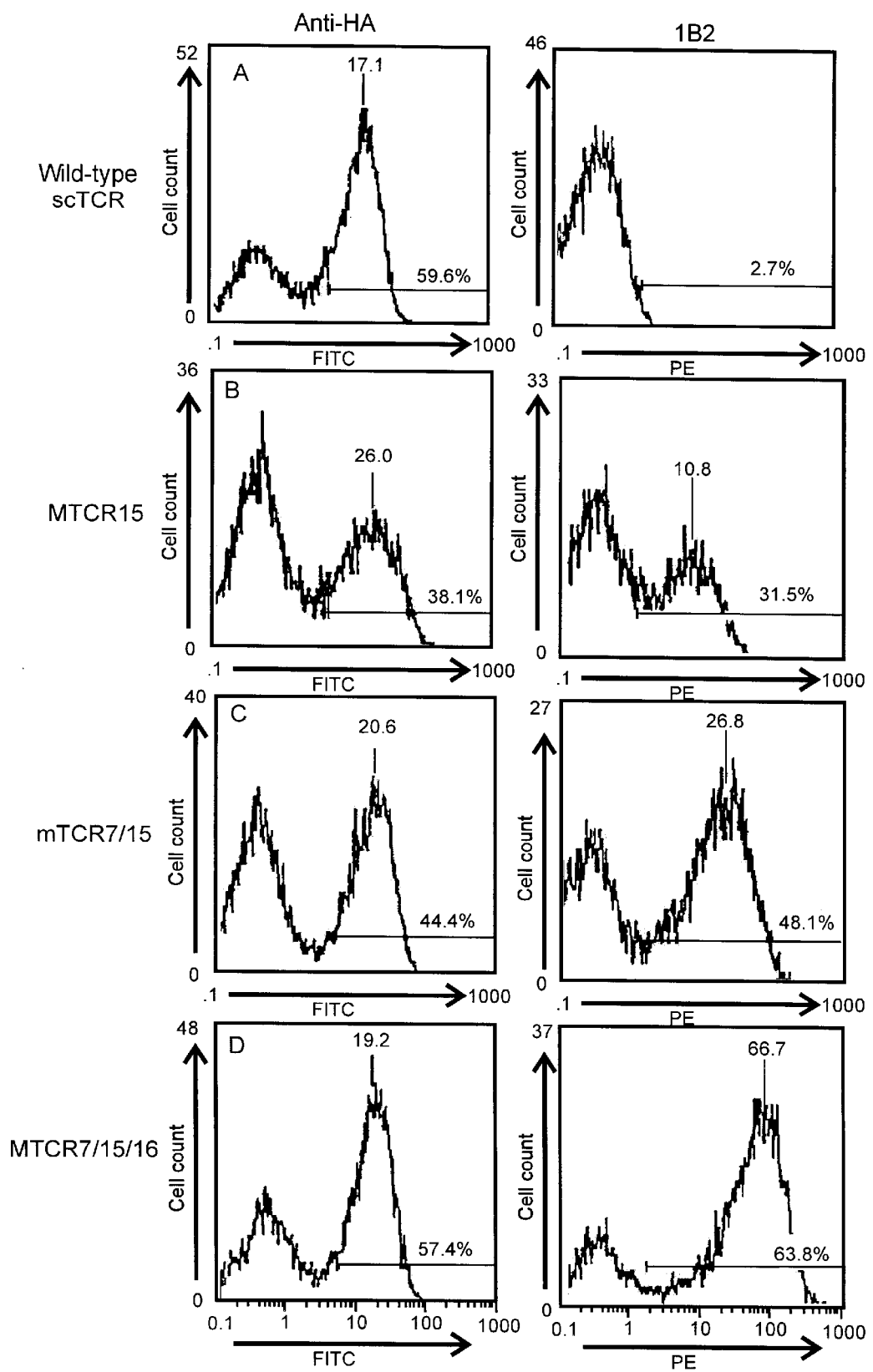
FIG. 23A shows flow histograms of scTCR displaying yeast. The cell sorted populations for wild-type and representative single, double, and triple mutants are presented. The mean fluorescence units (FITC fluorescence: anti-HA, PE fluorescence: 1B2) are indicated on each histogram. Anti-HA indicates number of surface fusions, and 1B2 indicates the number of cells displaying properly folded scTCR.
Figure 23B:
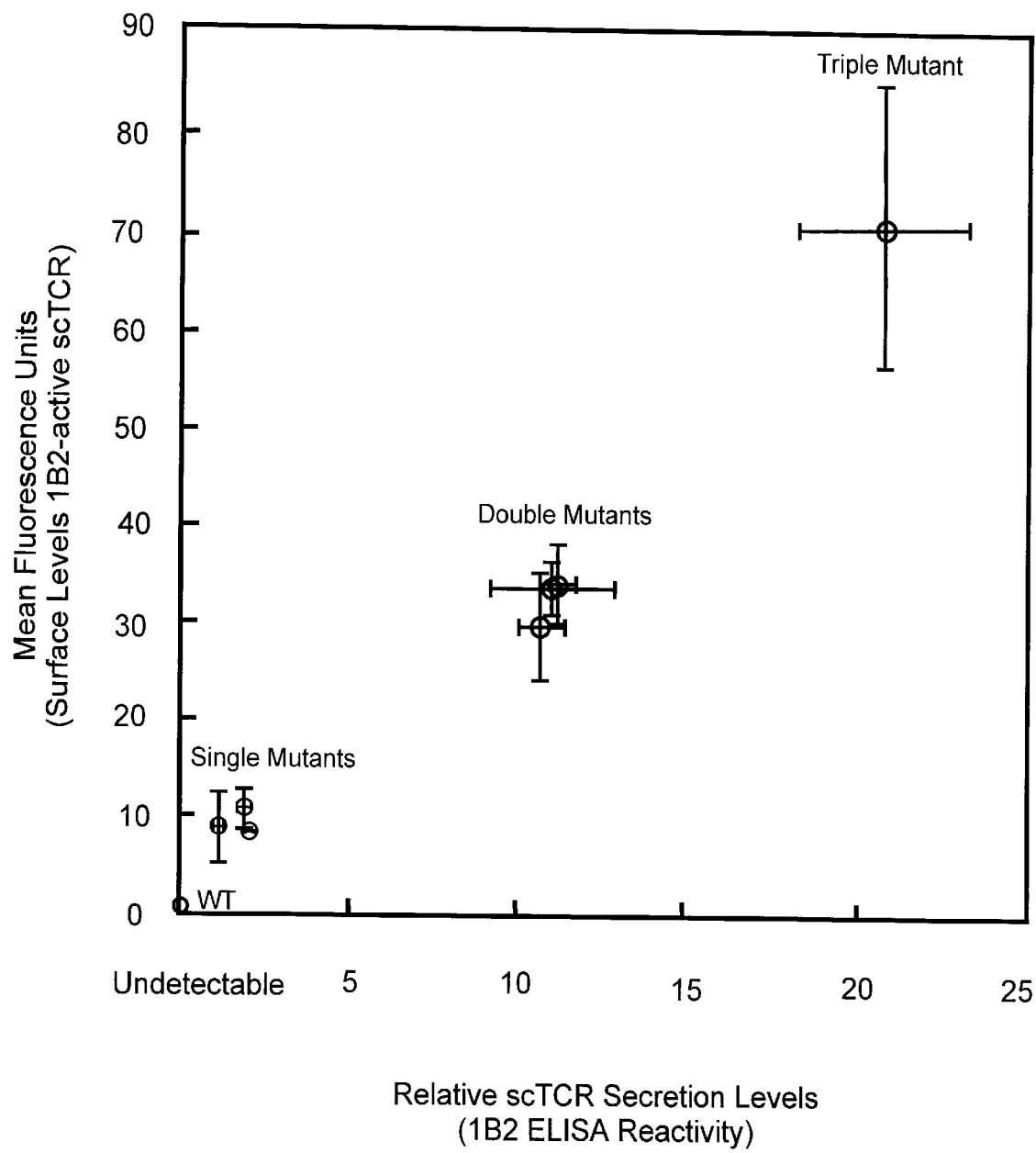
FIG. 23B shows the correlation between surface expression and soluble secretion. 1B2-active surface scTCR determined by flow is compared to 1B2 activity of soluble secreted material by ELISA assay. At minimum, duplicate flow experiments were done to determine the mean fluorescence units of a particular clone.

In order to directly compare the secreted levels of the scTCR in this system with the levels of TCR expressed in the surface display system, the same mutants were examined as Aga-2 fusions on yeast, using flow cytometry. The scTCR's displayed on the surface of yeast were labeled with the anti-HA antibody followed by a fluorescein-labeled secondary antibody and the biotinylated 1B2, followed by streptavidin-phycoerythrin. The resulting fluorescence intensity of the yeast populations were monitored by flow cytometry and determined as a mean fluorescence units (FIG. 23A). The level of fluorescence varied among the single, double and triple mutants, but the relative levels were exactly the same as with the yeast secretion system (FIG. 23B)(i.e. triple mutant >double mutants >single mutants >wild type). Thus, the yeast display system was capable of identifying those TCR mutants that would be produced in a secretable expression system at high levels, by simply selecting for those that were expressed at higher levels on the surface of yeast.

EXAMPLE 40
Thermal Stability of Soluble TCRs

Figure 24A:
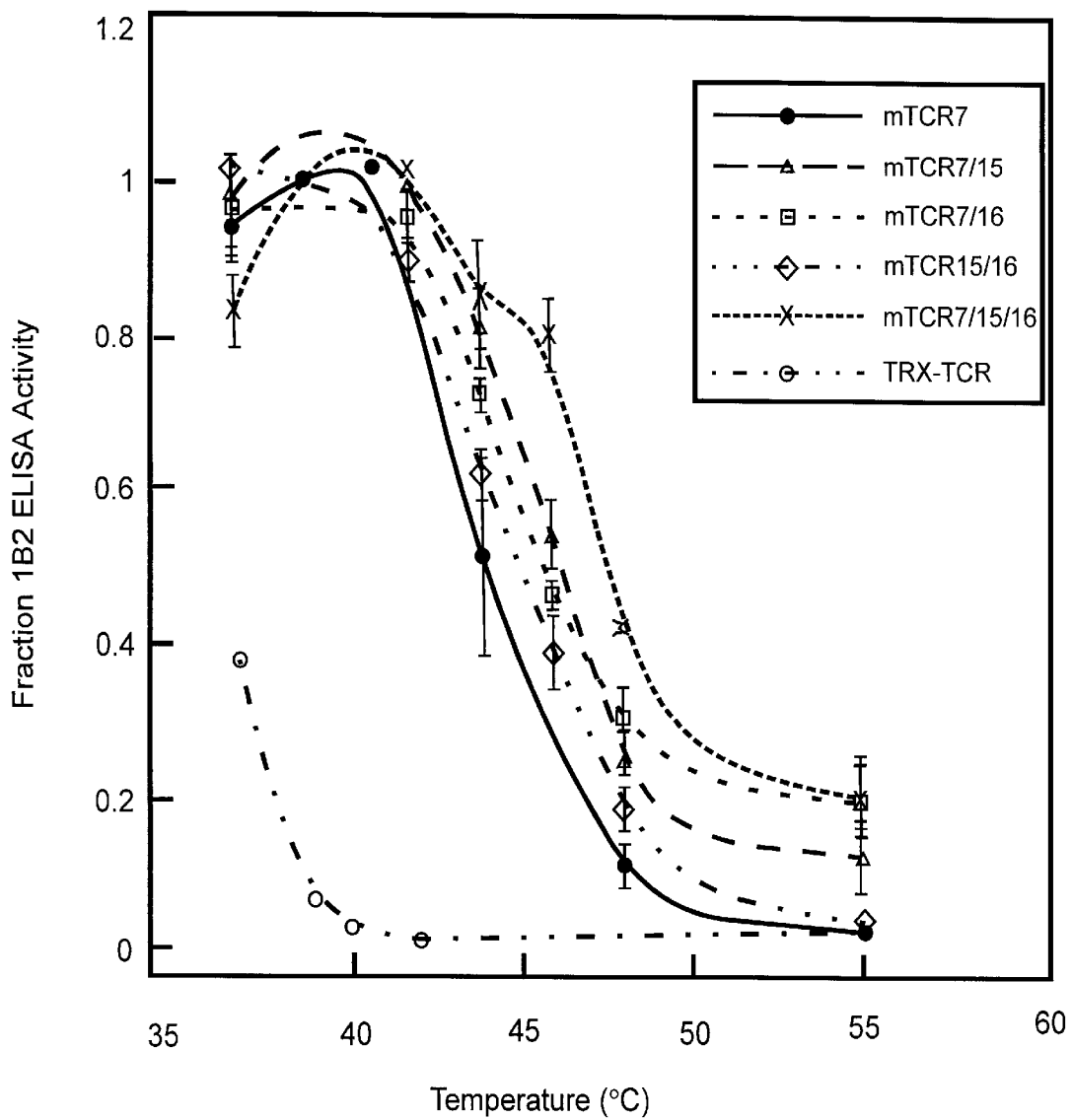
FIG. 24A shows the temperature stabilities of scTCR. Yeast supernatant samples containing scTCR were subjected to the indicated temperatures for one hour. Triplicate samples were analyzed for 1B2-active fractions by ELISA. The fractions were normalized independently to unity by the highest intensity ELISA signal having no activity loss.

In order to explore the protein property that might govern the secretion (and display) levels for the mutant scTCR's, the stability of mutant scTCR were investigated by performing thermal denaturation. Yeast scTCR supernatants were incubated at various temperatures for one hour and the protein activity monitored as a percent of 1B2 activity that remained. Because the wild-type scTCR was not expressed in the yeast system, a wild-type scTCR refolded from E. coli inclusion bodies was used for comparison. This scTCR was used as a thioredoxin fusion protein (TRX-TCR), which is predicted to increase the stability and solubility of a protein. The results showed that the single mutants had higher temperatures of thermal denaturation than the TRX-TCR (FIG. 24A). In addition, the double and triple mutants were even more stable, having even higher temeperatures of denaturation than either the wild type TCR or the single mutants (FIG. 24A).

Figure 24B:
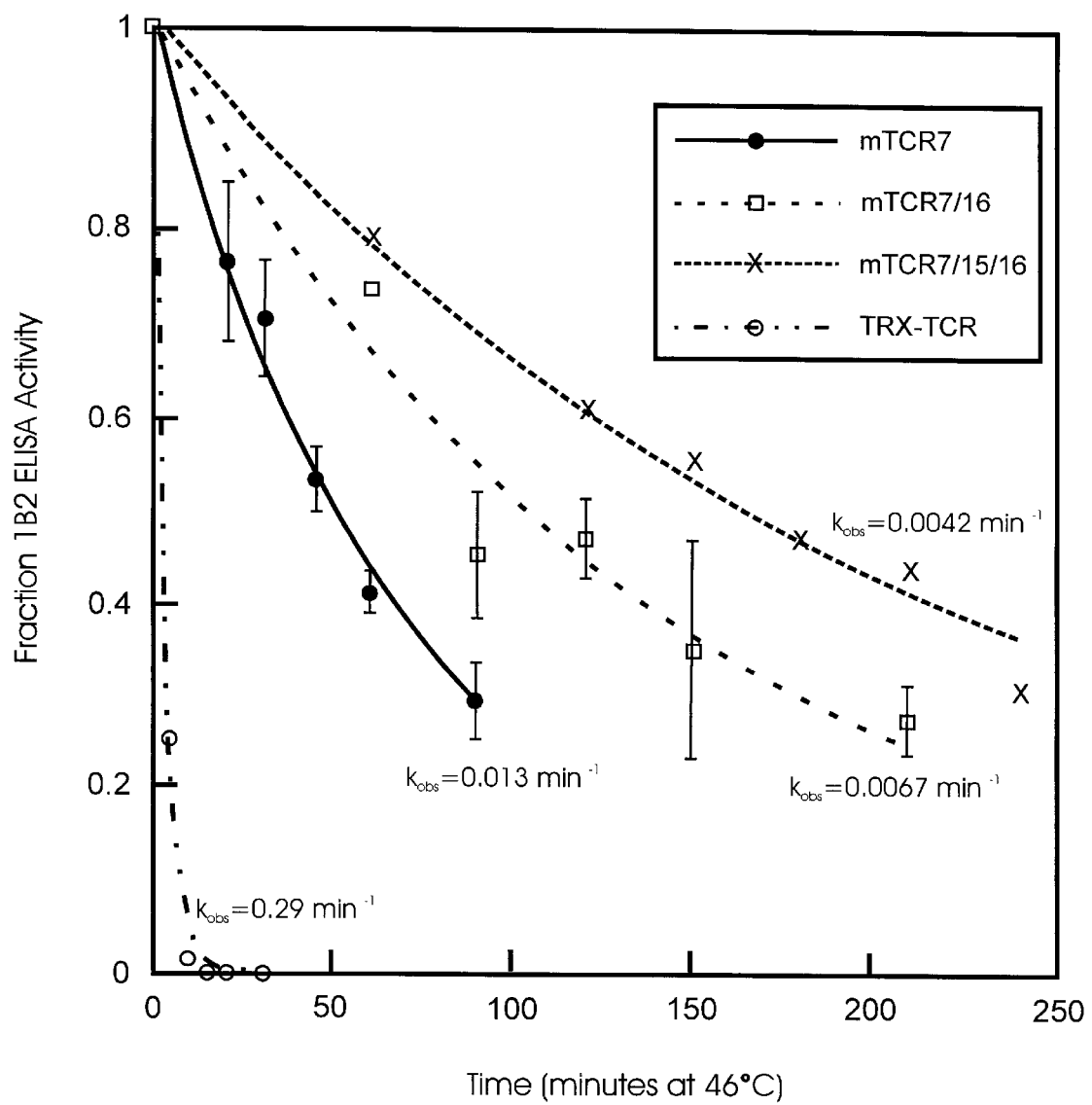
FIG. 24B shows the kinetics of scTCR thermal denaturation. 1B2 ELISA activity of supernatant samples was monitored as a function of the time each sample was incubated at 46° C. Observed kinetic thermal denaturation rates ($k_{obs}$) at 46° C. are indicated. In both FIGS. 24A and 24B, comparisons are made to TRX-TCR rather than wild-type scTCR because wild-type scTCR was not detected in yeast supernatants.

The kinetics of thermal denaturation for the mutant scTCR's were determined at 46° C. in order to compare the rates of denaturation with each mutant (FIG. 24B). Again, yeast scTCR supernatants and their 1B2 binding activity were monitored for TCR activity that remained after incubation for various times. The rate for thermal denaturation was highest for the TRX-TCR and lowest for the triple mutant, with the single and double mutants lying in the intermediate range (FIG. 24B). Affinity purified mTCR15/16 had similar thermal denaturation kinetics as that determined for mTCR15/16 measured directly in yeast culture supernatants. This indicates that endogenous yeast proteins present in supernatants did not affect the measured denaturation kinetics.

Figure 25:
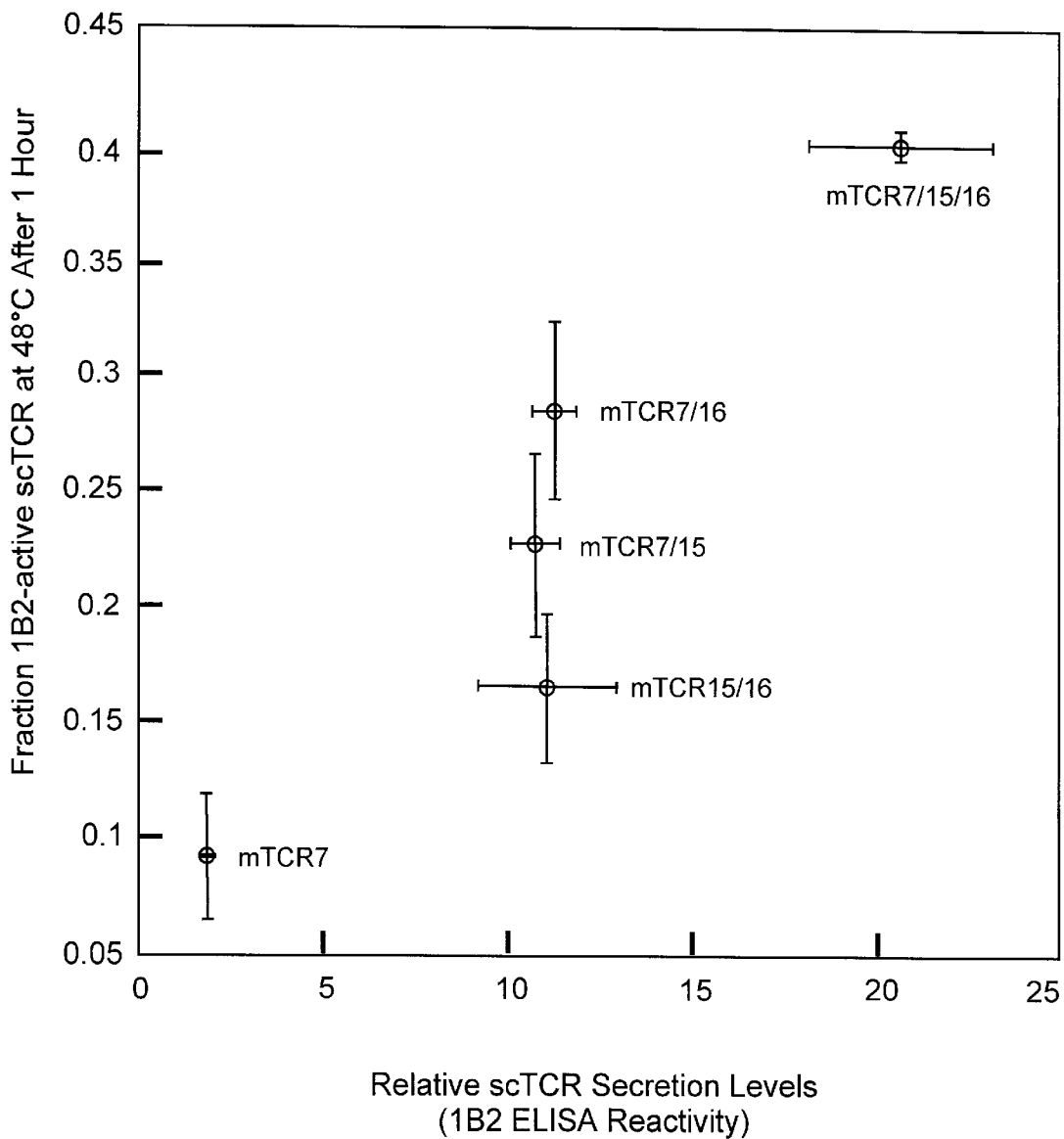
FIG. 25 shows the correlation between thermal stability and soluble expression. The scTCR 1B2 ELISA activity remaining after being incubated at 48° C. for one hour is compared to relative secretion levels (1B2 ELISA). Triplicate samples were analyzed for the secretion levels and for the thermal denaturation analyses.

A direct correlation was observed when the amounts of native TCR remaining after one hour at 48° C. were plotted against secretion levels for the mutant scTCRs (need FIG. 4 from Shusta et al. =FIG. 25). Thus, in the case of the TCR, the intrinsic property of stability was a reliable predictor of secretion efficiency and was directly correlated with yeast cell surface levels of the TCR. Because of this correlation, the display system can be used, by selecting for the higher surface levels of a protein, to isolate mutant proteins that exhibit increased stability.

EXAMPLE 41
Post-Translational Modification and Yeast Display

The methods of the present invention have identified variants of the 2C scTCR which are readily expressed in yeast and display significantly enhanced thermal stability. In fact, the single-site mutants identified converted what is normally an unstable scTCR into a scTCR that appears to be as stable as covalently, disulfide "stabilized" or chemically crosslinked single-chain antibody fragments (scFv). This is especially important for the TCR, which has potential as an antagonist in the treatment of autoimmune diseases. As heterologously expressed wild-type TCR has previously been very unstable, pharmacokinetics at physiological temperature will be important.

It has been shown that glycosylation can result in increased secretion and thermal stability of proteins. For example, glucoamylase was less stable as the non-glycosylated form produced in E. coli than the glycosylated form produced in the yeast S. cerevisiae. Therefore, it was possible that the stabilities of the scTCRs produced in yeast, which have one N-linked glycosylation site in the Vα region, would be greater than that of the non-glycosylated TRX-TCR produced in E. coli. However, this is unlikely to be the sole explanation, as the double and triple mutants have increased stability over the single mutants and both of these species are glycosylated. In addition, expression of the wild-type scTCR in yeast was not detected, even though it also would be expected to be glycosylated.

The expression levels of the various mutant scTCRs in the secretion system correlated completely with the level of TCR on the surface in the yeast display system. This relationship may arise from the fact that both systems require the same secretory apparatus. Accordingly, mutations that affect protein folding and stability can affect the same steps of protein transport to the outside (i.e. cell surface or secreted). This is a distinct advantage of expressing eukaryotic proteins in yeast (compared to bacteriophage or bacteria), as there are quality control mechanisms to ensure that only properly folded proteins traverse the entire exocytotic pathway.

Mutant scTCR expression levels also correlated with thermal denaturation rates. This effect is similar to those seen with bovine pancreatic trypsin inhibitor, in which mutations that resulted in increased stabilities also led to increases in secretion levels in yeast. This correlation supports the theory that a protein which has increased stability in folded form is more likely to be properly packaged and exported from the cell rather than being retained and degraded by the eukaryotic quality control machinery. Of course, many other factors such as forward folding rate, disulfide bond formation, and association with endoplastic reticulum protein folding assistants also play important roles. However, as this invention demonstrates, thermal stability appears to be a good measure of secretion competence for a previously unstable and poorly secreted molecule such as the TCR.

Based on the findings presented herein, one could envision a methodology through which a protein which is poorly expressed and/or unstable can be systematically evolved to express at higher levels and/or as a more stable molecule. The gene encoding the protein can be randomly mutated and the library expressed on the surface of yeast. Once displayed, the population can be screened for clones which exhibit high surface concentrations (high mean fluorescence due to a specific probe). As demonstrated with the scTCR, those variants with improved surface expression have the potential to be more stable molecules which express at high levels. Accordingly, yeast surface display can be a powerful tool for increasing the stability of proteins for crystallization, industrial, and medical applications.

The following references were cited herein:
Bassolino-Klimas, D., et al., Protein Science 1:1465–1476, 1992.
Baumgartner, J-D, et al., Immunobiol. 187:464–477,1993.
Berek, C., et al., ImmunoL Rev. 96:23–41, 1987.
Bird, R. E., et al., Science 242:423–426,1988.
Born, et al., (1987) J. Immunol. 138, 999.
Brodnicki, et al., (1996) Mol. Immunol. 33, 253–2631.
Brummell, D. A., et al., Biochemis. 32:1180–1187, 1993.
Cappellaro, C., et al., EMBO Journal 13:4737–4744, 1994.
Chang et al., (1994) PNAS USA 91:11408–11412.
Cho, et al., (1997) Bioconj. Chem. 8, 338–346.
Cho, et al., (1995) J. Biol. Chem. 270, 25819–25826.
Choo, Y., & Klug, A. (1995) Curr. Opin. Biotechnol. 6, 431–436.
Clackson, T., et al., Nature 352:624–628, 1991.
Clements, et al., (1991) Gene 106:267–271.
Daniels, D. A., & Lane, D. P. (1996) Methods 9, 494–507.
Davis, G. T., et al., Biotechnology 9:165–169,1991.
de Nobel, H., et al., Trends in Cell Biol. 4:42–45,1994.
Deng, S., et al., J. Biol. Chem. 269:9533–9538, 1994.
Denzin, L. K., et al., Mol. Immol. 30:1331–1345, 1993.
DiRienzo, J. M., et al., Ann. Rev. Blochem. 47: 481–532, 1978.
Droupadi, P. R., et al., J. Mol. Recog. 5:173–179,1993.
Eilat et al., (1992) PNAS USA 89:6871–6875.
Ellman, et al., (1997) Proc. Natl. Acad. Sci. USA 94, 2779–2782.
Engel et al., (1992) Science 256:1318–1321.
Fischman, A. J., et al., J. Nucl. Med.. 34:2253–2263, 1993.
Foote, J., et al., Nature 352: 530–532, 1991.
Francisco, S. A., et al., PNAS 90:10444–10448,1993.
Garrard, L. J., et al., Gene 128: 103–109, 1993.
Georgiou, et al., (1997) Nat. Biotechnol. 15, 29–34.
Gilli, P., et al., J. Phys. Chem. 98:1515–1518, 1994.
Gilson, M. K., et al., Proteins:Struc., Func., Genet. 3:32–52, 1988.
Goldenberg, D. M. et al., Am. J. Med. 94:297312,1993.
Goldenberg, D. M., et al., Int. J Oncol. 3:5–11, 1993.
Greener, A., et al., Strat. in MoL Biol. 7: 32–34, 1994.
Guddat, L. W., et al., J. Mol. Biol. 236:247–274, 1994.
Gunther, R., et al., J. BioL Chem. 268: 7728–7732, 1993.
Hammond, C., Helenius, A. Curr. Opin. Cell Biol. 5:523–529, 1995.
Hand, P. H., et al., Cancer 73:1105–1113,1994.
Hawkins, R. E., et al., J. MoL BioL 234; 958–964,1993.
Hawkins, R. E., et al., Mol. Riol. 226: 889–896, 1992.
Herron, J. N., et al., Biochemistry 25:4602–4609, 1986.
Hibbits, K. A., et al., Biochemistry 33:3584–3590,1994-
Hilzemann, R. TIPS 9:408–411, 1988.
Holland, J. I. Adaptation in Natural and Artificial Systems, MIT Press, Cambridge, 1992.
Holst, M., et al., Proteins: Struct., Func., & Gen. 18:231–245, 1994.
Horwitz, A. H., et al., PNAS 85: 8678–8682, 1988.
Huse, W, D., et al., Science 246: 1275–1291, 1989.
Huston, J. S., et al., PNAS 85:5879, 1988.
Ishikawa, E., et al., J. Clin. Lab. Anal. 7:376–393, 1993.
Johnsson, N., et al., Cell, in press, 1994.
Johnston, M., et al., Mol. Cell. Biol. 4:1440–1448, 1984.
Kang, A. S., et al., PNAS 88:11120–11123, 1991.
Kappler et al., (1994) PNAS USA 91:8462–8466.
Kelley, R. F., et al., Biochemistry 32;6828–6835, 1993.
Kozack, R. E., et al., Protein Sci. 2:915–926, 1993.
Kranz, D. M., et al., J. Biol. Chem. 257:6987–6995, 1982.
Kricka, L. J, J, Clin. Immunoassay 16:267–271, 1993.
Lipke, P. N., et al., Microbiol, Rev. 56:180–194, 1992.
Low, N. M., et al., J. Mol. Biol. 260:359–368, 1996.
Lu, C.-F., et al., J. Cell Biol. 128:333–340, 1995.
Mallender, W. D., et al., J. BioL Chem. 269: 199–206, 1994.
Marks, J. D., Griffiths, A. D., Malmq ' vist, M., Clackson, T. P., Bye, J. M.,
Ward, A. C. Nucl. Acids. Res. 18:5319, '1991.
Winter, G. "By-Passing Immunization: Building High Affinity Human
Antibodies by Chain Shuffling." Biotechnology 10:779–783,1992.
Marks, J. D., et al., J. BioL Chem. 267: 16007–16010, 1992.
McKearn, T. J. Cancer 71:4302–4313, 1993,
Miettinen, M. Ann. Med. 25:221–233, 1993.
Moks, T., et al., Biochemistry 26:5239–5244,1987.
Mukkur, T. K. S. CRC Crit. Rev. Biochem. 16:133–167, 1984.
Muller, G. W., et al., J. Med. Chem. 35:740–743, 1992.
Near, R. I., et al., Mol Immunol, 30: 369–377, 1993.
Necker et al., (1991) Eur. J. Immunol. 21:3035–3040.
Nell, L. J., et al., Biopolymers 32i 1 1–21, 1992.
Normington, K., et al., Cell 57:1223–1236,1999.
Novotny et al., (1991) PNAS USA 88:8646–8650.
Omelyanenko, V. G., et al., Biochemistry 32:10423–10429, 1993.
Riechmann, L., et al., Biochemistry 32:8848–8855, 1993,
Riechmann, L., et al., MoL Biol. 224:913–918, 1992.
Roberets, S., et al., Nature 328:731–734,1987.
Roy, A., et al., Mol. Cell. Biol. 11:4196–4206, 1991.
Rumbley, C. A., et al., J. Biol. Chem. 268: 13667–13674, 1993.
Schreuder, M. P., et al., Yeast 9:399–409, 1993.
Schreuder, M. P.,et al., Trends Biotechnol. 14:115–120, 1996.
Searle, M. S., et al., Anals de Quimica 89:17–26, 1993.
Serafini, A. N. J. Nucl. Med. 34:533–536, 1993.
Sigurskjold, B. W., et al., Eur. J. Biochem. 197:239–246, 1991.
Slanetz et al., (1991) Eur. J. Immunol. 21:179–183.
Soo Hoo et al., (1992) PNAS USA 89:4759–4763.
Stemmer, W. P. C. Pro. Nat. Acad. Sci. U.S.A. 91:10747–10751, 1994*a*.
Stemmer, W. P. C. Nature .370:389–391, 1994*b*.
Stemmer, W. P. C.et al., BioTechniquesl 4:256–265,1993.
Ward, M., et al., Biotechnology 8:435–440, 1990.

Ward et al. (1991) Scand. J. Immunol. 34:215–220.
Williams, D. H., et al., PNAS 90:1172–1178,1993.
Wood, C. R., et al., Nature 314:446–449, 1985.
Wulfing et al. (1994) J. Mol. Biol. 242:655–669.
Yaimush, M., et al., Crit. Rev. Ther. Drug Carr. Sys. 10:197–252, 1993.
Yarmush, M. L., et al., Biotech. Adv. 10:413–446, 1992.
Zaccolo, M., et al., Int. J. Clin. Lab. Res. 23:192–198, 1993.
Zebedee, S. L., et al., PNAS 89-.3175–31795 1992.
Gietz, et al., (1995) Yeast 11, 355–360.
Gunneriusson, et al., (1996) J. Bacteriol. 178, 1341–1346.
Hoogenboom, H. R. (1997) Trends Biotechnol. 15, 62–70.
Knappik, A., & Pluckthun, A. (1995) Prot. Eng. 8, 81–89.
Kretzschmar, et al., (1995) Anal. Biochem. 224, 413–419.
Ladner, R. C. (1995) Trends Biotechnol. 13, 426–430.
Lowman, et al., (1991) Biochemistry 30, 10832–10838.
Markland, et al., (1996) Methods Enzymol. 267, 28–51.
Matthews, D. J., & Wells, J. A. (1993) Science 260, 1113–1117.
McDuffie, et al., (1986) Proc. Natl. Acad. Sci. USA 83, 8728.
Patten, et al., (1996) Science 271, 1086–1091.
Petsko, G. (1996) Nature 384 (Supplement), 7–9.
Phizicky, E. M., & Fields, S. (1995) Microbiol. Rev. 59, 94–123.
Rabinowitz, et al., (1996) Proc. Natl. Acad. Sci. 93, 1401–1405.
Roberts, I. S. (1996) Annu. Rev. Microbiol. 50, 285–315.
Rode, et al., (1996) Biotechniques 21, 650.
Roehm, et al., (1985) J. Immunol. 135, 2176.
Schier, et al., (1996) J. Mol. Biol. 263, 551–567.
Schlueter, et al., (1996) J. Mol. Biol. 256, 859–869.
Schodin, et al., (1996) Mol. Immunol. 33, 819–829.
Thompson, et al., (1996) J. Mol. Biol. 256, 77–88.
Ulrich, H. D., Patten, P. A., Yang, P. L., Romesberg, F. E., & Schultz, P. G (1995) Proc. Natl. Acad. Sci. USA 92, 11907–11911.
Walker, K. W., & Gilbert, H. F. (1994) J. Biol. Chem 269, 28487–28493.
Wang, C. I., Yang, Q., et al. (1996) Methods Enzymol. 267, 52–68.
Yang, et al., (1995) J. Mol. Biol. 254, 392–403.
Yelton, et al., (1995) J. Immunol. 155, 1994–2004.

Any patents or publications mentioned in this specification are indicative of the levels of those skilled in the art to which the invention pertains. These references are incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, molecules, and specific compounds described herein are presently representative of preferred embodiments, are exemplary, and are not limitations on the scope of the invention. Changes therein and other uses will occur to those skilled in the art which are encompassed within the spirit of the invention as defined by the scope of the claims.

What is claimed is:

1. A method for selecting proteins with enhanced phenotypic properties relative to those of a wild-type of said protein, comprising the steps of:

transforming yeast cells with a vector expressing a protein to be tested fused to a yeast cell wall protein, wherein mutagenesis is used to a generate a variegated population of mutants of the protein to be tested;

contacting said yeast cells with a first label, wherein said first label associates with yeast expressing said protein having enhanced phenotypic properties and does not associate with yeast which do not express said protein having enhanced phenotypic properties;

isolating said yeast cells with which said first label is associated;

analyzing and comparing said phenotypic properties of said mutant protein expressed by yeast with phenotypic properties of said wild-type protein; and selecting yeast cells exhibiting mutant proteins with enhanced phenotypic properties over the wild-type protein;

where enhanced phenotypic properties are one or more of surface expression level, stability, secretion levels and solubility.

2. The method of claim 1, wherein said protein to be tested is an antibody, Fab, Fv, or scFv antibody fragment.

3. The method of claim 1, wherein said protein to be tested is the ligand binding domain of a cell surface receptor.

4. The method of claim 1, wherein the protein to be tested is fused by its N terminus to the C terminus of said yeast cell wall protein.

5. The method of claim 1, wherein the yeast cell wall protein is an agglutinin.

6. The method of claim 1, wherein said yeast is of a genus selected from the group consisting of Saccharomyces, Pichia, Hansenula, Schizosaccharomyces, Kluyveromyces, Yarrowia, and Candida.

7. The method of claim 1, wherein said mutants of the protein to be tested are selected from the group consisting of single mutants and multiple mutants.

8. The method of claim 1, wherein said first label is selected from the group consisting of magnetic particles attached to a ligand for the protein to be and fluorescent labels.

9. The method of claim 1, wherein selection of mutated proteins of interest with enhanced phenotypic properties involves iterative cycles of said transforming and contacting steps.

10. The method of claim 1, further comprising the steps of:

contacting said yeast cells with a second label, wherein said vector used to transform said yeast cells contains means for expressing a polypeptide sequence fused to said protein to be tested to produce a fusion polypeptide and said second label associates with yeast cells expressing said fusion polypeptide and does not associate with yeast cells which do not express said fusion polypeptide;

enriching a transformed yeast population by quantitating said second label, wherein an occurrence of said second label is directly proportional to an abundance of said fusion polypeptides expressed on the cell surface; and comparing said quantitation of said first label to said quantitation of said second label to determine surface expression levels of said protein to be tested.

11. The method of claim 1, further comprising the steps of:

cloning a gene encoding said selected mutant proteins into a vector adapted for expression in a eukaryotic cell; and expressing said mutant protein in said eukaryotic cell, wherein said enhanced phenotype properties of said mutant protein are confirmed by comparing the properties of said enhanced phenotypic properties of said mutant protein with the properties of said wild-type protein.

12. The method of claim 1, further comprising the steps of:

cloning a gene encoding said selected mutant proteins into a vector adapted for expression in a prokaryote; and expressing said mutant protein in said prokaryote, wherein said enhanced phenotypic properties of said mutant protein are confirmed by comparing the properties of said enhanced phenotypic properties of said mutant protein with the properties of said wild-type protein.

13. The method of claim 3, wherein said cell surface receptor is a T cell receptor.

14. The method of claim 10, wherein an increase in said surface expression levels of said mutant protein to be tested relative to the level of surface expression of the wild-type protein tested can be used to select for desirable phenotypic properties of said mutant protein, where said desired phenotypic properties include one or more of intracellular expression level, stability, secretion levels and solubility.

15. The method of claim 10, wherein said polypeptide portion of said fusion polypeptide recognized by said second label is an epitope tag.

16. The method of claim 10, wherein said first label and said second label are fluorescent labels.

17. The method of claim 11, wherein said eukaryotic cell is selected from the group consisting of mammalian, insect and yeast cells.

* * * * *

UNITED STATES PATENT AND TRADEMARK OFFICE
CERTIFICATE OF CORRECTION

PATENT NO. : 6,300,065 B1
DATED : October 9, 2001
INVENTOR(S) : Kieke et al.

It is certified that error appears in the above-identified patent and that said Letters Patent is hereby corrected as shown below:

Column 4,
Line 61, delete the period "." between "label" and "associates".

Column 5
Line 38, delete "TIDFYLK" and replace with -- TDFYLK --.

Column 7,
Line 5, delete "a" after "is used to".

Column 9,
Line 65, delete "round" and replace with -- rounds --.

Column 14,
Line 4, delete "E1HHHHHH" and replace with -- HHHHHH --

Column 16,
Line 37, delete "-10.0 g." and replace with -- 10.0 g. --.

Column 17,
Lines 62-63, delete "make a n exact" and replace with -- make an exact --.

Column 19,
Line 27, delete "DNAby"and replace with -- DNA by --.

Column 20,
Line 28, delete "CEN BANK" and replace with -- GEN BANK --.
Line 64, delete "TAGATTATCCTCGAG CT-3'" and replace with
-- TAGATTATCCTCGAGCT-3' --.

Column 21,
Line 6, delete "_pCT201" and replace with -- pCT201 --.
Line 46, delete "PCRproduct" and replace with -- PCR product --.
Line 61, delete the comma "," after "may be".

Column 23
Line 19, delete "Ouantitation" and replace with -- Quantitation --

UNITED STATES PATENT AND TRADEMARK OFFICE
CERTIFICATE OF CORRECTION

PATENT NO. : 6,300,065 B1
DATED : October 9, 2001
INVENTOR(S) : Kieke et al.

It is certified that error appears in the above-identified patent and that said Letters Patent is hereby corrected as shown below:

Column 29,
Line 38, delete "2.4x110$^{-3}$" and replace with -- 2.4x10$^{-3}$ --.

Column 31,
Line 38, delete "500 ml" and replace with -- 500 µl --.
Line 54, delete "1/2000of" and replace with -- 1/2000 of --.

Column 34,
Line 9, delete "(FIG. 4B)" and replace with -- (FIG. 14B) --.

Column 40,
Line 23, delete "doublings)" and replace with -- doublings)) --.
Line 26, delete "25 (L" and replace with -- 25 mL --.

Column 41,
Line 34, delete "a" after "determined as".
Line 49, delete "were" and replace with -- was --.

Column 42,
Lines 13-14, delete "need FIG. 4 from Shusta et al.="

Column 43,
Line 31, delete "253-2631" and replace with -- 253-263 --.

Column 45,
Line 9, delete ".3175-31795" and replace with -- 3175-3179 --.

UNITED STATES PATENT AND TRADEMARK OFFICE
CERTIFICATE OF CORRECTION

PATENT NO. : 6,300,065 B1
DATED : October 9, 2001
INVENTOR(S) : Kieke et al.

It is certified that error appears in the above-identified patent and that said Letters Patent is hereby corrected as shown below:

Column 57,
Line 58, after "to be" please insert -- tested --.

Signed and Sealed this

Tenth Day of May, 2005

JON W. DUDAS
*Director of the United States Patent and Trademark Office*

```
                            SEQUENCE LISTING

<160> NUMBER OF SEQ ID NOS: 26

<210> SEQ ID NO 1
<211> LENGTH: 9
<212> TYPE: PRT
<213> ORGANISM: Unknown
<220> FEATURE:
<223> OTHER INFORMATION: Description of Unknown Organism:Epitope Tag

<400> SEQUENCE: 1

Tyr Pro Tyr Asp Val Pro Asp Tyr Ala
  1               5

<210> SEQ ID NO 2
<211> LENGTH: 10
<212> TYPE: PRT
<213> ORGANISM: Unknown
<220> FEATURE:
<223> OTHER INFORMATION: Description of Unknown Organism:Epitope Tag

<400> SEQUENCE: 2

Glu Gln Lys Leu Ile Ser Glu Glu Asp Leu
  1               5                  10

<210> SEQ ID NO 3
<211> LENGTH: 6
<212> TYPE: PRT
<213> ORGANISM: Unknown
<220> FEATURE:
<223> OTHER INFORMATION: Description of Unknown Organism:Epitope Tag

<400> SEQUENCE: 3
```

```
Asp Thr Tyr Arg Tyr Ile
  1               5

<210> SEQ ID NO 4
<211> LENGTH: 6
<212> TYPE: PRT
<213> ORGANISM: Unknown
<220> FEATURE:
<223> OTHER INFORMATION: Description of Unknown Organism:Epitope Tag

<400> SEQUENCE: 4

Thr Asp Phe Tyr Leu Lys
  1               5

<210> SEQ ID NO 5
<211> LENGTH: 9
<212> TYPE: PRT
<213> ORGANISM: Unknown
<220> FEATURE:
<223> OTHER INFORMATION: Description of Unknown Organism:Epitope Tag

<400> SEQUENCE: 5

Glu Glu Glu Glu Tyr Met Pro Met Glu
  1               5

<210> SEQ ID NO 6
<211> LENGTH: 11
<212> TYPE: PRT
<213> ORGANISM: Unknown
<220> FEATURE:
<223> OTHER INFORMATION: Description of Unknown Organism:Epitope Tag

<400> SEQUENCE: 6

Lys Pro Pro Thr Pro Pro Pro Glu Pro Glu Thr
  1               5                  10

<210> SEQ ID NO 7
<211> LENGTH: 6
<212> TYPE: PRT
<213> ORGANISM: Unknown
<220> FEATURE:
<223> OTHER INFORMATION: Description of Unknown Organism:Epitope Tag

<400> SEQUENCE: 7

His His His His His His
  1               5

<210> SEQ ID NO 8
<211> LENGTH: 5
<212> TYPE: PRT
<213> ORGANISM: Unknown
<220> FEATURE:
<223> OTHER INFORMATION: Description of Unknown Organism:Epitope Tag

<400> SEQUENCE: 8

Arg Tyr Ile Arg Ser
  1               5

<210> SEQ ID NO 9
<211> LENGTH: 8
<212> TYPE: PRT
<213> ORGANISM: Unknown
<220> FEATURE:
<223> OTHER INFORMATION: Description of Unknown Organism:Epitope Tag

<400> SEQUENCE: 9

Asp Tyr Lys Asp Asp Asp Asp Lys
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:PCR Primer
      towards AGA2 gene of S. cerevisiae

<400> SEQUENCE: 10
attagaattc cctacttcat acattttcaa                                       30

<210> SEQ ID NO 11
<211> LENGTH: 73
<212> TYPE: DNA
<213> ORGANISM: Artificial Sequence
<220> FEATURE:
<223> OTHER INFORMATION: Description of Artificial Sequence:PCR Primer
      towards AGA2 gene of S. cerevisiae

<400> SEQUENCE: 11
attactcgag ctattactgc agagcgtagt ctggaacgtc gtatgggtaa aaacatact       60 gtgtgtttat ggg                                                         73

<210> SEQ ID NO 12
<211> LENGTH: 71
<212> TYPE: DNA
<213> ORGANISM: Artificial Sequence
<220> FEATURE:
<223> OTHER INFORMATION: Description of Artificial Sequence:PCR primer
      towards the factor Xa recognition sequence

<400> SEQUENCE: 12
tcgacgattg aaggtagata cccatacgac gttccagact acgctctgca gtaatagatt      60
atcctcgagc t                                                           71

<210> SEQ ID NO 13
<211> LENGTH: 63
<212> TYPE: DNA
<213> ORGANISM: Artificial Sequence
<220> FEATURE:
<223> OTHER INFORMATION: Description of Artificial Sequence:PCR Primer
      towards the factor Xa recognition sequence

<400> SEQUENCE: 13
cgaggataat ctattactgc agagcgtagt ctggaacgtc gtatgggtat ctaccttcaa      60
tcg                                                                    63

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence:PCR Primer
      towards Gal promoter

<400> SEQUENCE: 14
aattggtacc                                                             10

<210> SEQ ID NO 15
<211> LENGTH: 10
<212> TYPE: DNA
<213> ORGANISM: Artificial Sequence
<220> FEATURE:

```
<223> OTHER INFORMATION: Description of Artificial Sequence:PCR Primer
      towards Gal promoter

<400> SEQUENCE: 15
gatcgaattc                                                              10

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:PCR primer
      towards 4-4-20 scFv

<400> SEQUENCE: 16
ggttggccaa gctagcgacg tcgttatgac tcaa                                   34

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence:PCR Primer
      towards 4-4-20 scFv

<400> SEQUENCE: 17
ggccggccaa ctcgagctat tacaagtctt cttcagaaat aagcttttgt tctgaggaga       60
cggtgactga                                                              70

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:PCR Primer
      towards AGA1 gene of S. cerevisiae

<400> SEQUENCE: 18
attagaattc agctaaaaaa accaaaaaat                                        30

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence:PCR Primer
      towards AGA1 gene of S. cerevisiae

<400> SEQUENCE: 19
attactcgag ctattaactg aaaattacat tgc                                    33

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence:Linker
      between PCR products to maintain correct reading frame

<400> SEQUENCE: 20

Gly Gly Gly Gly Ser Gly Gly Gly Gly Ser Gly Gly Gly Gly Ser
 1               5                  10                  15

<210> SEQ ID NO 21
<211> LENGTH: 1172
<212> TYPE: DNA
```

<213> ORGANISM: Artificial Sequence
<220> FEATURE:
<223> OTHER INFORMATION: Description of Artificial Sequence:Cloned PCR
    products to produce AFA2-HA-4-420 gene cassette

<400> SEQUENCE: 21

```
attagaattc cctacttcat acattttcaa ttaagatgca gttacttcgc tgttttcaa      60
tattttctgt tattgcttca gttttagcac aggaactgac aactatatgc gagcaaatcc    120
cctcaccaac tttagaatcg acgccgtact ctttgtcaac gactactatt ttggccaacg    180
ggaaggcaat gcaaggagtt tttgaatatt acaaatcagt aacgtttgtc agtaattgcg    240
gttctcaccc ctcaacaact agcaaaggca gccccataaa cacacagtat gttttaagg     300
acaatagctc gacgattgaa ggtagatacc catacgacgt tccagactac gctctgcagg    360
ctagcgacgt cgttatgact caaacaccac tatcacttcc tgttagtcta ggagatcaag    420
cctccatctc ttgcagatct agtcagagcc ttgtacacag taatggaaac acctatttac    480
gttggtacct gcagaagcca ggccagtctc caaggtcct gatctacaaa gtttccaacc     540
gatttctgg ggtcccagac aggttcagtg gcagtggatc agggacagat ttcacactca    600
agatcagcag agtggaggct gaggatctgg gagtttattt ctgctctcaa agtacacatg    660
ttccgtggac gttcggtgga ggcaccaagc ttgaaattaa gtcctctgct gatgatgcta    720
agaaggatgc tgctaagaag gatgatgcta agaaagatga tgctaagaaa gatggtgacg    780
tcaaactgga tgagactgga ggaggcttgg tgcaacctgg gaggcccatg aaactctcct    840
gtgttgcctc tggattcact tttagtgact actggatgaa ctgggtccgc cagtctccag    900
agaaaggact ggagtgggta gcacaaatta gaaacaaacc ttataattat gaaacatatt    960
attcagattc tgtgaaaggc agattcacca tgtcaagaga tgattccaaa agtagtgtct   1020
acctgcaaat gaacaactta agagttgaag catgggtat ctattactgt acgggttctt    1080
actatggtat ggactactgg ggtcaaggaa cctcagtcac cgtctcctca gaacaaaagc   1140
ttatttctga agaagacttg taatagctcg ag                                 1172
```

<210> SEQ ID NO 22
<211> LENGTH: 366
<212> TYPE: DNA
<213> ORGANISM: Artificial Sequence
<220> FEATURE:
<223> OTHER INFORMATION: Description of Artificial Sequence:PCR products
    of wild type scFv-KJ16

<400> SEQUENCE: 22

```
gacgtcctgg tgacccaaac tcctgcctcc ctgtctgcat ctccggatga atctgtcacc      60
atcacatgcc aggcaagcca ggacattggt acttcgttag tttggtatca gcagaaacca    120
gggaaatctc ctcagctcct ggtctatagt gcaactatct tggcagatgg ggtcccatca    180
aggttcagtg gcagtagatc tggcacacag tattctctta agatcaacag actacaggtt    240
gaagatattg gaacctatta ctgtctacag gtttctagtt ctccgtacac gtttggagct    300
ggcaccaagc tggagctcaa acggtcctca gaacaaaagc ttatttccga agaagatttg    360
tagtaa                                                              366
```

<210> SEQ ID NO 23
<211> LENGTH: 366
<212> TYPE: DNA
<213> ORGANISM: Artificial Sequence
<220> FEATURE:
<223> OTHER INFORMATION: Description of Artificial Sequence:PCR products of KJ16-mut4

<400> SEQUENCE: 23

```
gacgtcctgg tgacccaaac tcctgcctcc ctgtctgcat ctccggatga atctgtcacc      60
atcacatgcc aggcaagcca ggacattggt acttcgttag tttggtatca gcagaaacca     120
gggaaatctc ctcagctcct ggtctatagt gcaactatct ggcagatggg gtcccatca     180
aggttcagtg gcagtagatc tggcacacag tattctctta agatcaacag actacaggtt     240
gaagatattg aacctatta ctgtctacag gtttctagtt ctccgtacac gtttggagct     300
ggcaccaagc tggagctcaa acggtcctca gaacaagagc ttatttccga agaagatttg     360
tagtaa                                                                 366
```

<210> SEQ ID NO 24
<211> LENGTH: 366
<212> TYPE: DNA
<213> ORGANISM: Artificial Sequence
<220> FEATURE:
<223> OTHER INFORMATION: Description of Artificial Sequence:PCR products
      of KJ16-mut7

<400> SEQUENCE: 24

```
gacgtcctgg tgacccaaac tcctgcctcc ctgtctgcat ctccggatga atctgtcacc      60
atcacatgcc aggcacgcca ggacattggt acttcgttag tttggtatca gcagaaacca     120
gggaaatctc ctcagctcct ggtctatagt gcaactatct ggcagatggg gtcccatca     180
aggttcagtg gcagtaaatc tggcacacag tattctctta agatcaacag actacaggtt     240
gaagatattg aacctatta ctgtctacag gtttctagtt ctccgtacac gtttggagct     300
ggcaccaagc tggagctcaa acggtcctca gaacaaaagc ttatttccga agaagatttg     360
tagtaa                                                                 366
```

<210> SEQ ID NO 25
<211> LENGTH: 747
<212> TYPE: DNA
<213> ORGANISM: Artificial Sequence
<220> FEATURE:
<223> OTHER INFORMATION: Description of Artificial Sequence:Sequence
      showing mutations in T-cell receptor

<400> SEQUENCE: 25

```
gacgtcgcag tcacccaaag cccaagaaac aaggtggcag taacaggagg aaaggtgaca      60
ttgagctgta atcagactaa taaccacaac aacatgtact ggtatcggca ggacacgggg     120
catgggctga ggctgatcca ttattcatat ggtgctggca gcactgagaa aggagatatc     180
cctgatggat acaaggcctc cagaccaagc caagagaact tctccctcat tctggagttg     240
gctaccccct ctcagacatc agtgtacttc tgtgccagcg gtgggggggg caccttgtac     300
tttggtgcgg gcacccgact atcggtgcta tcctccgcgg atgatgctaa gaaggatgct     360
gctaagaagg atgatgctaa gaaagatcat gctaagaaag atgcacagtc agtgacacag     420
cccgatgctc gcgtcactgt ctctgaagga gcctctctgc agctgagatg caagtattcc     480
tactctgcga caccttatct gttctggtat gtccagtacc cgcggcaggg gctgcagctg     540
ctcctcaagt actattccgg agaccagtg gttcaaggag tgaatggctt tgaggctgag     600
ttcagcaaga gcaactcttc cttccacctg cggaaagcct ccgtgcactg gagcgactcg     660
gctgtgtact tctgtgctgt gagcggcttt gcaagtcgcg tgacatttgg atctggcaca     720
aaagtcattg ttctaccata catctag                                         747
```

-continued

```
<210> SEQ ID NO 26
<211> LENGTH: 4
<212> TYPE: PRT
<213> ORGANISM: Unknown
<220> FEATURE:
<223> OTHER INFORMATION: Description of Unknown Organism:Epitope Tag

<400> SEQUENCE: 26

Ile Glu Gly Arg
```